US011407746B2

(12) United States Patent
Saito et al.

(10) Patent No.: US 11,407,746 B2
(45) Date of Patent: *Aug. 9, 2022

(54) GRISEOFULVIN COMPOUND AND PHARMACEUTICAL USE THEREOF

(71) Applicant: Daiichi Sankyo Company, Limited, Tokyo (JP)

(72) Inventors: Keiji Saito, Atsugi (JP); Katsuyoshi Nakajima, Shinagawa-ku (JP); Yasuyuki Ogawa, Yokosuka (JP); Mitsuhiro Makino, Shinagawa-Ku (JP); Kaori Ito, Koto-ku (JP); Seiko Nagata, Shinagawa-ku (JP); Makoto Hirasawa, Shinagawa-ku (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/648,570

(22) PCT Filed: Sep. 28, 2018

(86) PCT No.: PCT/JP2018/036160
§ 371 (c)(1),
(2) Date: Mar. 18, 2020

(87) PCT Pub. No.: WO2019/065928
PCT Pub. Date: Apr. 4, 2019

(65) Prior Publication Data
US 2020/0216433 A1  Jul. 9, 2020

(30) Foreign Application Priority Data
Sep. 29, 2017  (JP) .............................. JP2017-191690

(51) Int. Cl.
| *C07D 413/14* | (2006.01) |
| *C07D 307/94* | (2006.01) |
| *C07D 405/10* | (2006.01) |
| *C07D 413/10* | (2006.01) |
| *C07D 309/12* | (2006.01) |
| *C07D 407/12* | (2006.01) |
| *C07D 405/14* | (2006.01) |
| *C07D 498/10* | (2006.01) |

(52) U.S. Cl.
CPC ......... *C07D 413/14* (2013.01); *C07D 307/94* (2013.01); *C07D 309/12* (2013.01); *C07D 405/10* (2013.01); *C07D 405/14* (2013.01); *C07D 407/12* (2013.01); *C07D 413/10* (2013.01); *C07D 498/10* (2013.01)

(58) Field of Classification Search
CPC .. C07D 413/14; C07D 307/94; C07D 309/12; C07D 405/10; C07D 405/14; C07D 407/12; C07D 413/10; C07D 498/10
USPC ...................................................... 514/274
See application file for complete search history.

(56) References Cited

U.S. PATENT DOCUMENTS

| 10,570,109 B2 | 2/2020 | Saito et al. |
| 10,654,821 B2 | 5/2020 | Saito et al. |
| 10,975,052 B2 * | 4/2021 | Saito .................... C07D 405/04 |
| 2015/0191443 A1 | 7/2015 | Marion et al. |
| 2020/0216433 A1 | 7/2020 | Saito et al. |
| 2020/0239425 A1 | 7/2020 | Saito et al. |

FOREIGN PATENT DOCUMENTS

| CN | 104860909 A | 8/2015 |
| DE | 4430910 A1 | 3/1996 |
| JP | H03255081 A | 11/1991 |
| WO | 2009000937 A1 | 12/2008 |
| WO | 2010072770 A2 | 7/2010 |
| WO | 2010124695 A1 | 11/2010 |
| WO | 2017170623 A1 | 10/2017 |
| WO | 2019065928 A1 | 4/2019 |

OTHER PUBLICATIONS

"Extended European Search Report corresponding to European Application No. 18860748.5 dated May 10, 2021".
"Office Action corresponding to Brazilian Application No. 11 2018 069712 5 dated Apr. 15, 2021".
D'arcy, P.F, et al., "The Anti-Flammatory Action of Griseofulvin in Experimental Animals", Pharmaceutical and Clinical Research 12(1)1659-665 (Sep. 1, 1960).
"U.S. Appl. No. 16/561,459: office action dated Sep. 27, 2019".
"U.S. Appl. No. 16/844,621; office action dated May 15, 2020".
"U.S. Appl. No. 16/844,621; office action dated Aug. 18, 2020".
"Extended European Search Report corresponding to European Application No. 17775160.9 dated Sep. 20, 2019".
Gentles, J. C., "Experimental Ringworm in Guinea Pigs: Oral Treatment With GriseofulVin," Nature 182:476-477, Aug. 1958.
"International Preliminary Report on Patentability corresponding international Application No. PCT/JP2017/012777 dated Oct. 11, 2018".
"International Preliminary Report on Patentability corresponding to International Application No. PCT/JP2018/036160 dated Apr. 9, 2020".
"International Search Report and Written Opinion corresponding to International Application No. PCT/JP2018/036160 dated Dec. 11, 2018".

(Continued)

*Primary Examiner* — Kristin A Vajda
(74) *Attorney, Agent, or Firm* — Myers Bigel, P.A.

(57) ABSTRACT

The present invention addresses the problem of providing a compound for prophylaxis and/or treatment of central inflammatory diseases, or a pharmacologically acceptable salt thereof. The present invention addresses a compound of a general formula (I) or a pharmacologically acceptable salt thereof as a means to solve the problem. [$R^1$: a C1-C6 alkyl group or the like, $R^2$: a C1-C6 alkyl group or the like, A: a 5-membered aromatic hetero-ring or the like, $R^3$, $R^{3'}$: a C1-C6 alkyl group or the like.

20 Claims, 2 Drawing Sheets

(56) References Cited

OTHER PUBLICATIONS

"International Search Report and Written Opinion dated Jun. 6, 2017, issued in corresponding International Application No. PCT/JP2017/012777, filed Mar. 29, 2017, 9 pages."
"Office Action corresponding to Australian Application No. 2017244777 dated Jul. 6, 2020".
"Office Action corresponding to Canadian Application No. 3,018,316 dated Oct. 1, 2019".
"Office Action corresponding to Colombian Patent Application No. NC2018/0010787 dated May 7, 2020".
"Office Action corresponding to Indian Application No. 201817039908 dated Oct. 25, 2019".
"Office Action corresponding to Indonesian Application No. P-00201807645 dated Dec. 10, 2020".
"Office Action corresponding to Israeli Application No. 262,020 dated Jun. 22, 2020".
"Office Action corresponding to Japanese Application No. 2018-508114 dated Oct. 21, 2020".
"Office Action corresponding to Russian Application No. 2018137851 dated Apr. 17, 2020".
"Office Action corresponding to Taiwanese Application No. 106110433 dated Dec. 24, 2020".
Arkley, V., et al., "Griseofulvin Analogues, Part I: Modification of the Aromatic Ring," Journal of the Chemical Society 241:1260-1268, Apr. 1962.
Asahina, et al., "Griseofulvin has a potential to modulate the expression of cell adhesion molecules on leukocytes and vascular endothelial cells", International Immunopharmacology 1(1):75-83 (2001).
Cohen, A., et al., "Treatment of Shoulder-Hand Syndrome With Griseofulvin," Journal of the American Medical Association 173(5):542-543, Jun. 1960.
Goodall, S. R., et al., "Griseofulvin Analogues. Part VII: Replacements in the Aromatic Ring," Journal of the Chemical Society 302:1610-1619, Mar. 1963.
Green, G. F. H., et al., "22. Griseofulvin Analogues. Part IX. Proton Magnetic Resonance Studies., Journal of the Chemical Society, 1964, pp. 144-148".
Ho, Y.-S., et al., "Griseofulvin Potentiates Antitumorigenesis Effects of Nocodazole Through Induction of Apoptosis and G2/M Cell Cycle Arrest in Human Colorectal Cancer Cells," International Journal of Cancer 91(3):393-401, Feb. 2001.
Kraft, R., et al., "A cell-based fascin bioassay identifies compounds with potential anti-metastasis or cognition-enhancing functions, Disease Models & Mechanisms, 2013, 6(1), pp. 217-235".
Oxford, A. E., et al., "XXIX. Studies in the Biochemistry of Micro-Organisms. LX. Griseofulvin, C17H17O6C1, A Metabolic Product, of Penicillium griseo-fulvum Dierckxx," Biochemical Journal 33(2)240-248, Feb. 1939.
Petersen, A. B., et al. "The Chemistry of Griseofulvin," Chemical Reviews 114(24):12088-12107, Dec. 2014.
Rodriguez, J. A., et al., "The effects of some porphyrinogenic drugs on the brain cholinergic system, Cellular and Molecular Biology, 2002, 48 (1), pp. 103-110".
Sehgal, et al., "Antifungal Agents: Unapproved Uses, Dosages, or Indications", Clinics in Dermatology 20:481-489 (2002).
Sehgal, V. N., et al., "Histopathological Evaluation of Griseofulvin Therapy in Lichen planus," Dermatologica 161 (1):22-27, 1980.
Sorrentino, L., et al., "Anti-inflammatory Properties of Griseofulvin," Agents and Actions 7(1):157-162, Mar. 1977.
Tamaki, K., et al., "Successful Treatment of Pigmented Purpuric Dermatosis With Griseofulvin," British Journal of Dematology 132(1):159-160, Jan. 1995.
Tamaki, K., et al., "Treatment of Plasma Cell Cheilitis Wth Griseofulvin," Journal of the American Academy of Dermatology 30(5, Pt 1):789-790, May 1994.
Vincent, A. M., et al., "Identification of candidate drugs for the treatment of ALS, Amyotrophic Lateral Sclerosis and Other Motor Neuron Disorders, 2005, 6(1), pp. 29-36".
Wehland, J., et al., "Interaction of Griseofulvin With Microtubules, Microtubule Protein and Tubulin," Journal of Molecular Biology 111(3):329-342, Apr. 1977.
Williams, D.I., et al., "Oral Treatment of Ringworm With Griseofulvin," The Lancet 2(7058): 1212-1213, Dec. 1958.
"Office Action corresponding to Chinese Application No. 201780017933.3 dated Sep. 18, 2021".
"Written Opinion corresponding to Singapore Application No. 11202002973W dated Aug. 31, 2021".
"Office Action corresponding to Indian Application No. 202017018710 dated Nov. 16, 2021".
"Office Action corresponding to Japanese Application No. 2019-545656 dated Mar. 4, 2022".
"Office Action corresponding to Korean Application No. 10-2018-7027758 dated Jan. 20, 2022".
"Office Action corresponding to Philippine Application No. 1-2018-502012 dated Feb. 10, 2022".
"Office Action corresponding to Russian Application No. 2020114910 dated Nov. 24, 2021".
Belikov, V. G, "Relationships between the Chemical Structure, Properties of the Compound, and Its Effect on a Living Body", Pharmaceutical Chemistry Chapter 2.6:27-29 (2017).
Kovaleva, M. A, et al., "Forced Swim Test in Preclinical Studies", International bulletin of veterinary medicine No. 4:90-95 (2015).
Kümmerer, Klaus , "Pharmaceuticals in the environment", Annual Review of Environment and Resources 35:57-75 (Aug. 18, 2010).
"Office Action corresponding to Israeli Application No. 273,339 dated Apr. 3, 2022".
"Examination Report corresponding to Australian Application No. 2018342423 dated Apr. 1, 2022".
"U.S. Appl. No. 17/212,373; office action dated Apr. 28, 2022".
"Office Action corresponding to Mexican Application No. MX/a/2020/003383 dated May 13, 2022".

\* cited by examiner

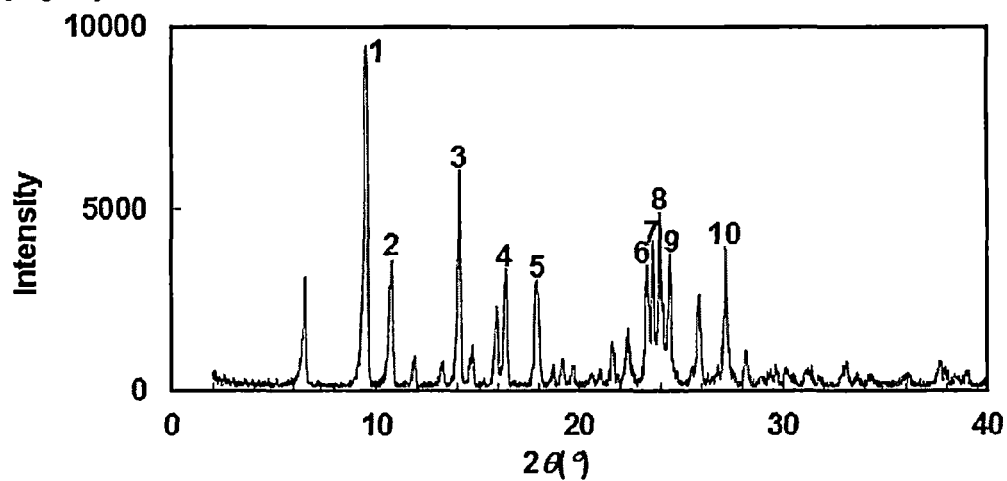
[Fig. 1]
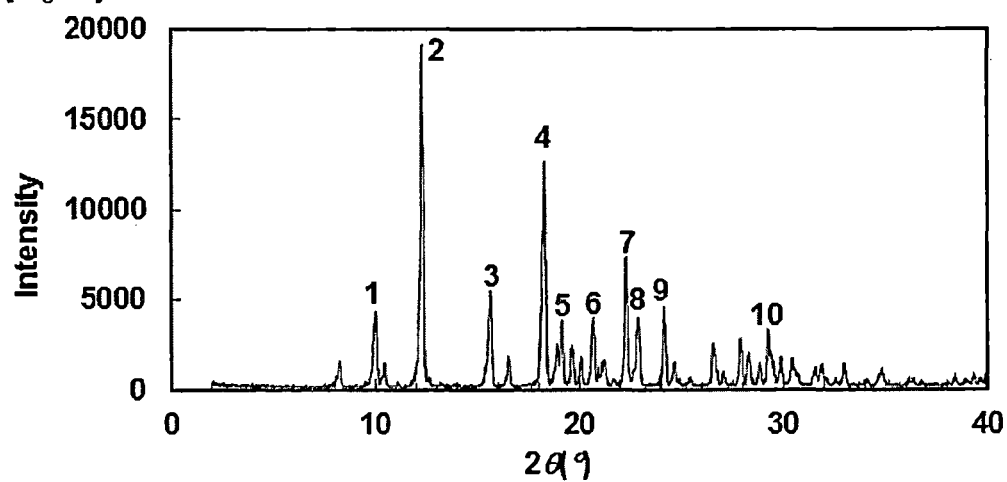
[Fig. 2]
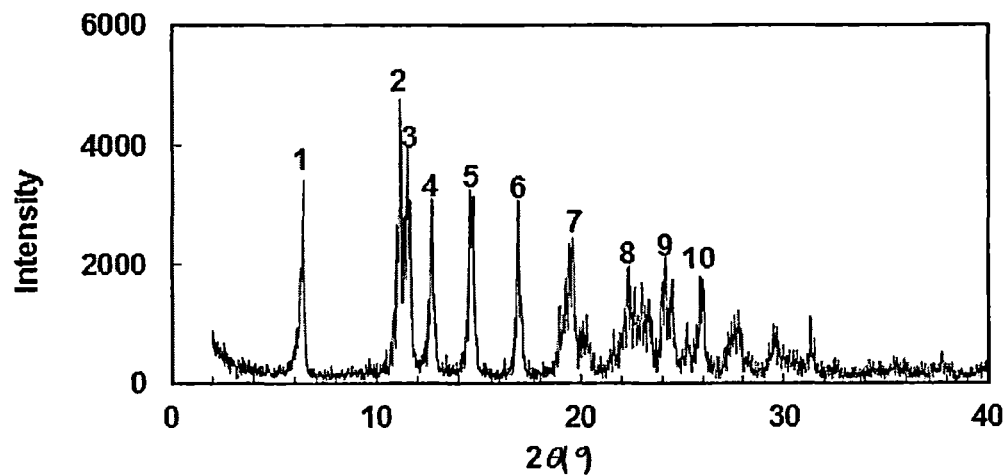
[Fig. 3]

[Fig. 4]
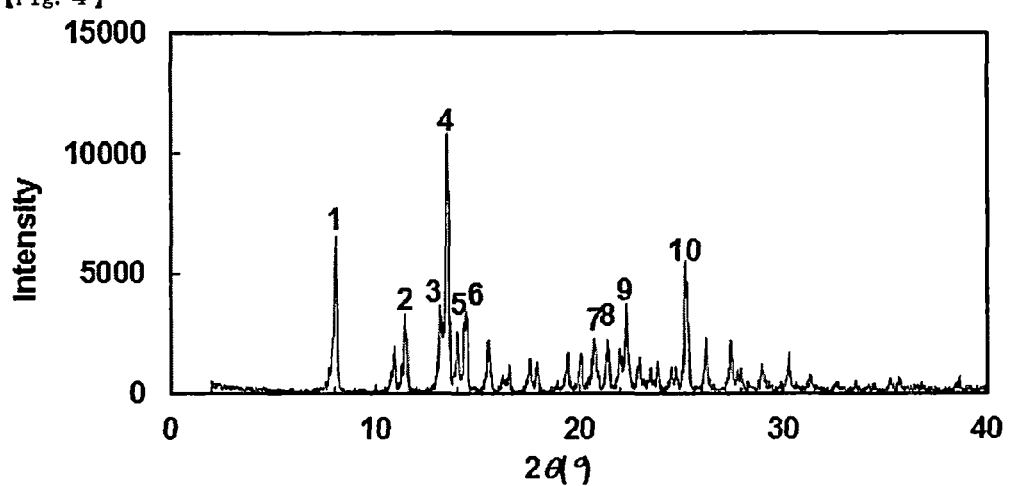

GRISEOFULVIN COMPOUND AND PHARMACEUTICAL USE THEREOF

CROSS-REFERENCE TO RELATED APPLICATIONS

This application is a § 371 national phase application of PCT Application No. PCT/JP2018/036160 filed Sep. 28, 2018, which claims priority to Japanese Application No. 2017-191690 filed Sep. 29, 2017, the entire contents of each of which is incorporated by reference herein.

TECHNICAL FIELD

The present invention relates mainly to a compound having a specific chemical structure having a central anti-inflammatory effect or a pharmacologically acceptable salt thereof, and to a pharmaceutical use thereof. In addition, the present invention relates to the mechanism of action, pharmaceutical composition, production of the pharmaceutical composition, methods for prevention and/or treatment, and the like of the compound or the pharmacologically acceptable salt thereof.

BACKGROUND ART

Griseofulvin is an antibiotic that was first isolated from *Penicillium griseofulvum*, a species of *penicillium* mold of *Aspergillus* by AE Oxford et al. in 1939 (non-patent literature 1). It is mainly orally administered, but it is a poorly soluble and easily absorbed drug, and the oral absorption kinetics thereof are complicated. It is used as an antifungal agent against dermatophytes such as *Microsporum (Microsporum)*, *Trichophyton (Trichophyton)*, and *Epidermophyton (Epidermophyton)* (non-patent literature 2 and 3).

Griseofulvin binds to tubulin in cells. This arrests the cell cycle at the G2/M phase, causes mitotic abnormalities, and suppresses the growth of various cells such as fungi, plants, and mammals. Growth suppression in fungal cells is induced at very low concentrations compared to mammalian cells, presumably due to the higher binding affinity for fungal tubulin compared to mammalian tubulin. In addition, it also has the effect of suppressing dynamic instability of microtubules and stabilizing microtubule movement by binding to microtubule-associated proteins (MAPs) (non-patent literature 4).

Griseofulvin has a growth suppression effect on human cancer cells and apoptosis-inducing activity and exhibits antitumor activity on tumors transplanted into athymic nude mice when used in combination with nocodazole. Therefore, it is also expected to have an effect as an anticancer agent (non-patent literature 5).

On the other hand, it has been known for long time to have an anti-inflammatory effect in addition to an anti-fungal effect. For example, it has been found to exhibit an anti-inflammatory effect on formalin edema and cotton pellet granuloma, which are rat inflammation models (non-patent literature 6). In actual clinical practice, it has been reported that it exhibits a pharmacological effect on lichen planus (lichen planus) (non-patent literature 7), plasma cell cheilitis (pla303sma cell cheilitis) (non-patent literature 8), and pigmented purpuric dermatosis (pigmented purpuric dermatosis) (non-patent literature 9), which are non-fungal inflammatory skin diseases.

In addition, it has been reported that it exhibits pharmacological effects on livedoid vasculitis (livedoid vasculitis) (non-patent literature 9), polyarthritis such as shoulder-hand syndrome (shoulder-hand syndrome) and scapulo-humeral peryarthritis (scapulo-humeral peryarthritis) (non-patent literature 6 and 10).

It has been found to have an effect on microtubules of leukocytes and an antagonistic effect on histamine, serotonin, prostaglandin, and the like, which are chemical mediators of inflammation in vitro (non-patent literature 6), but the details of the mechanism of action of griseofulvin in the anti-inflammatory effect are not clear.

As described above, griseofulvin having various physiological activities has undergone conversion of various substituents, and derivatives have been synthesized to date (non-patent literature 11).

In recent years, with the progress of research, the relationship between mental disorders, neurodegenerative diseases, and inflammation has been reported (non-patent literature 12 and 13).

It has been reported that stress increases the production of inflammatory cytokines from microglia and that blood cytokine (TNFα and the like) levels are high in patients with psychiatric disorders (depression, schizophrenia, and the like), and involvement of brain inflammation in mental illness has been suggested. In addition, in neurodegenerative diseases typified by Alzheimer's disease, it has also been suggested that proteins that are thought to be the cause thereof may trigger brain inflammation by activation of microglia.

PRIOR ART LITERATURE

Non-Patent Literature

Non-patent literature 1: Oxford A E, Raistric H, Simonart P, Studies in the biochemistry of micro-organisms: Griseofulvin, C(17)H(17)O(6)Cl, a metabolic product of *Penicillium griseo-fulvum* Dierckx. 1537917094409_0. 1939 Feb.; 33(2): 240-248.

Non-patent literature 2: Gentles J C, Experimental ringworm in guinea pigs: oal treatment with griseofulvin. Nature. 1958 Aug. 16; 182 4633: 476-477.

Non-patent literature 3: Williams D I, Marten R H, Sarkany I. Oral treatment ringworm with griseofulvin. Lancet. 1958 Dec. 6; 2 (7058): 1212-1213.

Non-patent literature 4: Wehland J, Herzog, W, Weber K. Interaction of griseofulvin with microtubules, microtubule protein and tubulin. J Mol Biol. 1977 Apr. 15; 111(3): 329-342.

Non-patent literature 5: Ho Y S, Duh J S, Jeng J H, Wang Y J, Liang Y C, Lin C H, Tseng C J, Yu C F, Chen R J, Lin J K. Griseofulvin potentiates antitumorigenesis effects of nocodazole through induction of apoptosis and G2/M cell cycle arrest in human colorectal cancer cells. Int J Cancer. 2001 Feb. 1; 91(3): 393-401.

Non-patent literature 6: Sorrentino L, Capasso F, Di Rosa M. Anti-inflammatory properties of griseofulvin. Agents Actions. 1977 Mar.; 7(1): 157-162.

Non-patent literature 7: Sehgal V N, Bikhchandani R, Koranne R V, Nayar M, Saxena H M. Histopathological evaluation of griseofulvin therapy in lichen planus. A double-blind controlled study. Dermatologica. 1980; 161 (1): 22-27.

Non-patent literature 8: Tamaki K, Osada A, Tsukamoto K, Ohtake N, Furue M. Treatment of plasma cell cheilitis with griseofulvin. J Am Acad Dermatol. 1994 May; 30(5 Pt 1): 789-790.

Non-patent literature 9: Tamaki K, Yasaka N, Osada A, Shibagaki N, Furue M. Successful treatment of pigmented purpuric dermatosis with griseofulvin. Br J Dermatol. 1995 Jan.; 132(1): 159-160.

Non-patent literature 10: Cohen A, Goldman J, Daniels R, Kanenson W. Treatment of shoulder-hand syndrome with griseofulvin. J Am Med Assoc. 1960 Jun. 4; 173: 542-543.

Non-patent literature 11: Peterson A B, Ronnest M H, Larsen T O, Clausen M H. The Chemistry of Griseofulvin. Chem. Rev. 2014 Dec.; 114: 12088-12107.

Non-patent literature 12: Kadota A. Neuroinflammation Hypothesis of Psychiatric Disorders, Psychiatria et Neurologia Japonica (2012) Vol. 114, No. 2, 124-133

Non-patent literature 13: Kadota A. Neurodegenerative Diseases, Neuroinflammation and Microglia, Clinical Neurology (2014) 54, 1119-1121

SUMMARY OF THE INVENTION

Problem to be Solved by the Invention

The present invention provides a compound having a specific chemical structure having a central anti-inflammatory effect useful as an active ingredient for the prevention and treatment of inflammatory diseases, a pharmacologically acceptable salt thereof, a pharmaceutical use thereof and the like, or a novel production method thereof and an intermediate thereof. The compound of the present invention, or the pharmaceutically acceptable salt thereof, has various different properties from the anti-inflammatory agents existing to date, so it is considered to be useful as a novel pharmaceutical.

In particular, the present invention provides a use for prevention and treatment of central inflammatory diseases with griseofulvin based on the finding of the central anti-inflammatory effect of griseofulvin. Furthermore, in the present invention, by optimizing the structure of griseofulvin, a compound having a superior central anti-inflammatory effect has been found, and a use thereof for prevention and treatment of central inflammatory diseases is provided.

Means for Solving the Problem

The present inventors have conducted intensive studies for the purpose of developing a compound useful as an active ingredient for the prevention and treatment of central inflammatory disease, a pharmacologically acceptable salt thereof, and the like; as a result, the compound, the pharmacologically acceptable salt thereof, the pharmaceutical use thereof, and the like of the present invention were found. In addition, it has been found that the compound and the pharmacologically acceptable salt thereof of the present invention have excellent properties in terms of central anti-inflammatory activity, bioavailability, in vitro activity, in vivo activity, rapid effects of the drug, sustained drug effect, physical stability, drug interaction, toxicity, and the like, and are useful as pharmaceuticals.

That is, the present invention is as described below.

[1]

A compound of the general formula (1) or a pharmacologically acceptable salt thereof.

[Chemical formula 1]

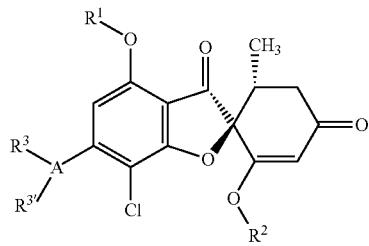

(1)

[The symbols in the formula are defined as follows.

$R^1$:

A C1-C6 alkyl group optionally substituted with the same or different one to two substituents selected from a substituent group X, a C3-C6 cycloalkyl group optionally substituted with the same or different one to two substituents selected from the substituent group X, or a 4-7 membered saturated heterocyclic group optionally substituted with the same or different one to two substituents selected from the substituent group X $R^2$:

A C1-C6 alkyl group optionally substituted with the same or different one to two substituents selected from the substituent group X, a C3-C6 cycloalkyl group optionally substituted with the same or different one to two substituents selected from the substituent group X, or a 4-7 membered saturated heterocyclic group optionally substituted with the same or different one to two substituents selected from the substituent group X

A:

A 5-membered aromatic heterocyclic ring, a 6-membered aromatic heterocyclic ring, an 8-10 membered condensed aromatic heterocyclic ring, a 5-7 membered unsaturated heterocyclic ring, a 4-7 membered saturated heterocyclic ring, a benzene ring, —CH=, or a cyano group (when A is a cyano group, $R^3$ and $R^{3'}$ do not exist.)

$R^3$, $R^{3'}$:

$R^3$ and $R^{3'}$ are each independently a hydrogen atom, a halogen atom, a cyano group, a hydroxy group, an oxo group, a C1-C6 alkyl group optionally substituted with the same or different one to two substituents selected from the substituent group X, a C1-C6 alkoxy group optionally substituted with the same or different one to two substituents selected from the substituent group X, a C2-C6 alkenyl group optionally substituted with the same or different one to two substituents selected from the substituent group X, a C2-C6 alkynyl group optionally substituted with the same or different one to two substituents selected from the substituent group X, a C3-C6 cycloalkyl group optionally substituted with the same or different one to two substituents selected from the substituent group X, an amino group optionally substituted with the same or different one to two substituents selected from the substituent group X, a C1-C6 alkoxycarbonyl group optionally substituted with the same or different one to two substituents selected from the substituent group X, a carbamoyl group optionally substituted with the same or different one to two substituents selected from the substituent group X, a phenyl group optionally substituted with the same or different one to two substituents selected from the substituent group X, a 5-membered aromatic heterocyclic group optionally substituted with the same or different one to two substituents selected from the substituent group X, a 6-membered aromatic heterocyclic group optionally substituted with the same or different one to two substituents selected from the substituent group X, a 5-7 membered unsaturated heterocyclic group optionally substituted with the same or different one to two substituents selected from the substituent group X, a 4-7 membered saturated heterocyclic group optionally substituted with the same or different one to two substituents selected from the substituent group X, an 8-10 membered condensed aromatic heterocyclic group optionally substituted with the same or different one to two substituents selected from the substituent group X, or $R^3$ and $R^{3'}$ may form a 5-7 membered unsaturated heterocyclic ring, a 4-7 membered saturated heterocyclic ring, or a C3-C6 cycloalkyl ring as a ring that binds to each other and condenses with A, and the ring is optionally substituted with the same or different one to two substituents selected from the substituent group X.

Substituent group X:

A halogen atom, a cyano group, a hydroxy group, an oxo group, a C1-C6 alkyl group, a hydroxy C1-C6 alkyl group, a C1-C6 alkoxy C1-C6 alkyl group, a C1-C6 haloalkyl group, a C3-C6 cycloalkyl group, a C3-C6 halocycloalkyl group, a phenyl group optionally substituted with the same or different one to two substituents selected from a substituent group Y, a 5-membered aromatic heterocyclic group optionally substituted with the same or different one to two substituents selected from the substituent group Y, a 6-membered aromatic heterocyclic group optionally substituted with the same or different one to two substituents selected from the substituent group Y, a 4-7 membered saturated heterocyclic group optionally substituted with the same or different one to two substituents selected from the substituent group Y, a C1-C6 alkoxy group, a C1-C6 haloalkoxy group, a C3-C6 cycloalkoxy group, a C3-C6 halocycloalkoxy group, a phenoxy group optionally substituted with the same or different one to two substituents selected from the substituent group Y, a 5-membered aromatic heterocyclic oxy group optionally substituted with the same or different one to two substituents selected from the substituent group Y, a 6-membered aromatic heterocyclic oxy group optionally substituted with the same or different one to two substituents selected from the substituent group Y, a 4-7 membered saturated heterocyclic oxy group optionally substituted with the same or different one to two substituents selected from the substituent group Y, a C1-C6 alkoxycarbonyl group, a C3-C6 cycloalkoxycarbonyl group, a carboxy group, a C1-C6 alkylcarbonyl group, a C3-C6 cycloalkylcarbonyl group, a phenylcarbonyl group optionally substituted with the same or different one to two substituents selected from the substituent group Y, a carbamoyl group, a mono (C1-C6 alkyl) aminocarbonyl group, a di (C1-C6 alkyl) aminocarbonyl group, a mono (C1-C6 alkyl) aminosulfonyl group, a di (C1-C6 alkyl) aminosulfonyl group, an amino group, a mono (C1-C6 alkyl) amino group, a di (C1-C6 alkyl) amino group, a C1-C6 alkoxycarbonylamino group, a mono (C1-C6 alkyl) aminocarbonylamino group, a di (C1-C6 alkyl) aminocarbonylamino group, a C1-C6 alkylcarbonylamino group, a phenylcarbonylamino group optionally substituted with the same or different one to two substituents selected from the substituent group Y, a 5-membered aromatic heterocyclic carbonylamino group optionally substituted with the same or different one to two substituents selected from the substituent group Y, a 6-membered aromatic heterocyclic carbonylamino group optionally substituted with the same or different one to two substituents selected from the substituent group Y, or a C1-C6 alkylsulfonylamino group Substituent Group Y:

A C1-C6 alkyl group, a C1-C6 alkoxy group, a halogen atom, or a hydroxy group

However, as the compound of the general formula (1) or the pharmaceutically acceptable salt thereof, a compound or a pharmaceutically acceptable salt thereof of the following general formula (Z) is excluded.

[Chemical formula 2]

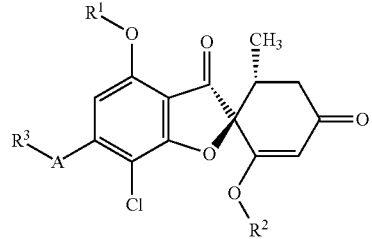

(Z)

It should be noted that the symbols in the formula for the compound of a general formula (Z) are defined as follows.

$R^1$:

A C1-C6 alkyl group or a hydroxy C1-C6 alkyl group $R^2$:

A C1-C6 alkyl group

A:

A 5-membered aromatic heterocyclic ring $R^3$:

A C1-C6 alkyl group, a hydroxy C1-C6 alkyl group, or a C1-C6 alkoxy C1-C6 alkyl group]

[2]

The compound or the pharmacologically acceptable salt thereof according to [1], wherein the 5-membered aromatic heterocyclic ring or the 5-membered aromatic heterocyclic group in A, $R^3$, or $R^{3'}$ is any one selected from the group shown below.

[Chemical formula 3]

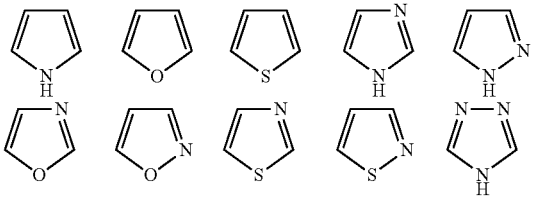

-continued

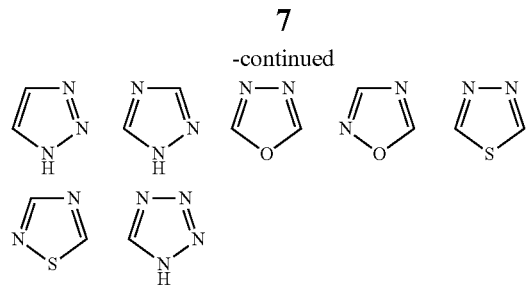

The compound or the pharmacologically acceptable salt thereof according to [1] or [2], wherein the 6-membered aromatic heterocyclic ring or the 6-membered aromatic heterocyclic group in A, $R^3$, or $R^{3'}$ is any one selected from the group shown below.

[Chemical formula 4]

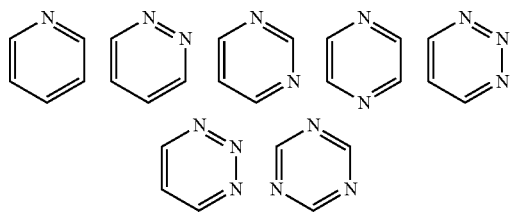

[4]

The compound or the pharmacologically acceptable salt thereof according to any one of [1] to [3], wherein the 8-10 membered condensed aromatic heterocyclic ring or the 8-10 membered condensed aromatic heterocyclic group in A, $R^3$, or $R^{3'}$ is any one selected from the group shown below.

[Chemical formula 5]

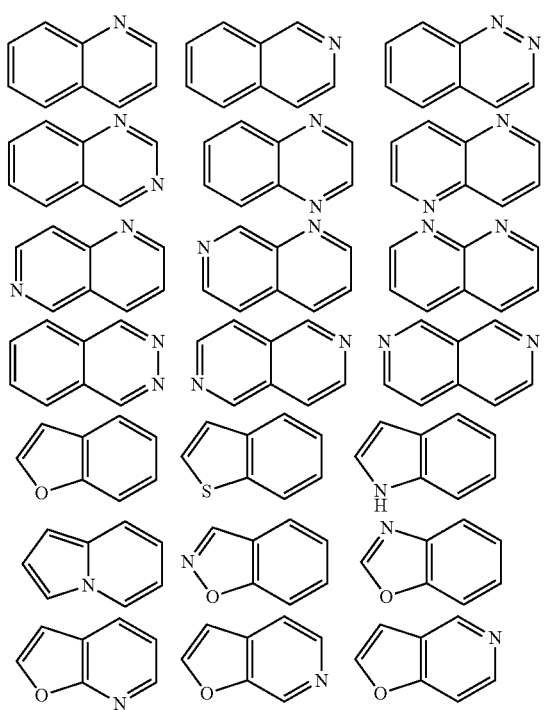

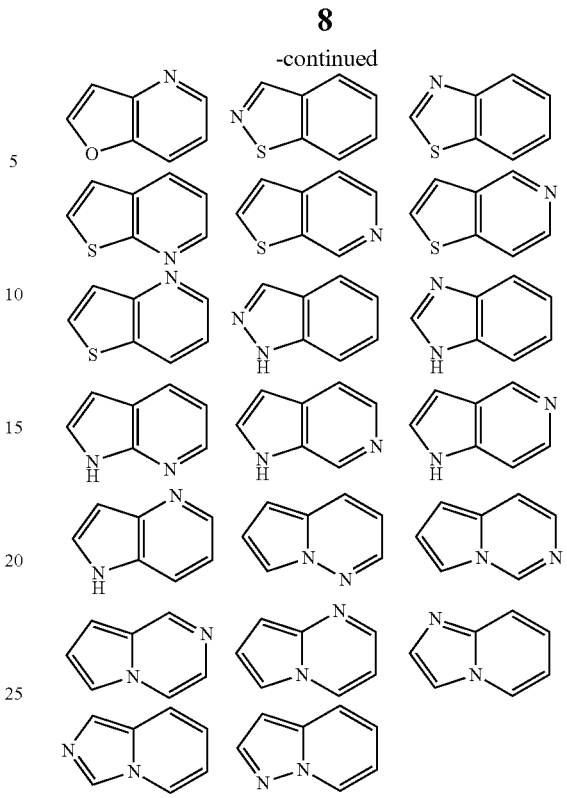

The compound or the pharmacologically acceptable salt thereof according to any one of [1] to [4] wherein the 5-7 membered unsaturated heterocyclic ring or 5-7 membered unsaturated heterocyclic group in A, $R^3$, or $R^{3'}$ is any one selected from the group shown below.

[Chemical formula 6]

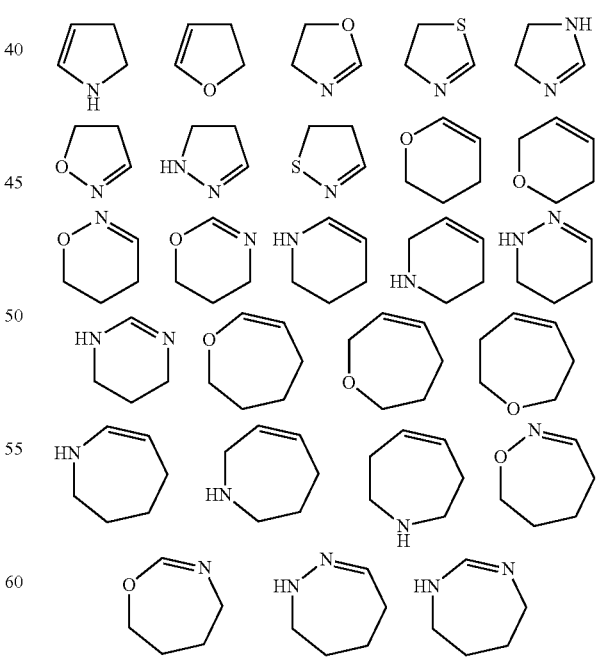

[6]

The compound or the pharmacologically acceptable salt thereof according to any one of [1] to [5] wherein the 4-7 membered saturated heterocyclic ring or the 4-7 membered saturated heterocyclic group in A, $R^1$, $R^2$, or $R^3$ is any one selected from the group shown below.

[Chemical formula 7]

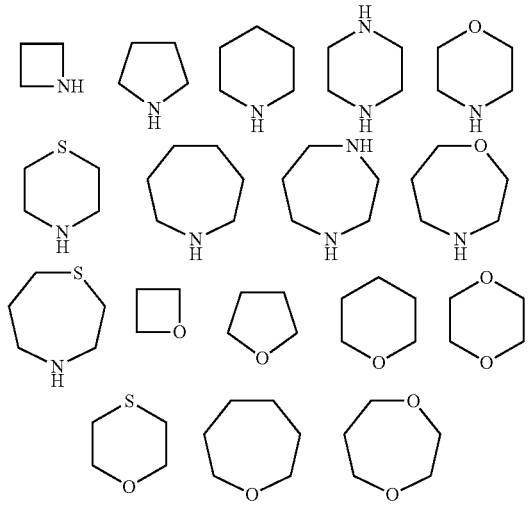

[7]
The compound or the pharmacologically acceptable salt thereof according to [1], wherein the compound of the general formula (1) is any compound selected from the following group.
(2S,5'R)-7-chloro-6-(5-ethyl-1,3,4-oxadiazol-2-yl)-3',4-dimethoxy-5'-methyl-spiro [benzofuran-2,4'-cyclohex-2-ene]-1',3-dione
(2S,5'R)-7-chloro-3',4-dimethoxy-5'-methyl-6-(5-tetrahydropyran-4-yl-1,3,4-oxadiazol-2-yl) spiro [benzofuran-2,4'-cyclohex-2-ene]-1',3-dione
(2S,5'R)-7-chloro-3',4-dimethoxy-5'-methyl-6-[5-(1-methyl-4-piperidyl)-1,3,4-oxadiazol-2-yl] spiro [benzofuran-2,4'-cyclohex-2-ene]-1',3-dione
(2S,5'R)-7-chloro-6-[5-(4-fluoro-1-methyl-4-piperidyl)-1,3,4-oxadiazol-2-yl]-3',4-dimethoxy-5'-methyl-spiro [benzofuran-2,4'-cyclohex-2-ene]-1',3-dione
(2S,5'R)-7-chloro-3',4-dimethoxy-6-[5-[(1 S)-1-methoxyethyl]-1,3,4-oxadiazol-2-yl]-5'-methyl-spiro [benzofuran-2,4'-cyclohex-2-ene]-1',3-dione
(2S,5'R)-7-chloro-4-ethoxy-3'-methoxy-5'-methyl-6-(5-methyl-1,3,4-oxadiazol-2-yl) spiro [benzofuran-2,4'-cyclohex-2-ene]-1',3-dione
(2S,5'R)-7-chloro-4-(difluoromethoxy)-3'-methoxy-5'-methyl-6-(5-methyl-1,3,4-oxadiazol-2-yl) spiro [benzofuran-2,4'-cyclohex-2-ene]-1',3-dione
(2S,5'R)-7-chloro-3',4-dimethoxy-6-[3-(1-methoxyethyl)-1,2,4-oxadiazol-5-yl]-5'-methyl-spiro [benzofuran-2,4'-cyclohex-2-ene]-1',3-dione
(2S,5'R)-7-chloro-6-[3-(1-hydroxy-1-methyl-ethyl)-1,2,4-oxadiazol-5-yl]-3',4-dimethoxy-5'-methyl-spiro [benzofuran-2,4'-cyclohex-2-ene]-1',3-dione
(2S,5'R)-7-chloro-3',4-dimethoxy-5'-methyl-6-(1H-pyrazol-5-yl) spiro [benzofuran-2,4'-cyclohex-2-ene]-1',3-dione
(2S,5'R)-7-chloro-3',4-dimethoxy-6-[1-(2-methoxyethyl) pyrazol-3-yl]-5'-methyl-spiro [benzofuran-2,4'-cyclohex-2-ene]-1',3-dione
(2S,5'R)-7-chloro-6-(1,8-dioxa-2-azaspiro [4.5] dec-2-en-3-yl)-3',4-dimethoxy-5'-methyl-spiro [benzofuran-2,4'-cyclohex-2-ene]-1',3-dione
(2S,5'R)-7-chloro-3',4-dimethoxy-5'-methyl-6-(8-methyl-1-oxa-2,8-diazaspiro [4.5] dec-2-en-3-yl) spiro [benzofuran-2,4'-cyclohex-2-ene]-1',3-dione
(2S,5'R)-7-chloro-3',4-dimethoxy-6-(2-methoxypyrimidin-5-yl)-5'-methyl-spiro [benzofuran-2,4'-cyclohex-2-ene]-1',3-dione
(2S,5'R)-7-chloro-3',4-dimethoxy-6-(6-methoxy-3-pyridyl)-5'-methyl-spiro [benzofuran-2,4'-cyclohex-2-ene]-1',3-dione
(2S,5'R)-7-chloro-3',4-dimethoxy-5'-methyl-6-(3-pyridyl) spiro [benzofuran-2,4'-cyclohex-2-ene]-1',3-dione

[8]
A pharmaceutical composition containing the compound or the pharmacologically acceptable salt thereof as an active ingredient according to any one of [1] to [7].

[9]
The pharmaceutical composition according to [8], which is for the prevention and/or treatment of a central inflammatory disease.

[10]
A pharmaceutical composition for the prevention and/or treatment of a central inflammatory disease, the pharmaceutical composition containing a compound of a general formula (1') or a pharmacologically acceptable salt thereof.

[Chemical formula 8]

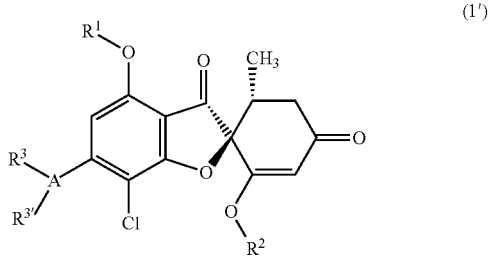

(1')

[The symbols in the formula are defined as follows.
$R^1$:
A C1-C6 alkyl group optionally substituted with the same or different one to two substituents selected from the substituent group X,
a C3-C6 cycloalkyl group optionally substituted with the same or different one to two substituents selected from the substituent group X, or
a 4-7 membered saturated heterocyclic group optionally substituted with the same or different one to two substituents selected from the substituent group X
$R^2$:
A C1-C6 alkyl group optionally substituted with the same or different one to two substituents selected from the substituent group X,
a C3-C6 cycloalkyl group optionally substituted with the same or different one to two substituents selected from the substituent group X, or
a 4-7 membered saturated heterocyclic group optionally substituted with the same or different one to two substituents selected from the substituent group X.
A:
A 5-membered aromatic heterocyclic ring,
a 6-membered aromatic heterocyclic ring,
an 8-10 membered condensed aromatic heterocyclic ring,
a 5-7 membered unsaturated heterocyclic ring,
a 4-7 membered saturated heterocyclic ring, a benzene ring, or a single bond (when it is a single bond, one or the other of $R^3$ and $R^{3'}$ is not present.)

$R^3$, $R^{3'}$:

$R^3$ and $R^{3'}$ are each independently a hydrogen atom, a halogen atom, a cyano group, a hydroxy group, a C1-C6 alkyl group optionally substituted with the same or different one to two substituents selected from the substituent group X, a C1-C6 alkoxy group optionally substituted with the same or different one to two substituents selected from the substituent group X, a C2-C6 alkenyl group optionally substituted with the same or different one to two substituents selected from the substituent group X, a C2-C6 alkynyl group optionally substituted with the same or different one to two substituents selected from the substituent group X, a C3-C6 cycloalkyl group optionally substituted with the same or different one to two substituents selected from the substituent group X, an amino group optionally substituted with the same or different one to two substituents selected from the substituent group X, a C1-C6 alkoxycarbonyl group optionally substituted with the same or different one to two substituents selected from the substituent group X, a carbamoyl group optionally substituted with the same or different one to two substituents selected from the substituent group X, a phenyl group optionally substituted with the same or different one to two substituents selected from the substituent group X, a 5-membered aromatic heterocyclic group optionally substituted with the same or different one to two substituents selected from the substituent group X, a 6-membered aromatic heterocyclic group optionally substituted with the same or different one to two substituents selected from the substituent group X, a 5-7 membered unsaturated heterocyclic group optionally substituted with the same or different one to two substituents selected from the substituent group X, a 4-7 membered saturated heterocyclic group optionally substituted with the same or different one to two substituents selected from the substituent group X, an 8-10 membered condensed aromatic heterocyclic group optionally substituted with the same or different one to two substituents selected from the substituent group X, or $R^3$ and $R^{3'}$ may form a 5-7 membered unsaturated heterocyclic ring, a 4-7 membered saturated heterocyclic ring, or a C3-C6 cycloalkyl ring as a ring that binds to each other and condenses with A, and the ring is optionally substituted with the same or different one to two substituents selected from the substituent group X.

Substituent Group X:

A halogen atom, a cyano group, a hydroxy group, an oxo group, a C1-C6 alkyl group, a hydroxy C1-C6 alkyl group, a C1-C6 alkoxy C1-C6 alkyl group, a C1-C6 haloalkyl group, a C3-C6 cycloalkyl group, a C3-C6 halocycloalkyl group, a phenyl group optionally substituted with the same or different one to two substituents selected from the substituent group Y, a 5-membered aromatic heterocyclic group optionally substituted with the same or different one to two substituents selected from the substituent group Y, a 6-membered aromatic heterocyclic group optionally substituted with the same or different one to two substituents selected from the substituent group Y, a 4-7 membered saturated heterocyclic group optionally substituted with the same or different one to two substituents selected from the substituent group Y, a C1-C6 alkoxy group, a C1-C6 haloalkoxy group, a C3-C6 cycloalkoxy group, a C3-C6 halocycloalkoxy group, a phenoxy group optionally substituted with the same or different one to two substituents selected from the substituent group Y, a 5-membered aromatic heterocyclic oxy group optionally substituted with the same or different one to two substituents selected from the substituent group Y, a 6-membered aromatic heterocyclic oxy group optionally substituted with the same or different one to two substituents selected from the substituent group Y, a 4-7 membered saturated heterocyclic oxy group optionally substituted with the same or different one to two substituents selected from the substituent group Y, a C1-C6 alkoxycarbonyl group, a C3-C6 cycloalkoxycarbonyl group, a carboxy group, a C1-C6 alkylcarbonyl group, a C3-C6 cycloalkylcarbonyl group, a phenylcarbonyl group optionally substituted with the same or different one to two substituents selected from the substituent group Y, a carbamoyl group, a mono (C1-C6 alkyl) aminocarbonyl group, a di (C1-C6 alkyl) aminocarbonyl group, a mono (C1-C6 alkyl) aminosulfonyl group, a di (C1-C6 alkyl) aminosulfonyl group, an amino group, a mono (C1-C6 alkyl) amino group, a di (C1-C6 alkyl) amino group, a C1-C6 alkoxycarbonylamino group, a mono (C1-C6 alkyl) aminocarbonylamino group, a di (C1-C6 alkyl) aminocarbonylamino group, a C1-C6 alkylcarbonylamino group, a phenylcarbonylamino group optionally substituted with the same or different one to two substituents selected from the substituent group Y, a 5-membered aromatic heterocyclic carbonylamino group optionally substituted with the same or different one to two substituents selected from the substituent group Y, a 6-membered aromatic heterocyclic carbonylamino group optionally substituted with the same or different one to two substituents selected from the substituent group Y, or a C1-C6 alkylsulfonylamino group Substituent Group Y:

A C1-C6 alkyl group, a C1-C6 alkoxy group, a halogen atom, or a hydroxy group]

[11]

The pharmaceutical composition according to [10], wherein $R^1$ is a methyl group, an ethyl group, or a hydroxyethyl group.

[12]

The pharmaceutical composition according to [10] or [11], wherein $R^2$ is a methyl group.

[13]

The pharmaceutical composition according to any one of [10] to [12], wherein the 5-membered aromatic heterocyclic ring or the 5-membered aromatic heterocyclic group in A, $R^3$, or $R^{3'}$ is any one selected from the group shown below.

[Chemical formula 9]

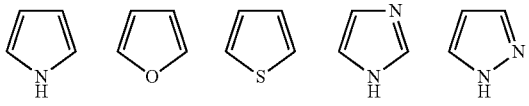

-continued

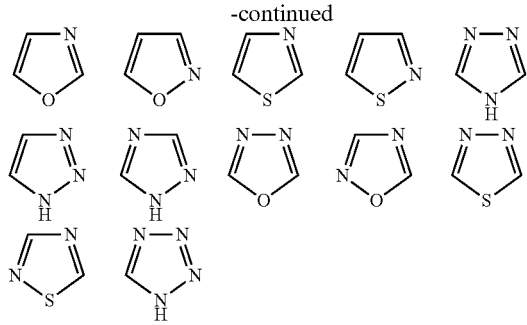

[14]

The pharmaceutical composition any one of [10] to [13], wherein the 6-membered aromatic heterocyclic ring or the 6-membered aromatic heterocyclic group in A, $R^3$, or $R^{3'}$ is any one selected from the group shown below.

[Chemical formula 10]

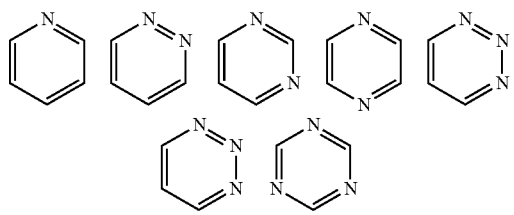

The pharmaceutical composition according to any one of [10] to [14], wherein the 5-7 membered unsaturated heterocyclic ring or the 5-7 membered unsaturated heterocyclic group in A, $R^3$, or $R^{3'}$ is any one selected from the group shown below.

[Chemical formula 11]

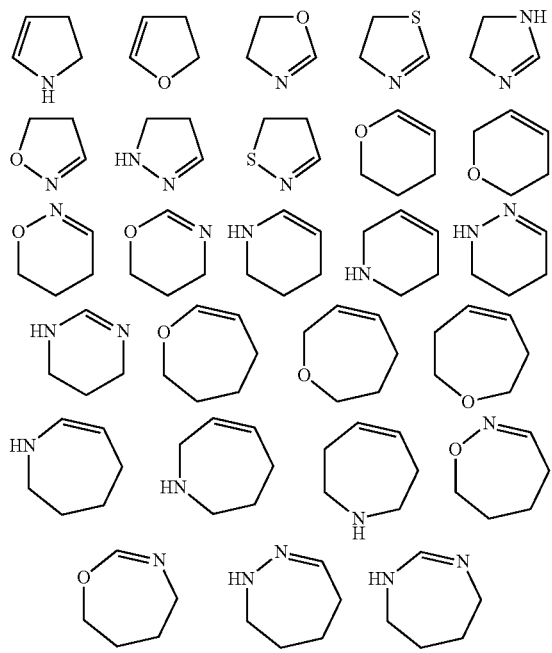

[16]

The pharmaceutical composition according to any one of [10] to [15], wherein the 4-7 membered saturated heterocyclic ring or the 4-7 membered saturated heterocyclic group in A, $R^1$, $R^2$, or $R^3$ is any one selected from the group shown below.

[Chemical formula 12]

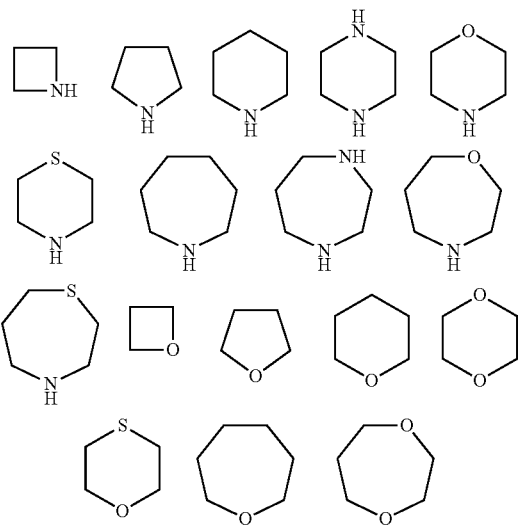

The pharmaceutical composition according to any one of [10] to [12], wherein A is a 5-membered aromatic heterocyclic ring, $R^3$ is a methyl group, an ethyl group, a hydroxy C1-C3 alkyl group, or a methoxy C1-C3 alkyl group, and $R^{3'}$ is a hydrogen atom.

[18]

The pharmaceutical composition according to any one of [10] to [12], wherein A is any ring selected from the following group, and in the case of two binding groups, $R^{3'}$ is not present.

[Chemical formula 13]

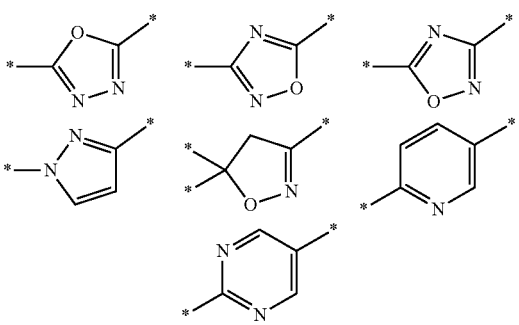

[* indicates a binding group.]

[19]

A pharmaceutical composition for the prevention and/or treatment of a central inflammatory disease, the pharmaceutical composition containing a compound of a general formula (1") or a pharmacologically acceptable salt thereof.

[Chemical formula 14]

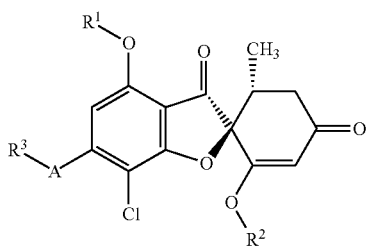

(1″)

[The symbols in the formula are defined as follows.
R¹: A methyl group or an ethyl group
R²: A methyl group
A: Any ring selected from the following group

[Chemical formula 15]

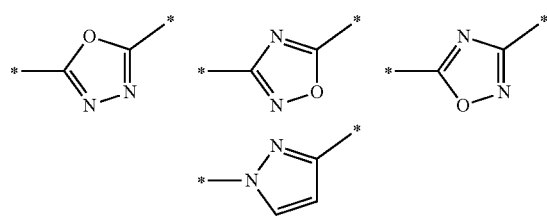

[* indicates a binding group.]
R³: A methyl group or an ethyl group]
[20]
The pharmaceutical composition according to [10], wherein the compound of the general formula (1') is any compound selected from the following group.
(2S,5'R)-7-chloro-6-(2-hydroxyethoxy)-3',4-dimethoxy-5'-methyl-spiro [benzofuran-2,4'-cyclohex-2-ene]-1',3-dione
(2S,5'R)-7-chloro-3',4-dimethoxy-6-(2-methoxyethoxy)-5'-methyl-spiro [benzofuran-2,4'-cyclohex-2-ene]-1',3-dione
(2S,5'R)-7-chloro-3',4-dimethoxy-5'-methyl-6-(1-methylpyrazol-3-yl) spiro [benzofuran-2,4'-cyclohex-2-ene]-1',3-dione
(2S,5'R)-7-chloro-6-(1-ethylpyrazol-3-yl)-3',4-dimethoxy-5'-methyl-spiro [benzofuran-2,4'-cyclohex-2-ene]-1',3-dione
(2S,5'R)-7-chloro-3',4-dimethoxy-5'-methyl-6-(5-methyl-1,3,4-oxadiazol-2-yl) spiro [benzofuran-2,4'-cyclohex-2-ene]-1',3-dione
(2S,5'R)-7-chloro-3',4-dimethoxy-5'-methyl-6-(3-methyl-1,2,4-oxadiazol-5-yl) spiro [benzofuran-2,4'-cyclohex-2-ene]-1',3-dione
(2S,5'R)-7-chloro-3',4-dimethoxy-5'-methyl-6-(5-methyl)-1,2,4-oxadiazol-3-yl) spiro [benzofuran-2,4'-cyclohex-2-ene]-1',3-dione
(2S,5'R)-7-chloro-6-[5-(1-hydroxy-1-methyl-ethyl)-1,3,4-oxadiazol-2-yl]-3',4-dimethoxy-5'-methyl-spiro [benzofuran-2,4'-cyclohex-2-ene]-1',3-dione
(2S,5'R)-7-chloro-6-[5-[(1S)-1-hydroxyethyl]-1,3,4-oxadiazol-2-yl]-3',4-dimethoxy-5'-methyl-spiro [benzofuran-2,4'-cyclohex-2-ene]-1',3-dione
(2S,5'R)-7-chloro-6-[5-[(1R)-1-hydroxyethyl]-1,3,4-oxadiazol-2-yl]-3',4-dimethoxy-5'-methyl-spiro [benzofuran-2,4'-cyclohex-2-ene]-1',3-dione
(2S,5'R)-7-chloro-4-ethoxy-6-[5-(1-hydroxy-1-methyl-ethyl)-1,3,4-oxadiazol-2-yl]-3'-methoxy-5'-methyl-spiro [benzofuran-2,4'-cyclohex-2-ene]-1',3-dione
(2S,5'R)-7-chloro-4-ethoxy-6-[5-[(1S)-1-hydroxyethyl]-1,3,4-oxadiazol-2-yl]-3'-methoxy-5'-methyl-spiro [benzofuran-2,4'-cyclohex-2-ene]-1',3-dione
(2S,5'R)-7-chloro-6-[3-(1-hydroxyethyl)-1,2,4-oxadiazol-5-yl]-3',4-dimethoxy-5'-methyl-spiro [benzofuran-2,4'-cyclohex-2-ene]-1',3-dione
(2S,5'R)-7-chloro-4-(2-hydroxyethoxy)-3'-methoxy-5'-methyl-6-(5-methyl-1,3,4-oxadiazol-2-yl) spiro [benzofuran-2,4'-cyclohex-2-ene]-1',3-dione
(2S,5'R)-7-chloro-4-(2-hydroxyethoxy)-3'-methoxy-5'-methyl-6-(3-methyl-1,2,4-oxadiazol-5-yl) spiro [benzofuran-2,4'-cyclohex-2-ene]-1',3-dione
(2S,5'R)-7-chloro-4-(2-hydroxyethoxy)-3'-methoxy-5'-methyl-6-(5-methyl-1,2,4-oxadiazol-3-yl) spiro [benzofuran-2,4'-cyclohex-2-ene]-1',3-dione
(2S,5'R)-7-chloro-6-(5-ethyl-1,3,4-oxadiazol-2-yl)-3',4-dimethoxy-5'-methyl-spiro [benzofuran-2,4'-cyclohex-2-ene]-1',3-dione
(2S,5'R)-7-chloro-3',4-dimethoxy-5'-methyl-6-(5-tetrahydropyran-4-yl-1,3,4-oxadiazol-2-yl) spiro [benzofuran-2,4'-cyclohex-2-ene]-1',3-dione
(2S,5'R)-7-chloro-3',4-dimethoxy-5'-methyl-6-[5-(1-methyl-4-piperidyl)-1,3,4-oxadiazol-2-yl] spiro [benzofuran-2,4'-cyclohex-2-ene]-1',3-dione
(2S,5'R)-7-chloro-6-[5-(4-fluoro-1-methyl-4-piperidyl)-1,3,4-oxadiazol-2-yl]-3',4-dimethoxy-5'-methyl-spiro [benzofuran-2,4'-cyclohex-2-ene]-1',3-dione
(2S,5'R)-7-chloro-3',4-dimethoxy-6-[5-[(1S)-1-methoxyethyl]-1,3,4-oxadiazol-2-yl]-5'-methyl-spiro [benzofuran-2,4'-cyclohex-2-ene]-1',3-dione
(2S,5'R)-7-chloro-4-ethoxy-3'-methoxy-5'-methyl-6-(5-methyl-1,3,4-oxadiazol-2-yl) spiro [benzofuran-2,4'-cyclohex-2-ene]-1',3-dione
(2S,5'R)-7-chloro-4-(difluoromethoxy)-3'-methoxy-5'-methyl-6-(5-methyl-1,3,4-oxadiazol-2-yl) spiro [benzofuran-2,4'-cyclohex-2-ene]-1',3-dione
(2S,5'R)-7-chloro-3',4-dimethoxy-6-[3-(1-methoxyethyl)-1,2,4-oxadiazol-5-yl]-5'-methyl-spiro [benzofuran-2,4'-cyclohex-2-ene]-1',3-dione
(2S,5'R)-7-chloro-6-[3-(1-hydroxy-1-methyl-ethyl)-1,2,4-oxadiazol-5-yl]-3',4-dimethoxy-5'-methyl-spiro [benzofuran-2,4'-cyclohex-2-ene]-1',3-dione
(2S,5'R)-7-chloro-3',4-dimethoxy-5'-methyl-6-(1H-pyrazol-5-yl) spiro [benzofuran-2,4'-cyclohex-2-ene]-1',3-dione
(2S,5'R)-7-chloro-3',4-dimethoxy-6-[1-(2-methoxyethyl)pyrazol-3-yl]-5'-methyl-spiro [benzofuran-2,4'-cyclohex-2-ene]-1',3-dione
(2S,5'R)-7-chloro-6-(1,8-dioxa-2-azaspiro [4.5] dec-2-en-3-yl)-3',4-dimethoxy-5'-methyl-spiro [benzofuran-2,4'-cyclohex-2-ene]-1',3-dione
(2S,5'R)-7-chloro-3',4-dimethoxy-5'-methyl-6-(8-methyl-1-oxa-2,8-diazaspiro [4.5] dec-2-en-3-yl) spiro [benzofuran-2,4'-cyclohex-2-ene]-1',3-dione
(2S,5'R)-7-chloro-3',4-dimethoxy-6-(2-methoxypyrimidin-5-yl)-5'-methyl-spiro [benzofuran-2,4'-cyclohex-2-ene]-1',3-dione
(2S,5'R)-7-chloro-3',4-dimethoxy-6-(6-methoxy-3-pyridyl)-5'-methyl-spiro [benzofuran-2,4'-cyclohex-2-ene]-1',3-dione
(2S,5'R)-7-chloro-3',4-dimethoxy-5'-methyl-6-(3-pyridyl) spiro [benzofuran-2,4'-cyclohex-2-ene]-1',3-dione
(2S,5'R)-7-chloro-3',4,6-trimethoxy-5'-methyl-spiro [benzofuran-2,4'-cyclohex-2-ene]-1',3-dione

[21]
A pharmaceutical composition for the prevention and/or treatment of a central inflammatory disease, the pharmaceutical composition containing a compound described below or a pharmacologically acceptable salt thereof.
(2S,5'R)-7-chloro-6-(1-ethylpyrazol-3-yl)-3',4-dimethoxy-5'-methyl-spiro [benzofuran-2,4'-cyclohex-2-ene]-1',3-dione

[22]
A pharmaceutical composition for the prevention and/or treatment of a central inflammatory disease, the pharmaceutical composition containing a compound described below or a pharmacologically acceptable salt thereof.
(2S,5'R)-7-chloro-3',4-dimethoxy-5'-methyl-6-(5-methyl-1,3,4-oxadiazol-2-yl) spiro [benzofuran-2,4'-cyclohex-2-ene]-1',3-dione

[23]
A pharmaceutical composition for the prevention and/or treatment of a central inflammatory disease, the pharmaceutical composition containing a compound described below or a pharmacologically acceptable salt thereof.
(2S,5'R)-7-chloro-6-(5-ethyl-1,3,4-oxadiazol-2-yl)-3',4-dimethoxy-5'-methyl-spiro [benzofuran-2,4'-cyclohex-2-ene]-1',3-dione

[24]
A pharmaceutical composition for the prevention and/or treatment of a central inflammatory disease, the pharmaceutical composition containing a compound described below or a pharmacologically acceptable salt thereof.
(2S,5'R)-7-chloro-6-[3-(1-hydroxy-1-methyl-ethyl)-1,2,4-oxadiazol-5-yl]-3',4-dimethoxy-5'-methyl-spiro [benzofuran-2,4'-cyclohex-2-ene]-1',3-dione

[25]
A pharmaceutical composition for the prevention and/or treatment of a central inflammatory disease, the pharmaceutical composition containing a compound described below or a pharmacologically acceptable salt thereof.
(2S,5'R)-7-chloro-4-ethoxy-3'-methoxy-5'-methyl-6-(5-methyl-1,3,4-oxadiazol-2-yl) spiro [benzofuran-2,4'-cyclohex-2-ene]-1',3-dione

[26]
The pharmaceutical composition according to any one of [9] to [25], wherein the central inflammatory disease is any one selected from a group consisting of
Alzheimer's disease, Parkinson's disease, Lewy body dementia, multiple system atrophy, Pick's disease, progressive supranuclear palsy, cerebral cortex basement degeneration, frontotemporal lobe degeneration, Huntington's disease, amyotrophic lateral sclerosis, spinal and bulbar muscular atrophy, spinal muscular atrophy, spinocerebellar degeneration, multiple sclerosis, Creutzfeldt-Jakob disease, fatal familial insomnia, Gerstmann-Straussler-Scheinker syndrome, Down syndrome, Niemann-Pick disease, cerebral amyloid angiopathy, HIV encephalopathy, influenza encephalopathy, hepatic encephalopathy, progressive multifocal leukoencephalopathy, anti-NMDA receptor antibody encephalitis, cerebrovascular disorders, traumatic brain injuries, spinal cord injuries, hypoxic encephalopathy, epilepsy, optic neuritis, congenital metabolic brain diseases, Wernicke's encephalopathy, autism spectrum disorders, attention deficit/hyperactivity disorders, tic disorders, schizophrenia, bipolar disorders, major depressive disorders (treatment resistant depression and postpartum depression), persistent depressive disorders (dysthymic disorder), premenstrual dysthymic disorders, anxiety disorders, focal phobia, panic disorders, obsessive compulsive disorders, emotional trauma and stress related disorders, eating disorders, circadian rhythm sleep/wake disorders, narcolepsy, substance related disorders (alcohol addiction and drug addiction), impulse control disorders, delirium, personality disorders, and Rett's syndrome.

[27]
The pharmaceutical composition according to any one of [9] to [25], wherein the central inflammatory disease is any one selected from a group consisting of
Alzheimer's disease, Parkinson's disease, Lewy body dementia, multiple system atrophy, Pick's disease, progressive supranuclear palsy, cerebral cortex basement degeneration, frontotemporal lobe degeneration, Huntington's disease, amyotrophic lateral sclerosis, spinal and bulbar muscular atrophy, spinal muscular atrophy, spinocerebellar degeneration, multiple sclerosis, Creutzfeldt-Jakob disease, schizophrenia, bipolar disorders, major depressive disorders (treatment resistant depression and postpartum depression), persistent depressive disorders (dysthymic disorder), premenstrual dysthymic disorders, anxiety disorders, focal phobia, panic disorders, obsessive compulsive disorders, emotional trauma and stress related disorders, eating disorders, circadian rhythm sleep/wake disorders, narcolepsy, substance related disorders (alcohol addiction and drug addiction), impulse control disorders, delirium, personality disorders, and Rett's syndrome

[28]
The pharmaceutical composition according to any one of [9] to [25], wherein the central inflammatory disease is any one selected from a group consisting of schizophrenia, bipolar disorders, major depressive disorders (treatment resistant depression and postpartum depression), persistent depressive disorders (dysthymic disorder), premenstrual dysthymic disorders, anxiety disorders, focal phobia, panic disorders, and obsessive compulsive disorders.

[29]
A crystal of (2S,5'R)-7-chloro-6-(1-ethylpyrazol-3-yl)-3',4-dimethoxy-5'-methyl-spiro [benzofuran-2,4'-cyclohex-2-ene]-1',3-dione (example 4) having peaks at about 9.5, 10.7, 14.1, 16.4, 17.9, 23.3, 23.6, 23.9, 24.4, and 27.2 as diffraction angles (2θ (°)) in powder X-ray diffraction.

[30]
A crystal of (2S,5'R)-7-chloro-6-(1-ethylpyrazol-3-yl)-3',4-dimethoxy-5'-methyl-spiro [benzofuran-2,4'-cyclohex-2-ene]-1',3-dione (example 4) having the X-ray diffraction pattern shown in FIG. 1.

[31]
A crystal of (2S,5'R)-7-chloro-3',4-dimethoxy-5'-methyl-6-(5-methyl-1,3,4-oxadiazol-2-yl) spiro [benzofuran-2,4'-cyclohex-2-ene]-1',3-dione (example 5) having peaks at about 10.0, 12.3, 15.6, 18.3, 19.1, 20.7, 22.3, 22.9, 24.2, and 29.3 as diffraction angles (2θ (°)) in powder X-ray diffraction.

[32]
A crystal of (2S,5'R)-7-chloro-3',4-dimethoxy-5'-methyl-6-(5-methyl-1,3,4-oxadiazol-2-yl) spiro [benzofuran-2,4'-cyclohex-2-ene]-1',3-dione (example 5) having the X-ray diffraction pattern shown in FIG. 2.

[33]
A crystal of (2S,5'R)-7-chloro-6-(5-ethyl-1,3,4-oxadiazol-2-yl)-3',4-dimethoxy-5'-methyl-spiro [benzofuran-2,4'-cyclohex-2-ene]-1',3-dione (example 17) having peaks at about 6.4, 11.2, 11.6, 12.7, 14.7, 17.0, 19.6, 22.4, 24.1, and 26.0 as diffraction angles (2θ (°)) in powder X-ray diffraction.

[34]
A crystal of (2S,5'R)-7-chloro-6-(5-ethyl-1,3,4-oxadiazol-2-yl)-3',4-dimethoxy-5'-methyl-spiro [benzofuran-2,4'- cyclohex-2-ene]-1',3-dione (example 17) having the X-ray diffraction pattern shown in FIG. 3.

[35]
A crystal of (2S,5'R)-7-chloro-6-[3-(1-hydroxy-1-methyl-ethyl)-1,2,4-oxadiazol-5-yl]-3',4-dimethoxy-5'-methyl-spiro[benzofuran-2,4'-cyclohex-2-ene]-1',3-dione (example 25) having peaks at about 8.1, 11.5, 13.2, 13.5, 14.0, 14.4, 20.8, 21.4, 22.3, and 25.3 as diffraction angles (2θ (°)) in powder X-ray diffraction.

[36]
A crystal of (2S,5'R)-7-chloro-6-[3-(1-hydroxy-1-methyl-ethyl)-1,2,4-oxadiazol-5-yl]-3',4-dimethoxy-'-methyl-spiro[benzofuran-2,4'-cyclohex-2-ene]-1',3-dione (example 25) having the X-ray diffraction pattern shown in FIG. 4.

Effect of the Invention

The compound having a specific chemical structure having a central anti-inflammatory effect or a pharmacologically acceptable salt thereof of the present invention has various properties different from anti-inflammatory agents existing to date, so it is considered to be useful as a novel pharmaceutical.

In addition, the compound and the pharmacologically acceptable salt thereof of the present invention have excellent properties in terms of anti-inflammatory activity, bioavailability, in vitro activity, in vivo activity, rapid effects of the drug, sustained drug effect, physical stability, drug interaction, toxicity, and the like, and are useful as pharmaceuticals.

BRIEF DESCRIPTION OF THE DRAWINGS

FIG. 1 shows a powder X-ray diffraction pattern of the compound of example 4. The ordinate represents intensity (cps) and the abscissa represents a diffraction angle (2θ (°)).

FIG. 2 shows a powder X-ray diffraction pattern of the compound of example 5. The ordinate represents intensity (cps) and the abscissa represents a diffraction angle (2θ (°)).

FIG. 3 shows a powder X-ray diffraction pattern of the compound of example 17. The ordinate represents intensity (cps) and the abscissa represents a diffraction angle (2θ (°)).

FIG. 4 shows a powder X-ray diffraction pattern of the compound of example 25. The ordinate represents intensity (cps) and the abscissa represents a diffraction angle (2θ (°)).

EMBODIMENTS

The present invention will be described in detail below.
(Substituents, Explanation of Terms, and the Like)
An aspect of the present invention includes the compound of the general formula (1) or the pharmacologically acceptable salt thereof.

[Chemical formula 16]

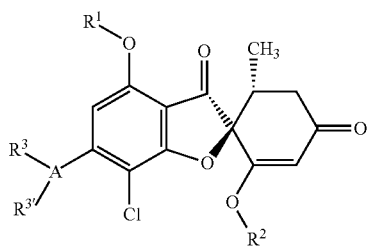

(1)

[The symbols in the formula are defined as follows.
$R^1$:
A C1-C6 alkyl group optionally substituted with the same or different one to two substituents selected from the substituent group X,
a C3-C6 cycloalkyl group optionally substituted with the same or different one to two substituents selected from the substituent group X, or
a 4-7 membered saturated heterocyclic group optionally substituted with the same or different one to two substituents selected from the substituent group X
$R^2$:
A C1-C6 alkyl group optionally substituted with the same or different one to two substituents selected from the substituent group X,
a C3-C6 cycloalkyl group optionally substituted with the same or different one to two substituents selected from the substituent group X, or
a 4-7 membered saturated heterocyclic group optionally substituted with the same or different one to two substituents selected from the substituent group X
A:
A 5-membered aromatic heterocyclic ring,
a 6-membered aromatic heterocyclic ring,
an 8-10 membered condensed aromatic heterocyclic ring,
a 5-7 membered unsaturated heterocyclic ring,
a 4-7 membered saturated heterocyclic ring,
a benzene ring, —CH=, or a cyano group (when A is a cyano group, $R^3$ and $R^{3'}$ do not exist)
$R^3$, $R^{3'}$:
$R^3$ and $R^{3'}$ are each independently a hydrogen atom, a halogen atom, a cyano group, a hydroxy group, an oxo group,
a C1-C6 alkyl group optionally substituted with the same or different one to two substituents selected from the substituent group X,
a C1-C6 alkoxy group optionally substituted with the same or different one to two substituents selected from the substituent group X,
a C2-C6 alkenyl group optionally substituted with the same or different one to two substituents selected from the substituent group X,
a C2-C6 alkynyl group optionally substituted with the same or different one to two substituents selected from the substituent group X,
a C3-C6 cycloalkyl group optionally substituted with the same or different one to two substituents selected from the substituent group X,
an amino group optionally substituted with the same or different one to two substituents selected from the substituent group X,
a C1-C6 alkoxycarbonyl group optionally substituted with the same or different one to two substituents selected from the substituent group X,
a carbamoyl group optionally substituted with the same or different one to two substituents selected from the substituent group X,
a phenyl group optionally substituted with the same or different one to two substituents selected from the substituent group X,
a 5-membered aromatic heterocyclic group optionally substituted with the same or different one to two substituents selected from the substituent group X,
a 6-membered aromatic heterocyclic group optionally substituted with the same or different one to two substituents selected from the substituent group X, a 5-7 membered unsaturated heterocyclic group optionally substituted with the same or different one to two substituents selected from the substituent group X,
a 4-7 membered saturated heterocyclic group optionally substituted with the same or different one to two substituents selected from the substituent group X,
an 8-10 membered condensed aromatic heterocyclic group optionally substituted with the same or different one to two substituents selected from the substituent group X, or
$R^3$ and $R^{3'}$ may form a 5-7 membered unsaturated heterocyclic ring, a 4-7 membered saturated heterocyclic ring, or a C3-C6 cycloalkyl ring as a ring that binds to each other and condenses with A, and the ring is optionally substituted with the same or different one to two substituents selected from the substituent group X.
It should be noted that the ring formed by $R^3$ and $R^{3'}$ binding to each other and condensing with A includes a spiro ring.
Substituent Group X:
A halogen atom, a cyano group, a hydroxy group, an oxo group, a C1-C6 alkyl group, a hydroxy C1-C6 alkyl group, a C1-C6 alkoxy C1-C6 alkyl group, a C1-C6 haloalkyl group, a C3-C6 cycloalkyl group, a C3-C6 halocycloalkyl group,
a phenyl group optionally substituted with the same or different one to two substituents selected from the substituent group Y,
a 5-membered aromatic heterocyclic group optionally substituted with the same or different one to two substituents selected from the substituent group Y,
a 6-membered aromatic heterocyclic group optionally substituted with the same or different one to two substituents selected from the substituent group Y,
a 4-7 membered saturated heterocyclic group optionally substituted with the same or different one to two substituents selected from the substituent group Y,
a C1-C6 alkoxy group, a C1-C6 haloalkoxy group, a C3-C6 cycloalkoxy group, a C3-C6 halocycloalkoxy group,
a phenoxy group optionally substituted with the same or different one to two substituents selected from the substituent group Y,
a 5-membered aromatic heterocyclic oxy group optionally substituted with the same or different one to two substituents selected from the substituent group Y,
a 6-membered aromatic heterocyclic oxy group optionally substituted with the same or different one to two substituents selected from the substituent group Y,
a 4-7 membered saturated heterocyclic oxy group optionally substituted with the same or different one to two substituents selected from the substituent group Y,
a C1-C6 alkoxycarbonyl group, a C3-C6 cycloalkoxycarbonyl group, a carboxy group, a C1-C6 alkylcarbonyl group, a C3-C6 cycloalkylcarbonyl group,
a phenylcarbonyl group optionally substituted with the same or different one to two substituents selected from the substituent group Y,
a carbamoyl group, a mono (C1-C6 alkyl) aminocarbonyl group, a di (C1-C6 alkyl) aminocarbonyl group, a mono (C1-C6 alkyl) aminosulfonyl group, a di (C1-C6 alkyl) aminosulfonyl group, an amino group, a mono (C1-C6 alkyl) amino group, a di (C1-C6 alkyl) amino group, a C1-C6 alkoxycarbonylamino group, a mono (C1-C6 alkyl) aminocarbonylamino group, a di (C1-C6 alkyl) aminocarbonylamino group, a C1-C6 alkylcarbonylamino group,
a phenylcarbonylamino group optionally substituted with the same or different one to two substituents selected from the substituent group Y,
a 5-membered aromatic heterocyclic carbonylamino group optionally substituted with the same or different one to two substituents selected from the substituent group Y,
a 6-membered aromatic heterocyclic carbonylamino group optionally substituted with the same or different one to two substituents selected from the substituent group Y, or
a C1-C6 alkylsulfonylamino group
Substituent Group Y:
A C1-C6 alkyl group, a C1-C6 alkoxy group, a halogen atom, or a hydroxy group
However, as the compound of the general formula (1) or the pharmaceutically acceptable salt thereof, a compound or a pharmaceutically acceptable salt thereof of the following general formula (Z) is excluded.

[Chemical formula 17]

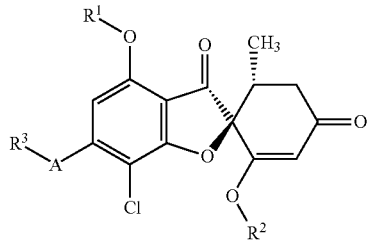

(Z)

It should be noted that the symbols in the formula for the compound of the general formula (Z) are defined as follows.
$R^1$:
A C1-C6 alkyl group or a hydroxy C1-C6 alkyl group
$R^2$:
A C1-C6 alkyl group
A:
A 5-membered aromatic heterocyclic ring
$R^3$:
A C1-C6 alkyl group, a hydroxy C1-C6 alkyl group, or a C1-C6 alkoxy C1-C6 alkyl group]
In addition, an aspect of the present invention includes the pharmaceutical composition for the prevention and/or treatment of a central inflammatory disease, which contains the compound of the general formula (1') or the pharmacologically acceptable salt thereof.

[Chemical formula 18]

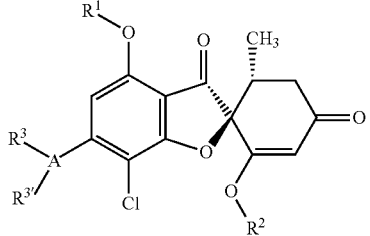

(1')

[The symbols in the formula are defined as follows.
$R^1$:
A C1-C6 alkyl group optionally substituted with the same or different one to two substituents selected from the substituent group X,
a C3-C6 cycloalkyl group optionally substituted with the same or different one to two substituents selected from the substituent group X, or a 4-7 membered saturated heterocyclic group optionally substituted with the same or different one to two substituents selected from the substituent group X.

$R^2$:

A C1-C6 alkyl group optionally substituted with the same or different one to two substituents selected from the substituent group X, a C3-C6 cycloalkyl group optionally substituted with the same or different one to two substituents selected from the substituent group X, or a 4-7 membered saturated heterocyclic group optionally substituted with the same or different one to two substituents selected from the substituent group X.

A:

A 5-membered aromatic heterocyclic ring, a 6-membered aromatic heterocyclic ring, an 8-10 membered condensed aromatic heterocyclic ring, a 5-7 membered unsaturated heterocyclic ring, a 4-7 membered saturated heterocyclic ring, a benzene ring, or a single bond (when it is a single bond, one or the other of $R^3$ and $R^{3'}$ is not present.)

$R^3$, $R^{3'}$:

$R^3$ and $R^{3'}$ are each independently a hydrogen atom, a halogen atom, a cyano group, a hydroxy group, a C1-C6 alkyl group optionally substituted with the same or different one to two substituents selected from the substituent group X, a C1-C6 alkoxy group optionally substituted with the same or different one to two substituents selected from the substituent group X, a C2-C6 alkenyl group optionally substituted with the same or different one to two substituents selected from the substituent group X, a C2-C6 alkynyl group optionally substituted with the same or different one to two substituents selected from the substituent group X, a C3-C6 cycloalkyl group optionally substituted with the same or different one to two substituents selected from the substituent group X, an amino group optionally substituted with the same or different one to two substituents selected from the substituent group X, a C1-C6 alkoxycarbonyl group optionally substituted with the same or different one to two substituents selected from the substituent group X, a carbamoyl group optionally substituted with the same or different one to two substituents selected from the substituent group X, a phenyl group optionally substituted with the same or different one to two substituents selected from the substituent group X, a 5-membered aromatic heterocyclic group optionally substituted with the same or different one to two substituents selected from the substituent group X, a 6-membered aromatic heterocyclic group optionally substituted with the same or different one to two substituents selected from the substituent group X, a 5-7 membered unsaturated heterocyclic group optionally substituted with the same or different one to two substituents selected from the substituent group X, a 4-7 membered saturated heterocyclic group optionally substituted with the same or different one to two substituents selected from the substituent group X, an 8-10 membered condensed aromatic heterocyclic group optionally substituted with the same or different one to two substituents selected from the substituent group X, or $R^3$ and $R^{3'}$ may form a 5-7 membered unsaturated heterocyclic ring, a 4-7 membered saturated heterocyclic ring, or a C3-C6 cycloalkyl ring as a ring that binds to each other and condenses with A, and the ring is optionally substituted with the same or different one to two substituents selected from the substituent group X.

It should be noted that the ring formed by $R^3$ and $R^{3'}$ binding to each other and condensing with A includes a spiro ring.

Substituent Group X:

A halogen atom, a cyano group, a hydroxy group, an oxo group, a C1-C6 alkyl group, a hydroxy C1-C6 alkyl group, a C1-C6 alkoxy C1-C6 alkyl group, a C1-C6 haloalkyl group, a C3-C6 cycloalkyl group, a C3-C6 halocycloalkyl group, a phenyl group optionally substituted with the same or different one to two substituents selected from the substituent group Y, a 5-membered aromatic heterocyclic group optionally substituted with the same or different one to two substituents selected from the substituent group Y, a 6-membered aromatic heterocyclic group optionally substituted with the same or different one to two substituents selected from the substituent group Y, a 4-7 membered saturated heterocyclic group optionally substituted with the same or different one to two substituents selected from the substituent group Y, a C1-C6 alkoxy group, a C1-C6 haloalkoxy group, a C3-C6 cycloalkoxy group, a C3-C6 halocycloalkoxy group, a phenoxy group optionally substituted with the same or different one to two substituents selected from the substituent group Y, a 5-membered aromatic heterocyclic oxy group optionally substituted with the same or different one to two substituents selected from the substituent group Y, a 6-membered aromatic heterocyclic oxy group optionally substituted with the same or different one to two substituents selected from the substituent group Y, a 4-7 membered saturated heterocyclic oxy group optionally substituted with the same or different one to two substituents selected from the substituent group Y, a C1-C6 alkoxycarbonyl group, a C3-C6 cycloalkoxycarbonyl group, a carboxy group, a C1-C6 alkylcarbonyl group, a C3-C6 cycloalkylcarbonyl group, a phenylcarbonyl group optionally substituted with the same or different one to two substituents selected from the substituent group Y, a carbamoyl group, a mono (C1-C6 alkyl) aminocarbonyl group, a di (C1-C6 alkyl) aminocarbonyl group, a mono (C1-C6 alkyl) aminosulfonyl group, a di (C1-C6 alkyl) aminosulfonyl group, an amino group, a mono (C1-C6 alkyl) amino group, a di (C1-C6 alkyl) amino group, a C1-C6 alkoxycarbonylamino group, a mono (C1-C6 alkyl) aminocarbonylamino group, a di (C1-C6 alkyl) aminocarbonylamino group, a C1-C6 alkylcarbonylamino group, a phenylcarbonylamino group optionally substituted with the same or different one to two substituents selected from the substituent group Y, a 5-membered aromatic heterocyclic carbonylamino group optionally substituted with the same or different one to two substituents selected from the substituent group Y, a 6-membered aromatic heterocyclic carbonylamino group optionally substituted with the same or different one to two substituents selected from the substituent group Y, or
a C1-C6 alkylsulfonylamino group
Substituent Group Y:
A C1-C6 alkyl group, a C1-C6 alkoxy group, a halogen atom, or a hydroxy group]

A further aspect of the present invention includes a substituent of the compound of the general formula (1') in the pharmaceutical composition for prevention and/or treatment of a central inflammatory disease, the pharmaceutical composition containing the compound of the general formula (1') or the pharmacologically acceptable salt thereof and is a case described below.

The 5-membered aromatic heterocyclic ring for A is the same as described above, but more preferably, it represents the following 5-membered ring. (It should be noted that in this case, $R_{3'}$ is not present.)

[Chemical formula 19]

[* indicates a binding group.]

The 5-membered aromatic heterocyclic ring forms the following compound as the compound of the general formula (1') depending on the binding group.

[Chemical formula 20]

[In the formula, $R^1$, $R^2$, and $R^3$ have the same meaning as in the case of the compound of the above general formula (1').]

In the present specification, the "5-membered aromatic heterocyclic ring" is a monocyclic 5-membered aromatic heterocyclic ring containing one to four atoms selected from the group consisting of a nitrogen atom, an oxygen atom, and a sulfur atom. For example, rings such as those shown below are included.

[Chemical formula 21]

In the present specification, the "6-membered aromatic heterocyclic ring" is a monocyclic 6-membered aromatic heterocyclic ring containing one to four atoms selected from the group consisting of a nitrogen atom, an oxygen atom, and a sulfur atom. For example, rings such as those shown below are included.

[Chemical formula 22]

In the present specification, the "8-10 membered condensed aromatic heterocyclic ring" is an 8-10 membered condensed aromatic heterocyclic ring containing one to four atoms selected from the group consisting of a nitrogen atom, an oxygen atom, and a sulfur atom. For example, rings such as those shown below are included.

[Chemical formula 23]

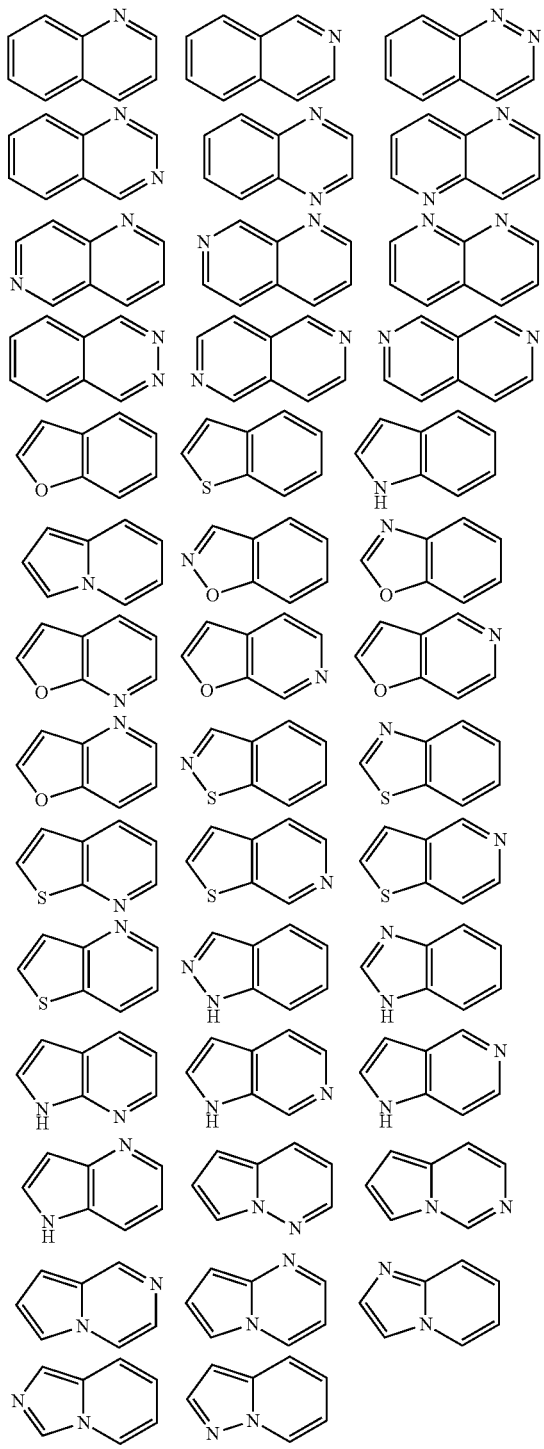

In the present specification, the "5-7 membered unsaturated heterocyclic ring" is a ring in which a monocyclic 5-7 membered saturated heterocyclic ring is partially oxidized or a ring in which an aromatic heterocyclic ring is partially reduced containing one to four atoms selected from the group consisting of a nitrogen atom, an oxygen atom, and a sulfur atom. For example, rings such as those shown below are included.

[Chemical formula 24]

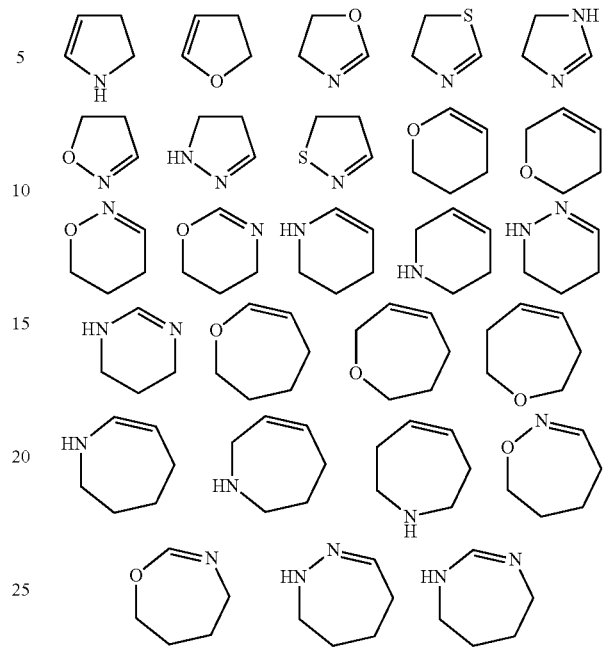

In the present specification, the "4-7 membered saturated heterocyclic ring" is a monocyclic 4-7 membered saturated heterocyclic ring containing one to four atoms selected from the group consisting of a nitrogen atom, an oxygen atom, and a sulfur atom. For example, rings such as those shown below are included as monocyclic 4-7 membered saturated heterocyclic rings.

[Chemical formula 25]

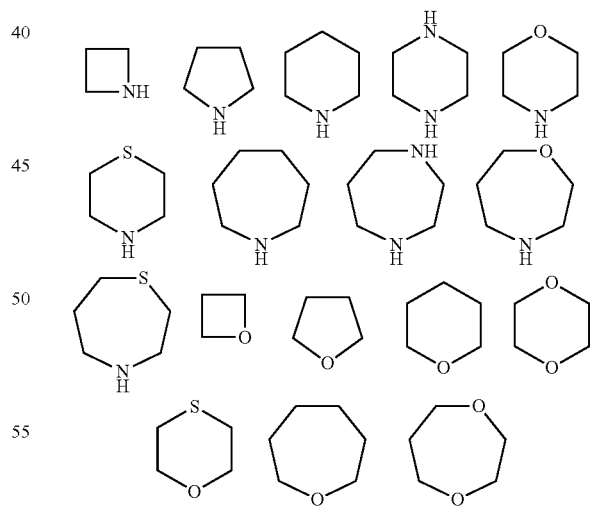

The "halogen atom" in the present specification is a fluorine atom, a chlorine atom, a bromine atom, or an iodine atom, and it is preferably a fluorine atom or a chlorine atom.

The "C1-C6 alkyl group" in the present specification is a linear or branched alkyl group having one to six carbon atoms. Examples thereof include a methyl group, an ethyl group, a 1-propyl group, an isopropyl group, a 1-butyl group, a 2-butyl group, a 2-methyl-1-propyl group, a 2-methyl-2-propyl group, a 1-pentyl group, a 2-pentyl group, a 3-pentyl group, a 2-methyl-2-butyl group, a 3-methyl-2-butyl group, a 1-hexyl group, a 2-hexyl group, a 3-hexyl group, a 2-methyl-1-pentyl group, a 3-methyl-1-pentyl group, a 2-ethyl-1-butyl group, a 2,2-dimethyl-1-butyl group, and a 2,3-dimethyl-1-butyl group, and it is preferably a methyl group or an ethyl group.

The "C2-C6 alkenyl group" in the present specification is a linear or branched alkenyl group having two to six carbon atoms, and it may have one or two or more carbon-carbon double bonds. For example, it is a vinyl group, a 2-propenyl (allyl) group, a 2-butenyl group, a 2-pentenyl group, a 3-methyl-2-butenyl group, a 2-hexenyl group, or a 3-methyl-2-pentenyl group, and preferably, it is a vinyl group or an allyl group.

The "C2-C6 alkynyl group" in the present specification is a linear or branched alkynyl group having two to six carbon atoms, and it may have one or two or more carbon-carbon triple bonds. For example, it is an ethynyl group, a 1-propynyl group, a 2-propynyl group, a 1-butynyl group, a 2-butynyl group, a 1-pentynyl group, a 2-pentynyl group, or 1-hexynyl group, and it is preferably an ethynyl group or a 1-propynyl group.

The "C1-C6 alkoxy group" in the present specification is a group in which an oxygen atom is bonded to a C1-C6 alkyl group. Examples thereof include a methoxy group, an ethoxy group, a 1-propoxy group, a 2-propoxy group, a 1-butoxy group, a 2-butoxy group, a 2-methyl-1-propoxy group, a 2-methyl-2-propoxy group, a 1-pentyloxy group, a 2-pentyloxy group, a 3-pentyloxy group, a 2-methyl-2-butoxy group, a 3-methyl-2-butoxy group, a 1-hexyloxy group, a 2-hexyloxy group, a 3-hexyloxy group, a 2-methyl-1-pentyloxy group, and a 3-methyl-1-pentyloxy group. Preferably, it is a methoxy group, an ethoxy group, a 1-propoxy group, or a 2-propoxy group.

The "C3-C6 cycloalkyl group" in the present specification is a cyclic alkyl group having three to six carbon atoms, and it is preferably a cyclopropyl group, a cyclobutyl group, a cyclopentyl group, or a cyclohexyl group.

The "hydroxy C1-C6 alkyl group" in the present specification is a group in which a hydroxyl group is bonded to a C1-C6 alkyl group. For example, it is a hydroxymethyl group or a hydroxyethyl group.

The "C1-C6 alkoxy C1-C6 alkyl group" in the present specification is a group in which a C1-C6 alkoxy is bonded to a C1-C6 alkyl group. Examples thereof include a methoxymethyl group, a methoxyethyl group, an ethoxymethyl group, and an ethoxyethyl group.

The "C1-C6 haloalkyl group" in the present specification is a group in which a halogen atom is bonded to a C1-C6 alkyl group. Examples thereof include a fluoromethyl group, a difluoromethyl group, a dichloromethyl group, a dibromomethyl group, a trifluoromethyl group, a trichloromethyl group, a 2-fluoroethyl group, a 2-bromoethyl group, a 2-chloroethyl group, a 2-iodoethyl group, a 2,2-difluoroethyl group, a 2,2,2-trifluoroethyl group, a trichloroethyl group, a pentafluoroethyl group, a 3-fluoropropyl group, a 3-chloropropyl group, and a 4-fluorobutyl group. It is preferably a trifluoromethyl group.

The "C3-C6 halocycloalkyl group" in the present specification is a group in which a halogen atom is bonded to a C3-C6 cycloalkyl group, and examples thereof include a fluorocyclopropyl group, a fluorocyclobutyl group, a fluorocyclopentyl group, and a fluorocyclohexyl group.

The "C1-C6 haloalkoxy group" in the present specification is a group in which a halogen atom is bonded to a C1-C6 alkoxy group, and examples thereof include a fluoromethoxy group, a difluoromethoxy group, a dichloromethoxy group, a dibromomethoxy group, a trifluoromethoxy group, a trichloromethoxy group, a 2-fluoroethoxy group, a 2-bromoethoxy group, a 2-chloroethoxy group, a 2-iodoethoxy group, a 2,2-difluoroethoxy group, a 2,2,2-trifluoroethoxy group, a trichloroethoxy group, a pentafluoroethoxy group, a 3-fluoropropoxy group, a 3-chloropropoxy group, and a 4-fluorobutoxy group. It is preferably a trifluoromethoxy group.

The "C3-C6 cycloalkoxy group" in the present specification is a group in which a C3-C6 cycloalkyl group is bonded to an oxygen atom, and it is preferably a cyclopropyloxy group, a cyclobutyloxy group, a cyclopentyloxy group, or a cyclohexyloxy group.

The "C3-C6 halocycloalkoxy group" in the present specification is a group in which a C3-C6 halocycloalkyl group is bonded to an oxygen atom, and examples thereof include a fluorocyclopropoxy group, a fluorocyclobutoxy group, a fluorocyclopentyloxy group, and a fluorocyclohexyloxy group.

The "5-membered aromatic heterocyclic oxy group" in the present specification is a group in which a 5-membered aromatic heterocyclic ring is bonded to an oxygen atom.

The "6-membered aromatic heterocyclic oxy group" in the present specification is a group in which a 6-membered aromatic heterocyclic ring is bonded to an oxygen atom.

The "4-7 membered saturated heterocyclic oxy group" in the present specification is a group in which a 4-7 membered saturated heterocyclic ring is bonded to an oxygen atom.

The "C1-C6 alkoxycarbonyl group" in the present specification is a group in which a C1-C6 alkoxy group is bonded to a carbonyl group, and examples thereof include a methoxycarbonyl group, an ethoxycarbonyl group, and a propoxycarbonyl group.

The "C3-C6 cycloalkoxycarbonyl group" in the present specification is a group in which a C3-C6 cycloalkoxy group is bonded to a carbonyl group, and it is preferably a cyclopropyloxycarbonyl group, a cyclobutyloxycarbonyl group, a cyclopentyloxycarbonyl group, or a cyclohexyloxycarbonyl group.

The "C1-C6 alkyl carbonyl group" in the present specification is a group in which a C1-C6 alkyl group is bonded to a carbonyl group, and examples thereof include a methyl carbonyl group, an ethyl carbonyl group, or a propyl carbonyl group.

The "mono (C1-C6 alkyl) aminocarbonyl group" in the present specification is a group in which one C1-C6 alkyl group is bonded to the amino group of an aminocarbonyl group, and it is preferably a methylaminocarbonyl group, an ethylaminocarbonyl group, or a propylaminocarbonyl group.

The "di (C1-C6 alkyl) aminocarbonyl group" in the present specification is a group in which two C1-C6 alkyl groups are bonded to the amino group of an aminocarbonyl group, and it is preferably a dimethylaminocarbonyl group, a diethylaminocarbonyl group, or a dipropylaminocarbonyl group.

The "mono (C1-C6 alkyl) aminosulfonyl group" in the present specification is a group in which one C1-C6 alkyl group is bonded to the amino group of an aminosulfonyl group, and it is preferably a methylaminosulfonyl group, an ethylaminosulfonyl group, or a propylaminosulfonyl group.

The "di (C1-C6 alkyl) aminosulfonyl group" in the present specification is a group in which two C1-C6 alkyl groups are bonded to the amino group of the aminosulfonyl group, and it is preferably a dimethylaminosulfonyl group, a diethylaminosulfonyl group, or a dipropylaminosulfonyl group.

The "mono (C1-C6 alkyl) amino group" in the present specification is a group in which one C1-C6 alkyl group is bonded to an amino group, and it is preferably a methylamino group, an ethylamino group, or a propylamino group.

The "di (C1-C6 alkyl) amino group" in the present specification is a group in which two C1-C6 alkyl groups are bonded to an amino group, and it is preferably a dimethylamino group, a diethylamino group, or a dipropyl amino group.

The "C1-C6 alkoxycarbonylamino group" in the present specification is a group in which a C1-C6 alkoxycarbonyl group is bonded to an amino group, and for example, it is a methoxycarbonylamino group, an ethoxycarbonylamino group, or a propoxycarbonylamino group.

The "mono (C1-C6 alkyl) aminocarbonylamino group" in the present specification is a group in which a mono (C1-C6 alkyl) aminocarbonyl group is bonded to an amino group, and it is preferably a methylaminocarbonylamino group, an ethylaminocarbonylamino group, or a propylaminocarbonylamino group.

The "di (C1-C6 alkyl) aminocarbonylamino group" in the present specification is a group in which a di (C1-C6 alkyl) aminocarbonyl group is bonded to an amino group, and it is preferably a dimethylaminocarbonylamino group, a diethylaminocarbonylamino group, or a dipropylaminocarbonylamino group.

The "5-membered aromatic heterocyclic carbonylamino group" in the present specification is a group in which a 5-membered aromatic heterocyclic carbonyl group is bonded to an amino group.

The "6-membered aromatic heterocyclic carbonylamino group" in the present specification is a group in which a 6-membered aromatic heterocyclic carbonyl group is bonded to an amino group.

The "C1-C6 alkylsulfonylamino group" in the present specification is a group in which a C1-C6 alkyl group is bonded to the sulfonyl group of a sulfonylamino group, and it is preferably a methylsulfonylamino group, an ethylsulfonylamino group, or a propylsulfonylamino group.

The "pharmacologically acceptable salt" indicates a salt that can be used as a pharmaceutical. When the compound has an acidic group or a basic group, since it can be converted to a basic salt or an acidic salt by reacting with a base or an acid, it indicates a salt thereof.

The pharmacologically acceptable "basic salt" of the compound preferably includes an alkali metal salt such as a sodium salt, a potassium salt, and a lithium salt; an alkaline earth metal salt such as a magnesium salt and a calcium salt; organic base salts such as an N-methyl morpholine salt, a triethylamine salt, a tributylamine salt, a diisopropylethylamine salt, a dicyclohexylamine salt, an N-methylpiperidine salt, a pyridine salt, a 4-pyrrolidinopyridine salt, and a picoline salt; and an amino acid salt such as glycine salt, a lysine salt, an arginine salt, an ornithine salt, a glutamate, and an aspartate, and it is preferably an alkali metal salt.

The pharmacologically acceptable "acidic salt" of the compound preferably includes an inorganic acid salt such as a hydrohalide such as a hydrofluoride, a hydrochloride, a hydrobromide, and a hydroiodide, a nitrate, a perchlorate, a sulfate, and a phosphate; an organic salt such as a lower alkanesulfonate such as methanesulfonate, trifluoromethanesulfonate, and ethanesulfonate, an aryl sulfonate such as a benzenesulfonates, and a p-toluene sulfonate, an acetate, a malate, a fumarate, a succinate, a citrate, an ascorbate, a tartrate, an oxalate, a maleate, and the like; and an amino acid salt such as glycine salt, a lysine salt, an arginine salt, an ornithine salt, a glutamate, and an aspartate, and it is most preferably a hydrohalide (in particular, a hydrochloride).

The compound of the present invention or the pharmacologically acceptable salt thereof may absorb moisture, adhere to adsorbed water, or become hydrate by leaving in the air or recrystallization. The present invention also encompasses compounds of such various hydrates, solvates, and crystalline polymorphs.

The compounds of the present invention, their pharmacologically acceptable salts or solvates thereof, depending on the type and combination of substituents, may have various isomers such as geometric isomers such as a cis isomer and a trans isomer, tautomers, or optical isomers such as a d isomer and an l isomer, while the compounds include those all isomers, stereoisomers, and mixtures of these isomers and stereoisomers in any ratio unless otherwise specified. Mixtures of these isomers may be resolved by known resolution means.

The compounds of the present invention also include labels, that is, a compound in which one or more atoms of the compounds are substituted with an isotope (for example, 2H, 3H, 13C, 14C, 35S, and the like).

In addition, the present invention also encompasses so-called a prodrug. The prodrug is a compound having a group which can converted to an amino group, a hydroxyl group, a carboxyl group, or the like of the compound by hydrolysis or under physiological conditions, and as a group forming such a prodrug, it is a group described in Prog. Med., Vol. 5, pp. 2157 to 2161 (1985) or the like. As the prodrug, more specifically, when an amino group is present in the compound, a compound in which the amino group is acylated, alkylated, or phosphorylated (for example, it is a compound in which the amino group is eicosanoylated, alanylated, pentylaminocarbonylated, (5-methyl-2-oxo-1,3-dioxolen-4-yl) methoxycarbonylated, tetrahydrofuranylated, pyrrolidinyl methylated, pivaloyloxymethyliatied, or tert-butylated, or the like) and the like are included, when a hydroxyl group is present in the compound, a compound in which the hydroxyl group is acylated, alkylated, phosphorylated, or borated (for example, it is a compound in which the hydroxyl group is acetylated, palmitoylated, propanoylated, pivaloylated, succinylated, fumarylated, alanylated, or dimethylaminomethyl carbonylated, or the like.) and the like are included.

In addition, when a carboxy group is present in the compound, a compound in which the carboxy group is esterified or amidated (for example, it is a compound in which the carboxy group is ethyl esterified, phenyl esterified, carboxymethyl esterified, dimethylaminomethyl esterified, pivaloyloxymethyl esterified, ethoxycarbonyloxyethyl esterified, amidated, or methylamidated, or the like.), and the like are included.

In the present specification, unless otherwise described, the values of the powder X-ray diffraction analysis are values obtained using Cu—Kα radiation. When an X-ray other than Cu—Kα radiation is used, 2θ (°) varies according to the equation $2d \sin \theta = n\lambda$ (d is the distance between two surfaces, n is an arbitrary integer, λ is the wavelength of the X-ray), but these are merely expressions of the crystals of the present invention by substantially equivalent alternative expression methods and are included in the scope of the present invention, which can be easily understood by those skilled in the crystal arts. In addition, the relative intensities of the peaks shown by these charts may vary depending on, for example, the degree of crystallization of the sample, the method of preparation, or the like. 2θ (°) does not vary substantially, but it can vary within an error range (generally a range of ±0.2°) recognized by those skilled in the crystal arts. In the characteristic peak of powder X-ray diffraction represented by the angle 2θ, "about" indicates ±0.2°, and in another embodiment, it indicates ±0.1°.

Due to the nature of the data, the value of the powder X-ray diffraction analysis should not be interpreted strictly sine what is important is the crystal lattice spacing and the overall pattern in determining the identity of crystals, and since the relative intensity can vary depending somewhat on the direction of crystal growth, particle size, and measurement conditions.

(Production Method)
A Production method is described below. However, the method for producing the compound or the salt thereof is not limited to the following method in any way.

[Method A]
A method A is a method for producing a compound (A-III) of the present invention.

[Chemical formula 26]

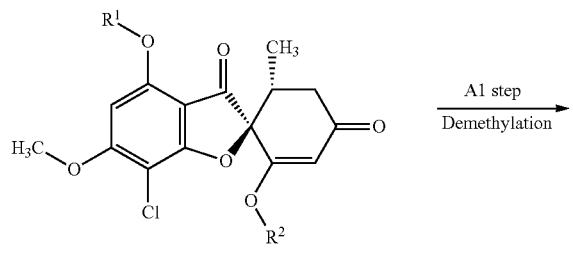

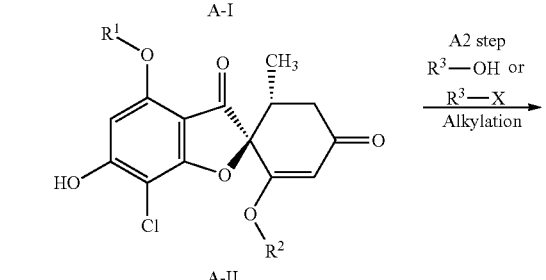

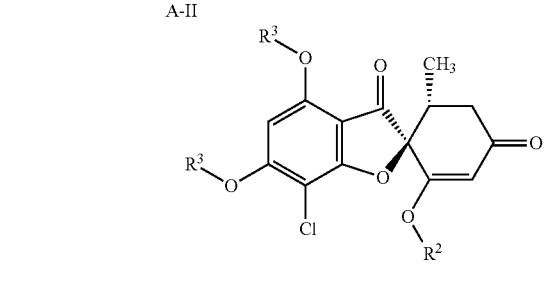

[In the formula, $R^1$, $R^2$, and $R^3$ have the same meaning as in the case of the compound of the above general formula (1) or (1'). X indicates a leaving group such as a halogen group.]

(A1 Step) Demethylation Step
This is a step of obtaining a compound (A-II) from a compound (A-I) using a metal halide in the presence of a base and a crown ether.

Examples of the base include triethylamine, diisopropylethylamine, pyridine, and the like.

Examples of the crown ether include 18-crown-6 and the like.

Examples of the metal halide include potassium iodide and the like.

The solvent may include, for example, N,N-dimethylformamide or the like, or a non-solvent, the reaction temperature is usually about 60 to 120° C., and the reaction time is usually about 1 to 24 hours.

(A2 Step) Alkylation Step
(When Using Halogenated Alkyl)
This is a step of obtaining the compound (A-III) from the compound (A-II) using a corresponding alkylation reagent in the presence of a base.

Examples of the alkylation reagent include a halogenated alkyl such as an alkyl iodide and an alkyl bromide, a sulfonate ester such as alkyl tosylate and alkyl mesylate, diethyl (bromodifluoromethyl) phosphonate, sodium chlorodifluoro acetate, and the like.

Examples of the base include triethylamine, diisopropylethylamine, potassium carbonate, potassium hydroxide, and the like.

As the solvent, tetrahydrofuran, 1,4-dioxane, acetonitrile, dichloromethane, N,N-dimethylformamide, and the like, are included, and a mixture thereof is included. The reaction temperature is usually about 0 to 100° C., and the reaction time is usually about 0.5 to 24 hours.

(In the Case of Using the Mitsunobu Reaction)
This is a step of obtaining the compound (A-III) from the compound (A-II) using a corresponding alcohol in the presence of a phosphine and an azodicarboxylic acid ester or a diazodicarboxamide.

Examples of the phosphine include triphenyl phosphine, tri-n-butyl phosphine, and the like are included.

Examples of the azodicarboxylate or diazodicarboxamide include diethyl azodicarboxylate, di-tert-butyl azodicarboxylate, 1,1'-(azodicarbonyl) dipyridine, and the like.

As the solvent, tetrahydrofuran, 1,4-dioxane, toluene, and the like, are included, and a mixture thereof is included. The reaction temperature is usually about 0 to 100° C., and the reaction time is usually about 0.5 to 24 hours.

[Method B]
A method B is a method for producing a compound (B-III) (a compound corresponding to the compound (A-I) used in the method A). When $R^1$ is a methyl group, the compound (B-III) may be produced without carrying out these steps.

[Chemical formula 27]

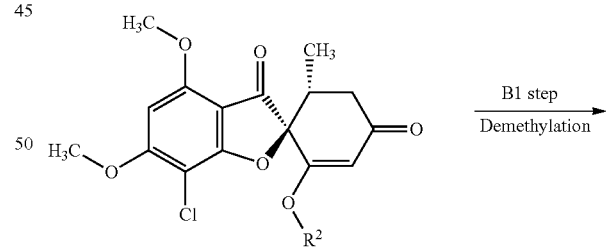

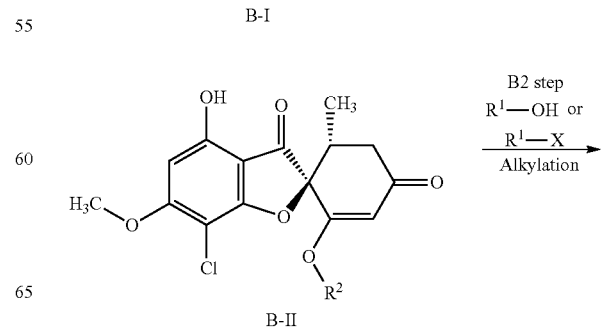

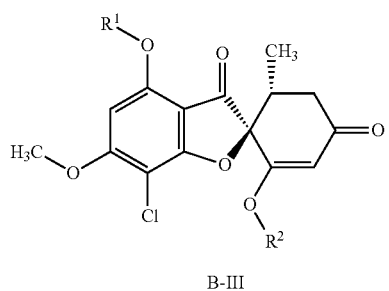

B-III

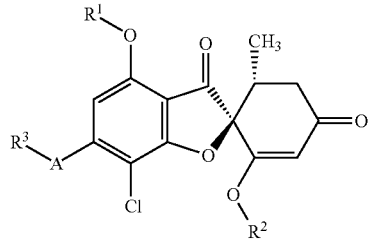

C-III

[In the formula, $R^1$ and $R^2$ have the same meaning as in the case of the compound of the above general formula (1) or (1'), and X has the same meaning as described above.]

(B1 Step) Demethylation Step

This is a step of obtaining a compound (B-II) from a compound (B-I) using a metal halide.

Examples of the metal halide include magnesium iodide and the like.

Examples of the solvent include toluene, tetrahydrofuran, 1,4-dioxane, and the like, or a mixture thereof may be included.

The reaction temperature is usually about 60 to 120° C., and the reaction time is usually about 0.5 to 24 hours.

(B2 Step) Alkylation Step

This is a step of obtaining the compound (B-III) from the compound (B-II). It may be carried out by the method similar to (A2 step).

[Method C]

A Method C is a method for producing a compound (C-III) of the present invention from a compound (C-I) (a compound corresponding to the compound (A-II) used in the method A).

[Chemical formula 28]

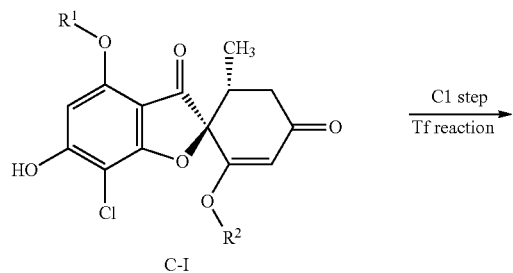

C-I

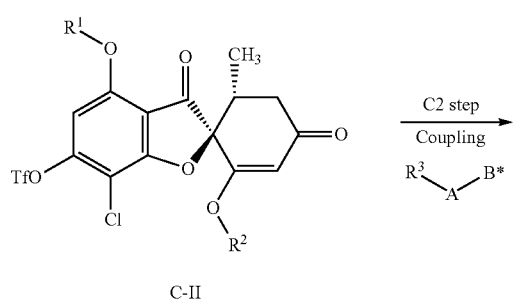

C-II

[In the formula, $R^1$, $R^2$, $R^3$, and A have the same meaning as in the case of the compound of the above general formula (1) or (1'). Tf indicates a trifluoromethane sulfonyl group, B* indicates a boronic acid or a boronic acid pinacol ester or the like.]

(C1 Step) Trifluoromethane Sulfonylation Step

This is a step of obtaining a compound (C-II) from the compound (C-I) in the presence of a base using a trifluoromethane sulfonylation reagent.

Examples of the trifluoromethane sulfonylation reagent include a trifluoromethane sulfonic acid anhydride, a trifluoromethane sulfonic acid chloride, N-phenylbis (trifluoromethane sulfone imide), and the like.

Examples of the base include triethylamine, diisopropylethylamine, and the like.

The solvent may include, for example, terhydrofuran, 1,4-dioxane, acetonitrile, dichloromethane, and the like, and it may include a mixture thereof.

The reaction temperature is usually about −20° C. to room temperature, and the reaction time is usually about 0.5 to 24 hours.

(C2 Step) Step of Carrying Out Coupling Reaction Using Transition Metal Catalyst This is a step of obtaining the compound (C-III) using a palladium catalyst and a boronic acid or a boronic acid pinacol ester of $R^3$-A in the presence of a base from the compound (C-II).

Examples of the palladium catalyst include tetrakis (triphenyl phosphine) palladium, [1,1'-bis (diphenyl phosphino) ferrocene] dichloro palladium, tris (dibenzylidene acetone) dipalladium, palladium acetate, acetyl acetone palladium, bis (triphenyl phosphine) palladium dichloride, and the like.

Examples of the base include triethylamine, diisopropylethylamine, 1,8-diazabicyclo [5.4.0]-7-undecene (DBU), 1,5-diazabicyclo [4.3.0]-5-nonene (DBN), potassium hydrogen carbonate, sodium bicarbonate, potassium carbonate, sodium carbonate, potassium hydroxide, sodium hydroxide, potassium phosphate, sodium phosphate, and the like.

Examples of the solvent, methanol, ethanol, tetrahydrofuran, 1,4-dioxane, water, N,N-dimethylformamide, dimethylsulfoxide, toluene, and the like may be included. A mixture thereof may be included.

The reaction temperature is usually about 60 to 120° C., and the reaction time is usually about 0.5 to 12 hours.

[Method D]

A method D is a method for producing a compound (D-IV) of the present invention from a compound (D-I) (a compound corresponding to the compound (C-II) used in the method C).

[Chemical formula 29]

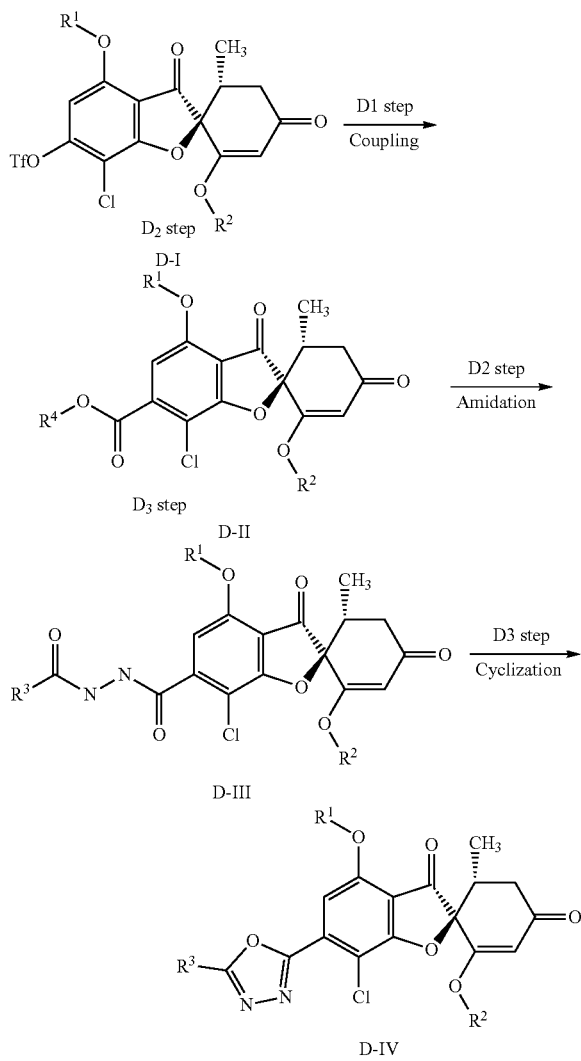

[In the formula, $R^1$, $R^2$, and $R^3$ have the same meaning as in the case of the compound of the above general formula (1) or (1'). Tf indicates the same meaning as described above, and $R^4$ indicates a phenyl group optionally has a substituent.]

(D1 Step) Step of Coupling with Formate Ester

This is a step of obtaining a compound (D-II) from the compound (D-I) using a formate ester in the presence of a base and a palladium catalyst (a phosphine ligand).

Examples of the base include triethylamine, diisopropylethylamine, dimethylaminopyridine, potassium carbonate, sodium carbonate, potassium hydroxide, sodium hydroxide, and the like.

Examples of the formate ester include phenyl formate, formate (2,4,6-trichlorophenyl), and the like.

Examples of the palladium catalyst include palladium acetate, palladium acetylacetonate, palladium trifluoroacetate, palladium dichloride, tris (dibenzylidene acetone) dipalladium, bis (triphenyl phosphine) palladium dichloride, and the like.

Examples of the phosphine ligand to be used simultaneously with the palladium catalyst may include 4,5-bis (diphenyl phosphino)-9,9-dimethyl xanthene (xantphos), 1,1'-bis (diphenyl phosphino) ferrocene (dppf), 2,2'-bis (diphenyl phosphino)-1,1-binaphthyl (BINAP), bis (diphenyl phosphino) methane (DPPM), triphenyl phosphine, 1,2-bis (diphenyl phosphino) ethane (DPPE), and the like.

Examples of the solvent include N,N-dimethylformamide, toluene, tetrahydrofuran, acetonitrile, and the like, and a mixture thereof is included.

The reaction temperature is usually about room temperature to 120° C., and the reaction time is usually about one to eight hours.

(D2 Step) Step of Carrying Out Amidation with Acylhydrazine

This is a step of obtaining a compound (D-III) from the compound (D-II) using a corresponding acylhydrazine in the presence of a base.

Examples of the base include triethylamine, diisopropylethylamine, dimethylaminopyridine, potassium carbonate, sodium carbonate, potassium hydroxide, sodium hydroxide, and the like. As an additive, N-hydroxysuccinimide (HOSu), 1-hydroxybenzotriazole (HOBt), 1-hydroxy-7-azabenzotriazole (HOAt), or the like may be advantageous in facilitating the reaction.

Examples of the solvent include N,N-dimethylformamide, dichloromethane, tetrahydrofuran, acetonitrile, and the like, and a mixture thereof is included.

The reaction temperature is usually about 0 to 60° C., and the reaction time is usually about 1 to 12 hours.

(D3 Step) Ring Formation Step

This is a step of obtaining the compound (D-IV) from the compound (D-III) using a dehydrating agent.

Examples of the dehydrating agent include a (methoxycarbonyl sulfamoyl) triethylammonium hydroxide inner salt, phosphoryl chloride, polyphosphoric acid, sulfuric acid, triphenyl phosphine/iodine, succinic acid, tosylate, tosyl chloride, and the like.

Examples of the solvent include toluene, acetonitrile, dichloromethane, and the like, and a mixed solvent thereof and non-solvent are included.

The reaction temperature is usually about 0 to 100° C., and the reaction time is usually about 0.5 to 24 hours.

[Method E]

A method E is a method for producing a compound (E-III) of the present invention from the compound (E-I) (a compound corresponding to a compound (D-II) used in the method D).

[Chemical formula 30]

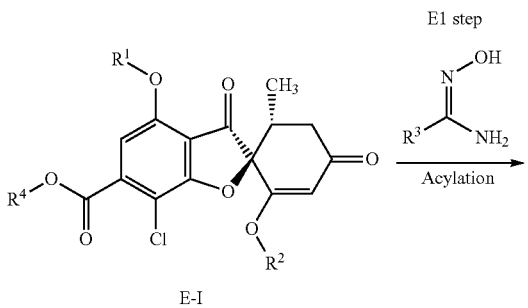

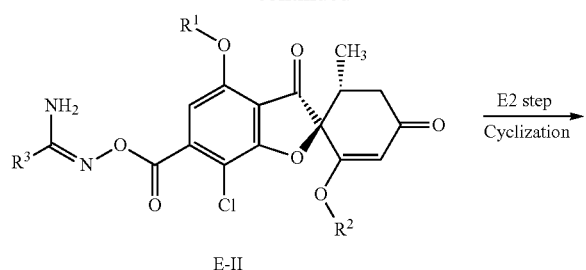

E-II

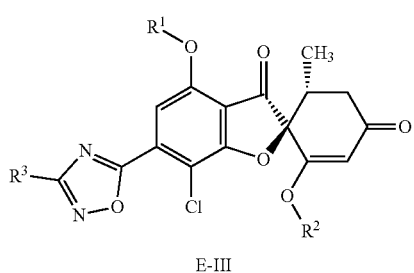

E-III

[In the formula, $R^1$, $R^2$, and $R^3$ have the same meaning as in the case of the compound of the above general formula (1) or (1'), and $R^4$ has the same meaning as described above.]

(E1 Step) Step of Carrying Out Acylation with Amidoxime

This is a step of obtaining a compound (E-II) from a compound (E-I) using a corresponding amidoxime in the presence of a base.

Examples of the base include triethylamine, diisopropylethylamine, dimethylaminopyridine, potassium carbonate, sodium carbonate, potassium hydroxide, sodium hydroxide, and the like, and as an additive, N-hydroxysuccinimide (HOSu), 1-hydroxybenzotriazole (HOBt), 1-hydroxy-7-azabenzotriazole (HOAt), or the like may be advantageous in facilitating the reaction.

Examples of the solvent include N,N-dimethylformamide, dichloromethane, tetrahydrofuran, acetonitrile, and the like, and a mixture thereof is included.

The reaction temperature is usually about room temperature to 80° C., and the reaction time is usually about 1 to 12 hours.

(E2 Step) Ring Formation Step

This is a step of obtaining a compound (E-III) by stirring the compound (E-II) in a solvent at room temperature or under heating.

Examples of the solvent include toluene, N,N-dimethylformamide, dichloromethane, tetrahydrofuran, acetonitrile, and the like, and a mixture thereof is included.

The reaction temperature is usually about room temperature to 100° C., and the reaction time is usually about 0.5 to 24 hours.

[Method F]

A method F is a method for producing a compound (F-V) of the present invention from a compound (F-I) (a compound corresponding to the compound (C-II) used in the method C).

[Chemical formula 31]

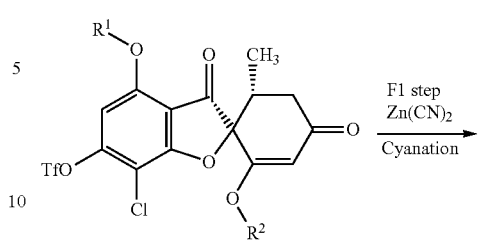

F-I

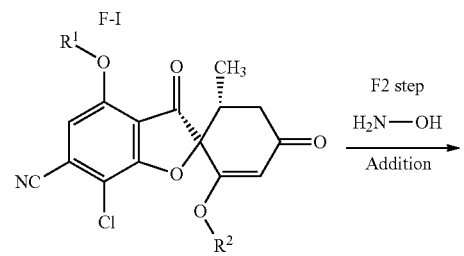

F-II

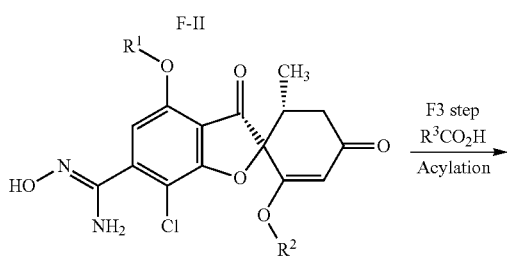

F-III

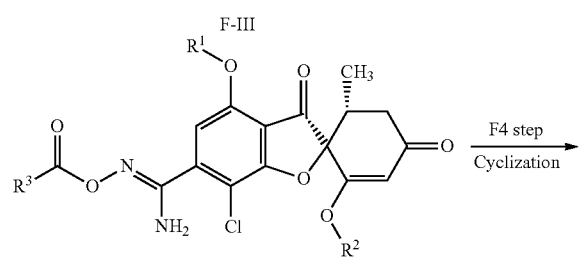

F-IV

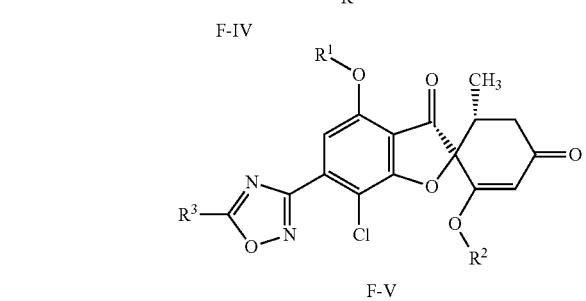

F-V

[In the formula, $R^1$, $R^2$, and $R^3$ have the same meaning as in the case of the compound of the above general formula (1) or (1'), and Tf has the same meaning as described above.]

(F1 Step) Step of Carrying Out Cyanation Using Transition Metal Catalyst

This is a step of obtaining a compound (F-II) from a compound (F-I) in the presence or absence of a phosphine and in the presence of zinc cyanide and a palladium catalyst.

Examples of the palladium catalyst include tris (dibenzylidene acetone) dipalladium, bis [tri (tert-butyl) phosphine] palladium, tetrakis (triphenyl phosphine) palladium, bis (trifluoro acetoxy) palladium, and the like.

Examples of the phosphine include triphenyl phosphine, tri (tert-butyl) phosphine, tri-o-toluyl phosphine, diphenyl phosphinoferrocene, diphenyl phosphinobutane, and the like. Examples of the solvent include N-methyl-2-pyrrolidone, N,N-dimethylformamide, and the like, and a mixture thereof is included.

The reaction temperature is usually about 80 to 120° C., and the reaction temperature is usually about one to eight hours.

(F2 Step) Hydroxylamine Addition Step

This is a step of obtaining a compound (F-III) from the compound (F-II) using hydroxylamine.

Examples of the solvent include methanol, ethanol, dimethylsulfoxide, water, and the like, and a mixture of these solvents is included.

The reaction temperature is usually about room temperature to 100° C., and the reaction time is usually about 0.5 to 24 hours.

(F3 Step) Step of Acylation of Oxime

This is a step of obtaining a compound (F-IV) from the compound (F-III) in the presence of a condensing agent and a base using a corresponding carboxylic acid.

Examples of the condensing agent includes O-(7-azabenzotriazole-1-yl)-N,N,N',N'-tetramethyluronium hexafluorophosphate (HATU), 4-(4,6-dimethoxy-1,3,5-triazin-2-yl)-4-methylmorpholine (DMT-MM), 1-(3-dimethylaminopropyl)-3-ethylcarbodiimide (WSC or EDCI), and the like.

Examples of the base include triethylamine, diisopropylethylamine, dimethylaminopyridine and the like.

As an additive, N-hydroxysuccinimide (HOSu), 1-hydroxybenzotriazole (HOBt), 1-hydroxy-7-azabenzotriazole (HOAt), or the like may be advantageous in facilitating the reaction.

Examples of the solvent may include ethanol, tetrahydrofuran, acetonitrile, N,N-dimethylformamide, dichloromethane, toluene, and the like, and a mixture of these solvents may be included.

The reaction temperature is usually about room temperature to 60° C., and the reaction time is usually about 0.5 to 24 hours.

(F4 Step) Ring Formation Step

This is a step of obtaining the compound (F-V) by stirring the compound (F-IV) in a solvent at room temperature or under heating.

Examples of the solvent may include toluene, N,N-dimethylformamide, dichloromethane, tetrahydrofuran, acetonitrile, and the like, and a mixture thereof is included.

The reaction temperature is usually about 60 to 120° C., and the reaction time is usually about 0.5 to 24 hours.

[Method G]
A method G is a method for producing a compound (G-III) of the present invention from a compound (G-I).

[Chemical formula 32]

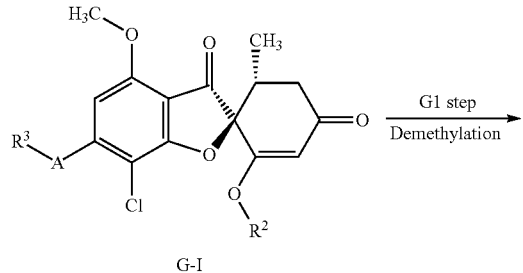

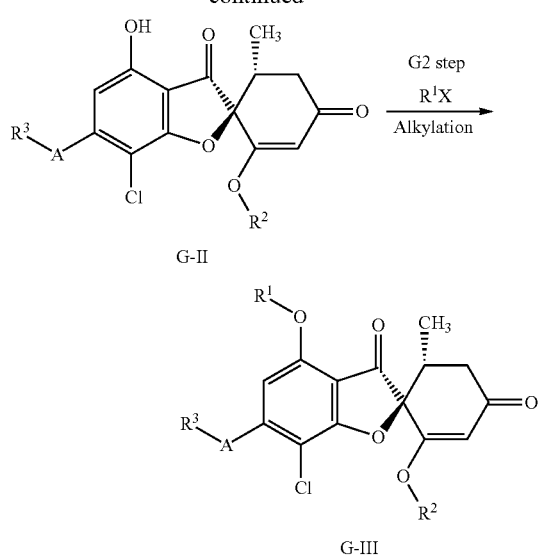

[In the formula, $R^1$, $R^2$, and $R^3$ have the same meaning as in the case of the compound of the above general formula (1) or (1'), and X has the same meaning as described above.]

(G1 Step) Demethylation Step

This is a step of obtaining a compound (G-II) from the compound (G-I). It may be carried out by the method similar to (B1 step).

(G2 Step) Alkylation Step

This step is a step of obtaining a compound (G-III) from the compound (G-II). It may be carried out by the method similar to (A2 step).

[Method H]

A method H is a method for producing a compound (H-II) of the present invention by deprotecting the protective group when $R^1$ or $R^3$ of the compound (H-I) contains a protective group.

[Chemical formula 33]

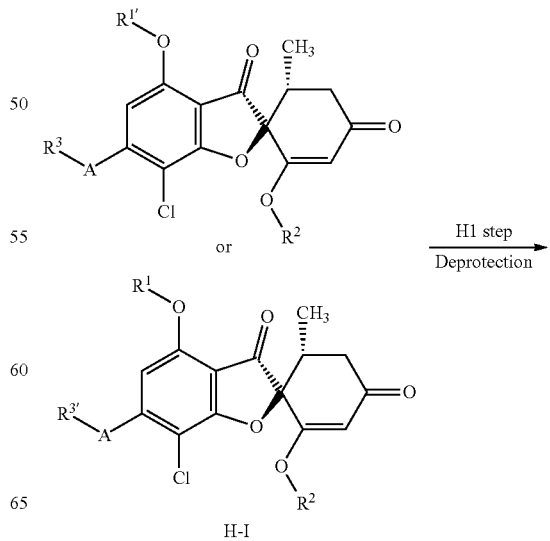

-continued

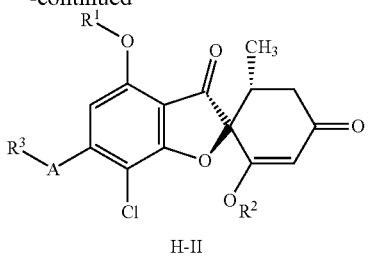

H-II

[In the formula, $R^1$, $R^2$, $R^3$, and A have the same meaning as in the case of the compound of the above general formula (1) or (1'), and $R^{1'}$ and $R^{3'}$ indicate protected $R^1$ and $R^3$, respectively.]

(H1 Step) Deprotection Step
(In the Case of Tetrahydropyranyl (THP))

This is a step of obtaining the compound (H-II) from the compound (H-I) containing a hydroxy group protected with a tetrahydropyranyl group using an acid.

Examples of the acid include hydrochloric acid, sulfuric acid, hydrochloric acid-methanol, hydrochloric acid-1,4-dioxane, hydrochloric acid-ethyl acetate, acetic acid, p-toluene sulfonic acid, or pyridinium p-toluene sulfonate.

Examples of the solvent include methanol, ethanol, tetrahydrofuran, water, a mixture thereof, and the like.

The reaction temperature is usually about 0 to 80° C., and the reaction time is usually about 0.5 to 24 hours.

(In the Case of Silyl Group)

This is a step of obtaining the compound (H-II) from the compound (H-I) containing a hydroxy group protected by a silyl group using a desilylation reagent.

Examples of the desilylation reagent include an acid or tetrabutyl ammonium fluoride (TBAF), hydrogen fluoride, hydrogen fluoride pyridine, and the like.

Examples of the acid may include hydrochloric acid, sulfuric acid, hydrochloric acid-methanol, hydrochloric acid-1,4-dioxane, hydrochloric acid-ethyl acetate, acetic acid, p-toluene sulfonic acid, trifluoroacetic acid, and the like, and it is also possible to react at a catalyst amount.

Examples of the solvent may include methanol, ethanol, tetrahydrofuran, 1,2-dimethoxyethane, 1,4-dioxane, acetonitrile, water, and the like, and a mixture thereof may be included.

The reaction temperature is usually about 0 to 60° C., and the reaction time is usually about 0.5 to 24 hours.

[Method I]

A method I is a method for producing a compound (I-IV) of the present invention from a compound (I-I) (a compound corresponding to the compound (D-II) used in the method D).

[Chemical formula 34]

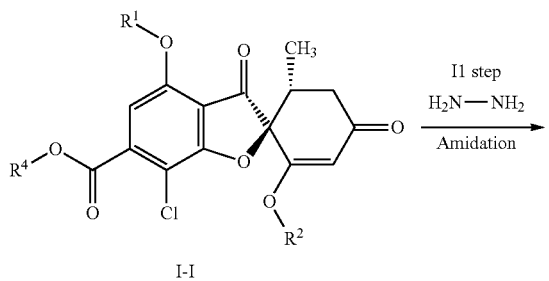

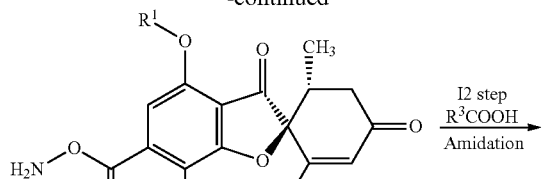

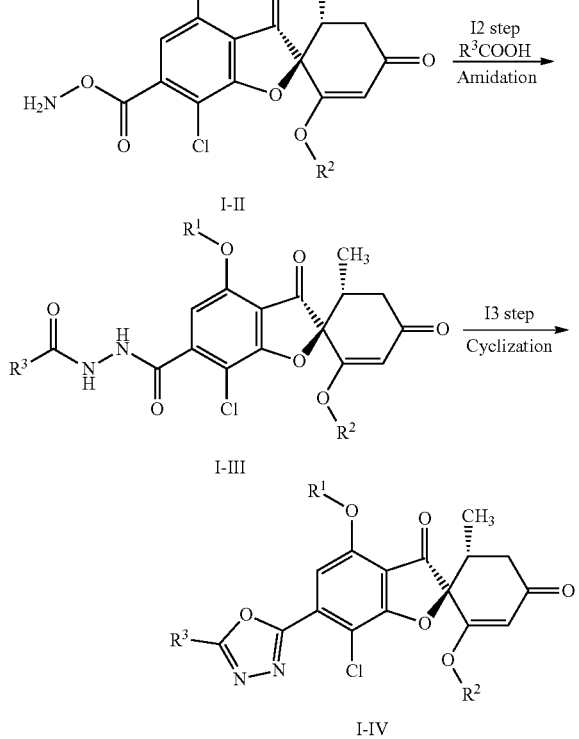

[In the formula, $R^1$, $R^2$, and $R^3$ have the same meaning as in the case of the compound of the above general formula (1) or (1'), and $R^4$ has the same meaning as described above.]

(I1 Step) Step of Carrying Out Amidation with Hydrazine

This is a step for obtaining a compound (I-II) from the compound (I-I) using hydrazine in the presence of a base.

Examples of the base include triethylamine, diisopropylethylamine, dimethylaminopyridine, potassium carbonate, sodium carbonate, potassium hydroxide, sodium hydroxide, and the like. As an additive, N-hydroxysuccinimide (HOSu), 1-hydroxybenzotriazole (HOBt), 1-hydroxy-7-azabenzotriazole (HOAt), or the like may be advantageous in facilitating the reaction.

Examples of the solvent may include N,N-dimethylformamide, dichloromethane, tetrahydrofuran, acetonitrile, and the like, and a mixture thereof is included.

The reaction temperature is usually about 0 to 30° C., and the reaction time is usually about 1 to 24 hours.

(I2 Step) Step of Acylating Acylhydrazine

This is a step of obtaining a compound (I-III) from the compound (I-II) in the presence of a condensing agent and a base using a corresponding carboxylic acid.

Examples of the condensing agent include O-(7-azabenzotriazole-1-yl)-N,N,N',N'-tetramethyluronium hexafluorophosphate (HATU), 4-(4,6-dimethoxy-1,3,5-triazine-2-yl)-4-methylmorpholine (DMT-MM), 1-(3-dimethylaminopropyl)-3-ethylcarbodiimide (WSC or EDCI), and the like.

Examples of the base include triethylamine, diisopropylethylamine, dimethylaminopyridine, and the like.

As an additive, N-hydroxysuccinimide (HOSu), 1-hydroxybenzotriazole (HOBt), 1-hydroxy-7-azabenzotriazole (HOAt), or the like may be advantageous in facilitating the reaction.

Examples of the solvent may include ethanol, tetrahydrofuran, acetonitrile, N,N-dimethylformamide, dichloromethane, toluene, and the like, and a mixture of these solvents may be included.

The reaction temperature is usually about room temperature to 60° C., and the reaction time is usually about 0.5 to 24 hours.

(D3 Step) Ring Formation Step

This is a step of obtaining the compound (I-IV) from the compound (I-III). It may be carried out by the method similar to (D3 step).

[Method J]

A method J is a method for producing a compound (J-V) of the present invention from a compound (J-I) (a compound corresponding to the compound (C-II) used in the method C).

[Chemical formula 35]

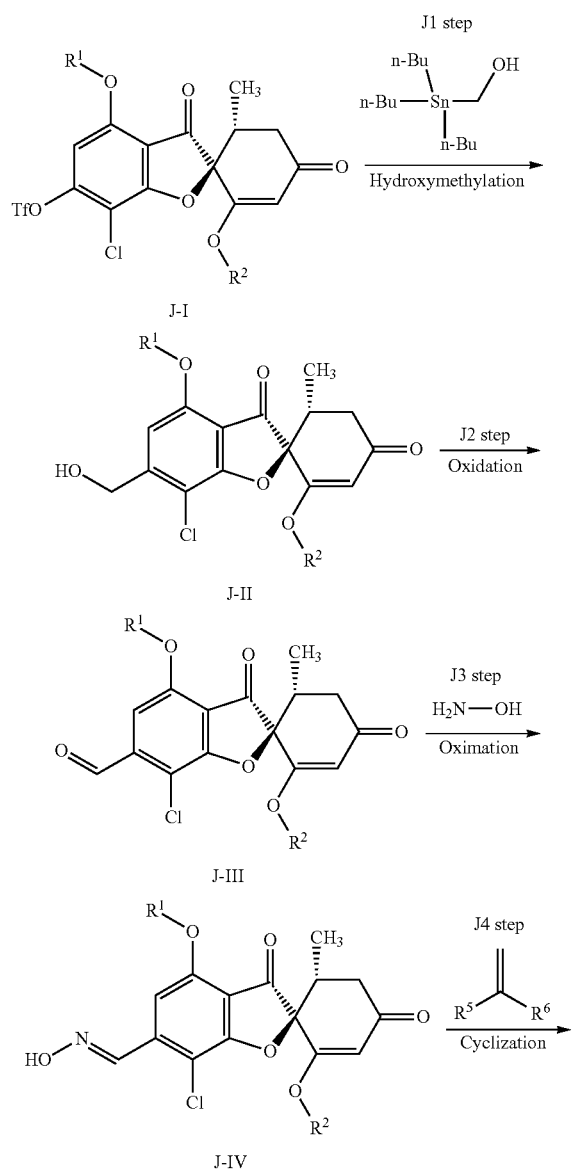

[In the formula, $R^1$ and $R^2$ have the same meaning as in the case of the compound of the above general formula (1) or (1'), and $R^5$ and $R^6$ each independently indicate hydrogen, a C1-C6 alkyl group, or a 5-7 membered unsaturated heterocyclic ring, a 4-7 membered saturated heterocyclic ring, or a C3-C6 cycloalkyl ring, in which both are bonded to each other.]

(J1 Step) Step of Carrying Out Hydroxymethylation Using Transition Metal Catalyst This is a step of obtaining a compound (J-II) from the compound (J-I) using tributylstannyl methanol in the presence or absence of a phosphine and in the presence of a palladium catalyst.

Examples of the palladium catalyst include tetrakis (triphenyl phosphine) palladium, bis (triphenyl phosphine) palladium (II) dichloride, and the like.

Examples of the phosphine include triphenyl phosphine, tri-o-toluyl phosphine, and the like.

Examples of the solvent may include 1,4-dioxane, ethanol, or N,N-dimethylformamide, and the like, and a mixture thereof is included.

The reaction temperature is usually about 80 to 120° C., and the reaction time is usually about 1 to 24 hours.

(J2 step) Step of oxidation of alcohol

This is a step of obtaining a compound (J-III) by reacting the compound (J-II) with an oxidizing agent.

Examples of the oxidizing agent include Dess-Martin Periodinane (Dess-Martin Periodinane), dimethyl sulfoxide, chromic acid, and the like.

Examples of the solvent include dichloromethane, acetonitrile, and the like.

The reaction temperature is usually about −20° C. to 40° C., and the reaction time is usually about 0.5 to 24 hours.

(J3 Step) Oximation Step

This is a step of obtaining a compound (J-IV) from the compound (J-III) using hydroxylamine or a hydrochloride thereof in the presence or absence of a base.

Examples of the base include sodium acetate, sodium hydroxide, sodium bicarbonate, potassium carbonate, pyridine, and the like.

Examples of the solvent include methanol, ethanol, water, and the like, and a mixture thereof is included.

The reaction temperature is usually about room temperature to 100° C., and the reaction time is usually about 1 to 24 hours.

(J4 Step) Ring Formation Step

This is a step of obtaining the compound (J-V) from the compound (J-IV) using a chlorination reagent in the presence or absence of a base.

Examples of the base include triethylamine, diisopropylethylamine, pyridine, 1,8-diazabicyclo [5.4.0]-7-undecene (DBU), and the like.

Examples of the chlorinating reagent include N-chlorosuccinimide (NCS), sodium hypochlorite, tert-butyl hypochlorite, and the like.

Examples of the solvent include N,N-dimethylformamide, dichloromethane, chloroform, tetrahydrofuran, 1,4-dioxane, acetonitrile, water, and the like, and a mixture thereof is included.

The reaction temperature is usually about −20 to 40° C., and the reaction time is usually about 1 to 24 hours.

[Method K]

A method K is a method for producing a compound (K-II) of the present invention by alkylating $R^{1'}$ or $R^{3'}$ of a compound (K-I).

[Chemical formula 36]

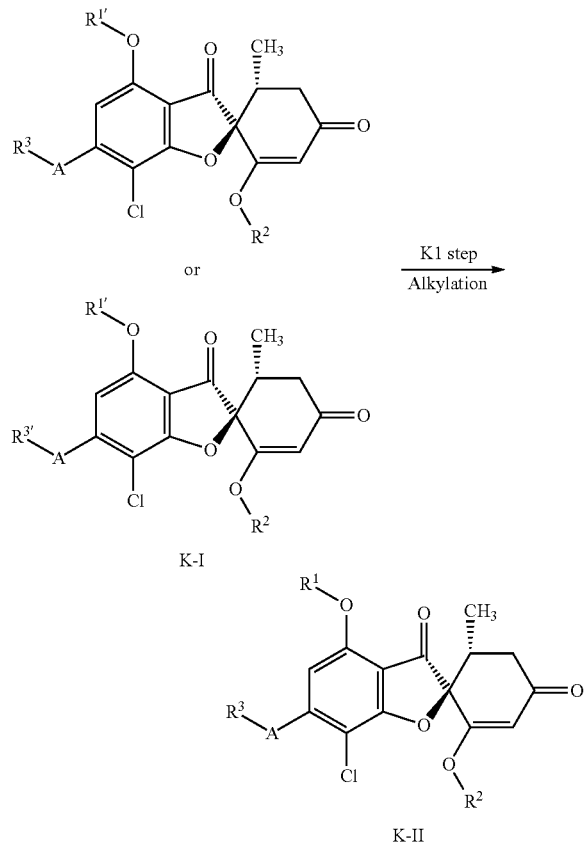

[In the formula, $R^1$, $R^2$, $R^3$, and A have the same meaning as in the case of the compound of the above general formula (1) or (1'), and $R^{1'}$ and $R^{3'}$ each independently indicate a C1-C6 alkyl group which has a substituent containing a hydrogen atom or active hydrogen such as, a hydroxyl group or an amino group.]

(K1 Step) Alkylation Step (When Using Halogenated Alkyl)

This is a step of obtaining the compound (K-II) from the compound (K-I). It may be carried out by the method similar to (A2 step).

(When Using Reductive Amination Reaction)

This is a step of obtaining the compound (K-II) by reacting the compound (K-I) with a corresponding aldehyde in the presence or absence of an acid using a reducing agent.

Examples of the reducing agent include sodium triacetoxy borohydride, sodium cyanoborohydride, and the like.

Examples of the acid may include acetic acid, tetraisopropyl orthotitanate, zinc chloride, and the like.

Examples of the solvent include methanol, acetonitrile, water, tetrahydrofuran, dichloromethane, and the like, and a mixture thereof may be included. The reaction temperature is usually about 0 to 80° C., and the reaction time is usually about 0.5 to 24 hours.

The compounds produced by the above methods may be isolated and purified by known methods such as extraction, precipitation, distillation, chromatography, fractional recrystallization, and recrystallization.

In addition, when the compound or intermediate of production has asymmetric carbon, optical isomers exist. Each of may be isolated and purified by a conventional method such as fractional recrystallization (salt resolution) in which these optical isomers are recrystallized by conversion to appropriate salts and column chromatography. As a reference document for the method of resolving an optical isomer from racemates, J. Jacques et al., "Enantiomers, Racemates and Resolution, John Wiley And Sons, Inc." may be included.

(Administration Form)

Administration may be carried out by any form of oral administration by a tablet, a pill, a capsule, a granule, a powder, a solution, or the like, or by any forma of parenteral administration by an injection for intra-articular, intravenous, intramuscular, or the like, a suppository, an eye drop, an eye ointment, a transdermal solution, an ointment, a transdermal patch, a transmucosal solution, a transmucosal patch, an inhalant, or the like.

As a solid composition for oral administration, a tablet, a powder, a granule, and the like are used. Such a solid composition is composed of one or more active ingredients and at least one inert excipient such as lactose, mannitol, glucose, hydroxypropyl cellulose, microcrystalline cellulose, starch, polyvinyl pyrrolidone, magnesium metasilicate aluminate, and/or the like. The solid composition may contain, according to a conventional method, an inert additive such as a lubricant such as magnesium stearate, a disintegrant such as sodium carboxymethyl starch, a stabilizer, and a solubilizer. The tablet or pill may be coated with a sugar coating or a film of a substance soluble in the stomach or intestine, if necessary.

As a liquid composition for oral administration, a pharmaceutically acceptable emulsion, solution, suspension, syrup, elixir, or the like is used. To such a liquid composition, it is possible to add generally used inert diluent such as purified water or ethanol. The liquid composition may contain, in addition to an inert diluent, a solubilizer, an adjuvant such as a wetting agent, a sweetening agent, a flavoring agent, a fragrance, and a preservative.

As an injection for parenteral administration, a sterile aqueous or non-aqueous solution, a suspension or an emulsion, and the like are used. The aqueous solvent includes, for example, distilled water for injection, physiological saline, and the like. The non-aqueous solvents include, for example, propylene glycol, polyethylene glycol, and vegetable oil such as olive oil, alcohols such as ethanol, Polysorbate 80, and the like. Such an injection composition may further contain a tonicity agent, a preservative, a wetting agent, an emulsion, a dispersing agent, a stabilizer, or a solubilizer. These injection compositions can be sterilized by, for example, filtration through a bacteria retention filter, application of a bactericide, or irradiation. In addition, these injection compositions may be used by producing a sterile solid composition and dissolved or suspended in sterile water or a sterile solvent for injection prior to use.

As an external preparation, an ointment, a plaster, a cream, a jelly, a cataplasm, a spray, a lotion, an eye drop, an eye ointment, and the like are used. These external preparations include generally used ointment bases, lotion bases, aqueous or non-aqueous solutions, suspensions, emulsions, and the like. For example, as an ointment or lotion base, polyethylene glycol, propylene glycol, white petrolatum, bleached beeswax, polyoxyethylene hydrogenated castor oil, glycerin monostearate, stearyl alcohol, cetyl alcohol, lauromacrogol, sorbitan sesquioleate, and the like are used.

A transmucosal agent such as an inhalant and a transnasal agent are used in solid, liquid, or semisolid form, and it may be produced according to a conventionally known method. For example, a known excipient, and furthermore, a pH adjuster, a preservative, a surfactant, a lubricant, a stabilizer, a thickener, and the like may be added as appropriate. With these transmucosal agents, devices appropriate for inhalation or insufflation may be used as the method of administration. For example, the compound may be administered alone or as a powder of a formulated mixture, or as a solution or suspension in combination with a pharmaceutically acceptable carrier, using known devices and nebulizers, such as metered dose inhalation devices. A dry powder inhaler or the like may be for single or multiple administration, and a dry powder or powder containing capsule may be also used. Alternatively, an appropriate ejector may be used. For example, it may be in the form of a pressurized aerosol spray or the like using a suitable gas such as chlorofluoroalkane, hydrofluoroalkane, or carbon dioxide.

(Dosage)

In the case of normal oral administration, the appropriate daily dose is about 0.001 to 100 mg/kg, preferably 0.1 to 30 mg/kg, and more preferably 0.1 to 10 mg/kg of body weight. This is administered in one dose or separated into two or more doses. When administered intravenously, the appropriate daily dose is about 0.0001 to 10 mg/kg of body weight, which is administered once or separated into several times a day. In addition, as a transmucosal agent, about 0.001 to 100 mg/kg of body weight is administered once or separated into several times a day. The dose is appropriately determined depending on the individual case in consideration of symptoms, age, sex, and the like.

(Combined Usage)

In the present invention, it may be used in combination with various therapeutic agents or preventive agents for diseases that are considered to exhibit the efficacy thereof. The combination may be administered simultaneously, separately and continuously or at desired time intervals. The co-administered formulations may be blended or formulated separately, even if it is a compounding agent.

(Formulation Example 1) Powder

A powder is obtained by mixing 5 g of the compound of the present invention or the salt thereof, 895 g of lactose, and 100 g of corn starch in a blender.

(Formulation Example 2) Granule

After 5 g of the compound of the present invention or the salt thereof, 865 g of lactose, and 100 g of low substituted hydroxypropyl cellulose are mixed, 300 g of a 10% hydroxypropyl cellulose aqueous solution is added and kneaded. This is granulated using an extrusion granulator and dried to obtain granules.

(Formulation Example 3) Tablet

After 5 g of the compound of the present invention or the salt thereof, 90 g of lactose, 34 g of corn starch, 20 g of crystalline cellulose, and 1 g of magnesium stearate are mixed with a blender, and tablets are obtained by tableting with a tableting machine.

The pharmacological activity of the compound of the present invention or the pharmacologically acceptable salt thereof was confirmed by the following test.

(Test Example) Forced Swim Test

Male ddY mice (4 weeks old at the time of evaluation) were used for the test in groups of 10 mice. The mice were placed in a water bath (inner diameter 14.5 cm, height 20 cm, water temperature about 24° C.) with water filled to a height of about 15 cm, and a swimming trial was carried out for 15 minutes (training trial). The next day, mice were orally administered with a suspension of each compound (10 mL/kg, solvent: 0.5% methylcellulose aqueous solution) was orally administered to the mice, and four hours later, they were placed in the water bath. Immobility time (sec) was measured for six minutes immediately after that, and the ratio of the average immobility time of each compound administration group with respect to the average immobility time of a control group (10 mL/kg administration of 0.5% methylcellulose aqueous solution without a compound) was calculated.

TABLE 1

| Example No. | Dose (mg/kg) | Ratio of the average immobility time (%) |
| --- | --- | --- |
| Griseofulvin | 100 | 72 |
| 2 | 10 | 71 |
| 3 | 10 | 84 |
| 4 | 10 | 61 |
| 5 | 10 | 62 |
| 6 | 10 | 67 |
| 17 | 10 | 72 |
| 18 | 10 | 85 |
| 21 | 10 | 87 |
| 22 | 10 | 88 |
| 24 | 10 | 65 |
| 25 | 10 | 58 |
| 26 | 10 | 72 |
| 28 | 10 | 80 |
| 30 | 10 | 70 |
| 31 | 10 | 68 |

The results of this test indicate a decrease in average immobility time from the comparison with the control group in each compound administration group used in the present test, and the effect of the compound of the present invention could be confirmed from the present test.

According to the test results, it was indicated that the compound of the present invention or the pharmacologically acceptable salt thereof was effective for the prevention and/or treatment of central inflammatory diseases such as Alzheimer's disease, Parkinson's disease, Lewy body dementia, multiple system atrophy, Pick's disease, progressive supranuclear palsy, cerebral cortex basement degeneration, frontotemporal lobe degeneration, Huntington's disease, amyotrophic lateral sclerosis, spinal and bulbar muscular atrophy, spinal muscular atrophy, spinocerebellar degeneration, multiple sclerosis, Creutzfeldt-Jakob disease, fatal familial insomnia, Gerstmann-Straussler-Scheinker syndrome, Down syndrome, Niemann-Pick disease, cerebral amyloid angiopathy, HIV encephalopathy, influenza encephalopathy, hepatic encephalopathy, progressive multifocal leukoencephalopathy, anti-NMDA receptor antibody encephalitis, cerebrovascular disorders, traumatic brain injuries, spinal cord injuries, hypoxic encephalopathy, epilepsy, optic neuritis, congenital metabolic brain diseases, Wernicke's encephalopathy, autism spectrum disorders, attention deficit/hyperactivity disorders, tic disorders, schizophrenia, bipolar disorders, major depressive disorders (treatment resistant depression and postpartum depression), persistent depressive disorders (dysthymic disorder), premenstrual dysthymic disorders, anxiety disorders, focal phobia, panic disorders, obsessive compulsive disorders, emotional trauma and stress related disorders, eating disorders, circadian rhythm sleep/wake disorders, narcolepsy, substance related disorders (alcohol addiction and drug addiction), impulse control disorders, delirium, personality disorders, and Rett's syndrome.

EXAMPLE

Hereinafter, the present invention will be described in more detail by way of examples, but the scope of the present invention is not limited thereto.

In the following examples, nuclear magnetic resonance (hereinafter, $^1$H NMR) spectra were described using δ values (ppm) as chemical shift values with tetramethylsilane as a standard substance. The split pattern is indicated by s for singlet, d for doublet, t for triplet, q for quartet, m for multiplet, and br for broad.

Example 1

(2S,5'R)-7-chloro-6-(2-hydroxyethoxy)-3',4-dimethoxy-5'-methyl-spiro [benzofuran-2,4'-cyclohex-2-ene]-1',3-dione (1a)

(2S,5'R)-7-chloro-6-hydroxy-3',4-dimethoxy-5'-methyl-spiro [benzofuran-2,4'-cyclohex-2-ene]-1',3-dione (2S,5'R)-7-chloro-6-hydroxy-3',4-dimethoxy-5'-methyl-spiro [benzofuran-2,4'-cyclohex-2-ene]-1',3-dione (+)-griseofulvin ((2S,5'R)-7-chloro-3',4,6-trimethoxy-5'-methyl-spiro [benzofuran-2,4'-cyclohex-2-ene]-1',3-dione, CAS number: 126-07-8, Product code: G0384 (Tokyo Chemical Industry)) (50 g), potassium iodide (23.5 g), and 18-crown 6-ether (41.2 g) were dissolved in pyridine (500 mL), the mixture was stirred at 120° C. for nine hours and allowed to stand at room temperature overnight.

The reaction mixture was concentrated, 4% sodium bicarbonate aqueous solution was added, and the mixture was washed twice with ethyl acetate. The aqueous layer was neutralized with 1 mol/L hydrochloric acid and extracted with ethyl acetate. The organic layer was washed with water and saturated saline and dried with anhydrous sodium sulfate. The residue, which was obtained by distilling the solvent under reduced pressure, was purified by silica gel column chromatography [elution solvent: dichloromethane/ethanol=99/1 (V/V)] to obtain 19.4 g of a crude product.

After ethyl acetate was added to solidify, and filtration was carried out to obtain 15.2 g (yield: 32%) of the title compound as a white solid.

(1b)

(2S,5'R)-7-chloro-6-(2-hydroxyethoxy)-3',4-dimethoxy-5'-methyl-spiro [benzofuran-2,4'-cyclohex-2-ene]-1',3-dione (2S,5'R)-7-chloro-6-(2-hydroxyethoxy)-3',4-dimethoxy-5'-methyl-spiro [benzofuran-2,4'-cyclohex-2-ene]-1',3-dione (2S,5'R)-7-chloro-6-hydroxy-3',4-dimethoxy-5'-methyl-spiro [benzofuran-2,4'-cyclohex-2-ene]-1',3-dione (0.1 g) of example 1 (1a) was dissolved in N,N-dimethylformamide (3 mL), 2-bromoethanol (0.0738 g) and potassium carbonate (0.102 g) were added and stirred at 100° C. for six hours.

The reaction mixture was poured into water, and the reaction mixture was extracted with ethyl acetate. The organic layer was washed with water and saturated saline and dried with anhydrous sodium sulfate. The residue, which was obtained by distilling the solvent under reduced pressure, was purified by silica gel column chromatography [elution solvent: ethyl acetate] to obtain 38 mg (yield: 34%) of the title compound as a pale yellow solid.

Example 2

(2S,5'R)-7-chloro-3',4-dimethoxy-6-(2-methoxyethoxy)-5'-methyl-spiro [benzofuran-2,4'-cyclohex-2-ene]-1',3-dione (2S,5'R)-7-chloro-3',4-dimethoxy-6-(2-methoxyethoxy)-5'-methyl-spiro [benzofuran-2,4'-cyclohex-2-ene]-1',3-dione (2S,5'R)-7-chloro-6-hydroxy-3',4-dimethoxy-5'-methyl-spiro [benzofuran-2,4'-cyclohex-2-ene]-1',3-dione (30 mg) of example 1 (1a) was dissolved in N,N-dimethylformamide (1 mL), 2-bromoethylmethyl ether (136 mg) and potassium carbonate (135 mg) were added and stirred at 80° C. for six hours.

The reaction mixture was poured into water, and the reaction mixture was extracted with ethyl acetate. The organic layer was washed with water and saturated saline and dried with anhydrous sodium sulfate. The residue, which was obtained by distilling the solvent under reduced pressure, was purified by silica gel column chromatography [elution solvent: ethyl acetate] to obtain 20 mg (yield: 57%) of the title compound as a white solid.

Example 3

(2S,5'R)-7-chloro-3',4-dimethoxy-5'-methyl-6-(1-methylpyrazol-3-yl) spiro [benzofuran-2,4'-cyclohex-2-ene]-1',3-dione (3a)

[(2S,5'R)-7-chloro-1',4-dimethoxy-5'-methyl-3,3'-dioxo-spiro [benzofuran-2,6'-cyclohexene]-6-yl] trifluoromethanesulfonate

[(2S,5'R)-7-chloro-1',4-dimethoxy-5'-methyl-3,3'-dioxo-spiro [benzofuran-2,6'-cyclohexene]-6-yl] trifluoromethanesulfonate (2S,5'R)-7-chloro-6-hydroxy-3',4-dimethoxy-5'-methyl-spiro [benzofuran-2,4'-cyclohex-2-ene]-1',3-dione (20 g) of example 1 (1a) was dissolved in dichloromethane (300 mL), N-phenylbis (trifluoromethanesulfonimide) (25.3 g) and triethylamine (20.6 mL) were added, and the mixture was allowed to stand at room temperature overnight.

The reaction mixture was diluted with dichloromethane, and the organic layer was washed with water and saturated saline and dried with anhydrous sodium sulfate. The residue, which was obtained by distilling the solvent under reduced pressure, was purified by silica gel column chromatography [elution solvent: n-hexane/ethyl acetate=8/2 to 3/7 (V/V)] to obtain 23.5 g (yield: 85%) of the title compound as a white solid.

(3b)

(2S,5'R)-7-chloro-3',4-dimethoxy-5'-methyl-6-(1-methylpyrazol-3-yl) spiro [benzofuran-2,4'-cyclohex-2-ene]-1',3-dione (2S,5'R)-7-chloro-3',4-dimethoxy-5'-methyl-6-(1-methylpyrazol-3-yl) spiro [benzofuran-2,4'-cyclohex-2-ene]-1',3-dione

[(2S,5'R)-7-chloro-1',4-dimethoxy-5'-methyl-3,3'-dioxo-spiro [benzofuran-2,6'-cyclohexene]-6-yl]trifluoromethanesulfonate (76 mg) of example 3 (3a) was dissolved in N,N-dimethylformamide (1.6 mL), and 1-methyl-3-(4,4,5,5-tetramethyl-1,3,2-dioxaborolan-2-yl)-1H-pyrazole (0.0403 g), potassium carbonate (0.0669 g), and [1,1'-bis (diphenyl phosphino) ferrocene] palladium (II) dichloride dichloromethane adduct (0.0131 g) were added at room temperature and stirred at 80° C. for three hours.

After the reaction temperature was returned to room temperature, the reaction mixture was diluted with ethyl acetate, and the insoluble substances were filtered. The filtrate was poured into water and extracted with ethyl acetate. The organic layer was washed with water and saturated saline and dried with anhydrous sodium sulfate. The residue, which was obtained by distilling the solvent under reduced pressure, was purified by silica gel column chromatography [elution solvent: n-hexane/ethyl acetate=1/1 to 0/1 (V/V)] to obtain 27 mg (yield: 42%) of the title compound as a white solid.

Example 4

(2S,5'R)-7-chloro-6-(1-ethylpyrazol-3-yl)-3',4-dimethoxy-5'-methyl-spiro [benzofuran-2,4'-cyclohex-2-ene]-1',3-dione (2S,5'R)-7-chloro-6-(1-ethylpyrazol-3-yl)-3',4-dimethoxy-5'-methyl-spiro [benzofuran-2,4'-cyclohex-2-ene]-1',3-dione

[(2S,5'R)-7-chloro-1',4-dimethoxy-5'-methyl-3,3'-dioxo-spiro [benzofuran-2,6'-cyclohexene]-6-yl]trifluoromethanesulfonate (0.5 g) of example 3 (3a) was dissolved in toluene (10 mL), and 1-ethyl-3-(4,4,5,5-tetramethyl-1,3,2-dioxaborolan-2-yl)-1H-pyrazole (0.283 g), chloro (2-dicyclohexyl phosphino-2',4',6'-triisopropyl-1,1'-biphenyl) [2-(2'-amino-1,1'-biphenyl)] palladium (II) (0.167 g), and saturated sodium bicarbonate aqueous solution (5 mL) were added and stirred at 90° C. for two hours.

The reaction mixture was poured into water, and the reaction mixture was extracted with ethyl acetate. The organic layer was washed with water and saturated saline and dried with anhydrous sodium sulfate. The residue, which was obtained by distilling the solvent under reduced pressure, was purified by silica gel column chromatography [elution solvent: n-hexane/ethyl acetate=1/1 to 0/1 (V/V)] to obtain 266 mg (yield: 60%) of the title compound as a white solid.

Example 5

(2S,5'R)-7-chloro-3',4-dimethoxy-5'-methyl-6-(5-methyl-1,3,4-oxadiazol-2-yl) spiro [benzofuran-2,4'-cyclohex-2-ene]-1',3-dione (5a)

(2,4,6-trichlorophenyl) (2S,5'R)-7-chloro-1',4-dimethoxy-5'-methyl-3,3'-dioxo-spiro [benzofuran-2,6'-cyclohexene]-6-carboxylate (2,4,6-trichlorophenyl) (2S,5'R)-7-chloro-1',4-dimethoxy-5'-methyl-3,3'-dioxo-spiro [benzofuran-2,6'-cyclohexene]-6-carboxylate

[(2S,5'R)-7-chloro-1',4-dimethoxy-5'-methyl-3,3'-dioxo-spiro [benzofuran-2,6'-cyclohexene]-6-yl]trifluoromethanesulfonate (20 g) of example 3 (3a) was dissolved in toluene (200 mL), and palladium (II) acetate (0.477 g), 4,5-bis (diphenyl phosphino)-9,9-dimethylxanthene (2.46 g), and N,N-diisopropylethylamine (14.8 mL) were added and heated to 80° C. 2,4,6-trichlorophenyl formate (12.5 g) was added in three portions every 30 min.

After stirring at 80° C. for 30 min, the reaction mixture was poured into water, and the reaction mixture was extracted with ethyl acetate. The organic layer was washed with water and saturated saline and dried with anhydrous sodium sulfate. The residue, which was obtained by distilling the solvent under reduced pressure, was purified by silica gel column chromatography [elution solvent: n-hexane/ethyl acetate=7/3 to 3/7 (V/V)] to obtain 19.5 g (yield: 84%) of the title compound as a white solid.

(5b)

(2S,5'R)—N'-acetyl-7-chloro-1',4-dimethoxy-5'-methyl-3,3'-dioxo-spiro [benzofuran-2,6'-cyclohexene]-6-carbohydrazide (2S,5'R)—N'-acetyl-7-chloro-1',4-dimethoxy-5'-methyl-3,3'-dioxo-spiro [benzofuran-2,6'-cyclohexene]-6-carbohydrazide (2,4,6-trichlorophenyl) (2S,5'R)-7-chloro-1',4-dimethoxy-5'-methyl-3,3'-dioxo-spiro [benzofuran-2,6'-cyclohexene]-6-carboxylate (35 g) of example 5 (5a) was dissolved in dichloromethane (400 mL); 3H-1,2,3-triazolo [4,5-b] pyridine-3-ol (8.72 g), acetohydrazide (purity: 90%, 7.12 g), 4-dimethylaminopyridine (0.783 g), and triethylamine (26.8 mL) were added; and the mixture was allowed to stand at room temperature overnight.

The reaction solution was washed with water and saturated saline and dried with anhydrous sodium sulfate. The residue, which was obtained by distilling the solvent under reduced pressure, was purified by silica gel column chromatography [elution solvent: methanol/ethyl acetate=0/10 to 1/9 (V/V)] to obtain 23.4 g (yield: 86%) of the title compound as a white solid.

(5c)

(2S,5'R)-7-chloro-3',4-dimethoxy-5'-methyl-6-(5-methyl-1,3,4-oxadiazol-2-yl) spiro [benzofuran-2,4'-cyclohex-2-ene]-1',3-dione (2S,5'R)-7-chloro-3',4-dimethoxy-5'-methyl-6-(5-methyl-1,3,4-oxadiazol-2-yl) spiro [benzofuran-2,4'-cyclohex-2-ene]-1',3-dione (2S,5'R)—N'-acetyl-7-chloro-1',4-dimethoxy-5'-methyl-3,3'-dioxo-spiro [benzofuran-2,6'-cyclohexene]-6-carbohydrazide (0.25 g) of example 5 (5b) was dissolved in toluene (5 mL) and anhydrous 1,4-dioxane (5 mL), a (methoxycarbonyl sulfamoyl) triethylammonium hydroxide inner salt (0.169 g) was added, and the mixture was stirred at 60° C. for one hour.

Water was added to the reaction mixture, and the reaction mixture was extracted with ethyl acetate. The organic layer was washed with saturated saline and dried with anhydrous sodium sulfate. The residue, which was obtained by distilling the solvent under reduced pressure, was purified by silica gel column chromatography [elution solvent: n-hexane/ethyl acetate=1/1 to 0/1 (V/V)] to obtain 49 mg (yield: 20%) of the title compound as a white solid.

Example 6

(2S,5'R)-7-chloro-3',4-dimethoxy-5'-methyl-6-(3-methyl-1,2,4-oxadiazol-5-yl) spiro [benzofuran-2,4'-cyclohex-2-ene]-1',3-dione (6a)

[(Z)-1-aminoethylideneamino] (2S,5'R)-7-chloro-1',4-dimethoxy-5'-methyl-3,3'-dioxo-spiro [benzofuran-2,6'-cyclohexene]-6-carboxylate

[(Z)-1-aminoethylideneamino] (2S,5'R)-7-chloro-1',4-dimethoxy-5'-methyl-3,3'-dioxo-spiro [benzofuran-2,6'-cyclohexene]-6-carboxylate (2,4,6-trichlorophenyl) (2S,5'R)-7-chloro-1',4-dimethoxy-5'-methyl-3,3'-dioxo-spiro [benzofuran-2,6'-cyclohexene]-6-carboxylate (3 g) of example 5 (5a) was dissolved in dichloromethane (50 mL); N'-hydroxyethanimidamide (0.488 g), 3H-1,2,3-triazolo [4,5-b] pyridine-3-ol (0.748 g), 4-dimethylaminopyridine (0.0671 g), and triethylamine (2.28 mL) were added; and the mixture was allowed to stand at room temperature overnight.

The reaction solution was diluted with ethyl acetate, and the organic layer was washed with water and saturated saline and dried with anhydrous sodium sulfate. The residue, which was obtained by distilling the solvent under reduced pressure, was purified by silica gel column chromatography [elution solvent: n-hexane/ethyl acetate=80/20 to 0/100 (V/V)] to obtain 2.32 g (yield: quantitative) of the title compound as a white solid.

(6b)

(2S,5'R)-7-chloro-3',4-dimethoxy-5'-methyl-6-(3-methyl-1,2,4-oxadiazol-5-yl) spiro [benzofuran-2,4'-cyclohex-2-ene]-1',3-dione (2S,5'R)-7-chloro-3',4-dimethoxy-5'-methyl-6-(3-methyl-1,2,4-oxadiazol-5-yl) spiro [benzofuran-2,4'-cyclohex-2-ene]-1',3-dione

[(Z)-1-aminoethylideneamino] (2S,5'R)-7-chloro-1',4-dimethoxy-5'-methyl-3,3'-dioxo-spiro [benzofuran-2,6'-cyclohexene]-6-carboxylate (0.95 g) of example 6 (6a) was dissolved in toluene (20 mL) and stirred at 110° C. for six hours.

The residue obtained by concentrating the reaction solution was purified by silica gel column chromatography [elution solvent: n-hexane/ethyl acetate=8/2 to 3/7 (V/V)], and trituration was carried out with n-hexane and ethyl acetate to obtain 756 mg (yield: 83%) of the title compound as a white solid.

Example 7

(2S,5'R)-7-chloro-3',4-dimethoxy-5'-methyl-6-(5-methyl-1,2,4-oxadiazol-3-yl) spiro [benzofuran-2,4'-cyclohex-2-ene]-1',3-dione (7a)

(2S,5'R)-7-chloro-1',4-dimethoxy-5'-methyl-3,3'-dioxo-spiro [benzofuran-2,6'-cyclohexene]-6-carbonitrile (2S,5'R)-7-chloro-1',4-dimethoxy-5'-methyl-3,3'-dioxo-spiro [benzofuran-2,6'-cyclohexene]-6-carbonitrile

[(2S,5'R)-7-chloro-1',4-dimethoxy-5'-methyl-3,3'-dioxo-spiro [benzofuran-2,6'-cyclohexene]-6-yl]trifluoromethanesulfonate (1 g) of example 3 (3a) was dissolved in N,N-dimethylformamide (10 mL), tetrakis (triphenyl phosphine) palladium (0) (0.245 g) and zinc cyanide (0.499 g) were added, and the mixture was stirred at 90° C. for five hours.

The reaction mixture was poured into water, and the reaction mixture was extracted with ethyl acetate. The organic layer was washed with water and saturated saline and dried with anhydrous sodium sulfate. The residue, which was obtained by distilling the solvent under reduced pressure, was purified by silica gel column chromatography [elution solvent: n-hexane/ethyl acetate=8/2 to 3/7 (V/V)] to obtain 540 mg (yield: 73%) of the title compound as a pale yellow solid.

(7b)

(2S,5'R)-7-chloro-3',4-dimethoxy-5'-methyl-6-(5-methyl-1,2,4-oxadiazol-3-yl) spiro [benzofuran-2,4'-cyclohex-2-ene]-1',3-dione (2S,5'R)-7-chloro-3',4-dimethoxy-5'-methyl-6-(5-methyl-1,2,4-oxadiazol-3-yl) spiro [benzofuran-2,4'-cyclohex-2-ene]-1',3-dione (2S,5'R)-7-chloro-1',4-dimethoxy-5'-methyl-3,3'-dioxo-spiro [benzofuran-2,6'-cyclohexene]-6-carbonitrile (0.54 g) of example 7 (7a) was dissolved in ethanol (10 mL), 50% hydroxylamine aqueous solution (0.19 mL) was added, and the mixture was stirred at 90° C. for six hours.

The reaction solution was concentrated and azeotroped twice with toluene. The residue was dissolved in dichloromethane (20 mL); acetic acid (0.0891 mL), 1-ethyl-3-(3-dimethylaminopropyl) carbodiimide hydrochloride (0.299 g), 3H-1,2,3-triazolo [4,5-b] pyridine-3-ol (0.0424 g), and triethylamine (0.652 mL) were added; and the mixture was stirred at room temperature for five hours.

The reaction solution was diluted with dichloromethane, and the organic layer was washed with water and saturated saline and dried with anhydrous sodium sulfate. The residue, which was obtained by distilling the solvent under reduced pressure was roughly purified by silica gel column chromatography [elution solvent: n-hexane/ethyl acetate=1/1 to 0/1 (V/V)]. The obtained crude product was suspended in toluene (5 mL) and stirred at 100° C. for seven hours.

Water was added to the reaction mixture, and the reaction mixture was extracted with ethyl acetate. The organic layer was washed with water and saturated saline and dried with anhydrous sodium sulfate. The residue, which was obtained by distilling the solvent under reduced pressure, was purified by silica gel column chromatography [elution solvent: n-hexane/ethyl acetate=7/3 to 2/8 (V/V)] to obtain 34 mg (yield: 5.4%, three steps) of the title compound as a white solid.

Example 8

(2S,5'R)-7-chloro-6-[5-(1-hydroxy-1-methyl-ethyl)-1,3,4-oxadiazol-2-yl]-3',4-dimethoxy-5'-methyl-spiro [benzofuran-2,4'-cyclohex-2-ene]-1',3-dione (8a)

(2S,5'R)-7-chloro-N'-(2-hydroxy-2-methyl-propanoyl)-1',4-dimethoxy-5'-methyl-3,3'-dioxo-spiro [benzofuran-2,6'-cyclohexene]-6-carbohydrazide (2S,5'R)-7-chloro-N'-(2-hydroxy-2-methyl-propanoyl)-1',4-dimethoxy-5'-methyl-3,3'-dioxo-spiro [benzofuran-2,6'-cyclohexene]-6-carbohydrazide (2,4,6-trichlorophenyl) (2S,5'R)-7-chloro-1',4-dimethoxy-5'-methyl-3,3'-dioxo-spiro [benzofuran-2,6'-cyclohexene]-6-carboxylate (0.5 g) of example 5 (5a) was dissolved in dichloromethane (10 mL); 2-hydroxy-2-methylpropanohydrazide (0.162 g), 3H-1,2,3-triazolo [4,5-b] pyridine-3-ol (0.125 g), 4-dimethylaminopyridine (0.0224 g), and triethylamine (0.639 mL) were added; and the mixture was allowed to stand at room temperature overnight.

The residue, which was obtained by distilling the solvent under reduced pressure, was purified by silica gel column chromatography [elution solvent: methanol/ethyl acetate=0/10 to 1/9 (V/V)] to obtain 415 mg (yield: 97%) of the title compound as a white solid.

(8b)

(2S,5' R)-7-chloro-6-[5-(1-hydroxy-1-methyl-ethyl)-1,3,4-oxadiazol-2-yl]-3',4-dimethoxy-5'-methyl-spiro [benzofuran-2,4'-cyclohex-2-ene]-1',3-dione (2S,5'R)-7-chloro-6-[5-(1-hydroxy-1-methyl-ethyl)-1,3,4-oxadiazol-2-yl]-3',4-dimethoxy-5'-methyl-spiro [benzofuran-2,4'-cyclohex-2-ene]-1',3-dione (2S,5'R)-7-chloro-N'-(2-hydroxy-2-methyl-propanoyl)-1',4-dimethoxy-5'-methyl-3,3'-dioxo-spiro [benzofuran-2,6'-cyclohexene]-6-carbohydrazide (0.415 g) of example 8 (8a) was dissolved in dichloromethane (5 mL), triethylamine (0.62 mL) and p-toluene sulfonyl chloride (0.254 g) were added, and the mixture was stirred at room temperature for two hours.

The reaction mixture was poured into water, and the reaction mixture was extracted with ethyl acetate. The organic layer was washed with water and saturated saline and dried with anhydrous sodium sulfate. The residue, which was obtained by distilling the solvent under reduced pressure, was purified by silica gel column chromatography [elution solvent: methanol/ethyl acetate=0/10 to 1/9 (V/V)] to obtain 141 mg (yield: 35%) of the title compound as a white solid.

Example 9

(2S,5'R)-7-chloro-6-[5-[(1S)-1-hydroxyethyl]-1,3,4-oxadiazol-2-yl]-3',4-dimethoxy-5'-methyl-spiro [benzofuran-2,4'-cyclohex-2-ene]-1',3-dione (9a)

(2S)-2-tetrahydropyran-2-yloxypropanehydrazide (2S)-2-tetrahydropyran-2-yloxypropanehydrazide Methyl (2S)-2-tetrahydropyran-2-yloxypropanoate (CAS Registry Number: 153829-63-1, J. Org. Chem. 1991, 56, 1088-1093.) (2.2 g) was dissolved in ethanol (8 mL), hydrazine monohydrate (1.8 g) was added, and the mixture was allowed to stand overnight at room temperature. The residue, which was obtained by distilling the solvent under reduced pressure, was purified by silica gel column chromatography [elution solvent: methanol/ethyl acetate=0/10 to 1/9 (V/V)] to obtain 1.6 g (yield: 73%) of the title compound as a white solid.

(9b)

(2S,5'R)-7-chloro-1',4-dimethoxy-5'-methyl-3,3'-dioxo-N'-[(2S)-2-tetrahydropyran-2-yloxypropanoyl] spiro [benzofuran-2,6'-cyclohexene]-6-carbohydrazide (2S,5'R)-7-chloro-1',4-dimethoxy-5'-methyl-3,3'-dioxo-N'-[(2S)-2-tetrahydropyran-2-yloxypropanoyl] spiro [benzofuran-2,6'-cyclohexene]-6-carbohydrazide (2,4,6-trichlorophenyl) (2S,5'R)-7-chloro-1',4-dimethoxy-5'-methyl-3,3'-dioxo-spiro [benzofuran-2,6'-cyclohexene]-6-carboxylate (0.5 g) of example 5 (5a) was dissolved in dichloromethane (10 mL); (2S)-2-tetrahydropyran-2-yloxypropanehydrazide (0.258 g) of example 9 (9a), 3H-1,2,3-triazolo [4,5-b] pyridine-3-ol (0.125 g), 4-dimethylaminopyridine (0.0112 g), and N,N-diisopropylethylamine (0.478 mL) were added; and the mixture was allowed to stand at room temperature overnight.

The reaction mixture was poured into water and neutralized with 1 mol/L hydrochloric acid, and the reaction mixture was extracted with ethyl acetate.

The organic layer was washed with water and saturated saline and dried with anhydrous sodium sulfate. The residue, which was obtained by distilling the solvent under reduced pressure, was purified by silica gel column chromatography [elution solvent: n-hexane/ethyl acetate=1/1 to 0/1 (V/V)] to obtain 490 mg (yield: quantitative) of the title compound as a white solid.

(9c)

(2S,5'R)-7-chloro-3',4-dimethoxy-5'-methyl-6-[5-[(1S)-1-tetrahydropyran-2-yloxyethyl]-1,3,4-oxadiazol-2- yl]spiro [benzofuran-2,4'-cyclohex-2-ene]-1', 3-dione (2S,5'R)-7-chloro-3',4-dimethoxy-5'-methyl-6-[5-[(1S)-1-tetrahydropyran-2-yloxyethyl]-1,3,4-oxadiazol-2- yl]spiro [benzofuran-2,4'-cyclohex-2-ene]-1', 3-dione (2S,5'R)-7-chloro-1',4-dimethoxy-5'-methyl-3,3'-dioxo-N'-[(2S)-2-tetrahydropyran-2-yloxypropanoyl] spiro [benzofuran-2,6'-cyclohexene]-6-carbohydrazide (0.49 g) of example 9 (9b) was dissolved in dichloromethane (5 mL), triethylamine (0.637 mL) and p-toluene sulfonyl chloride (0.209 g) were added, and the mixture was stirred at room temperature for three hours.

The reaction mixture was poured into water and neutralized with 1 mol/L hydrochloric acid, and the reaction mixture was extracted with ethyl acetate. The organic layer was washed with water and saturated saline and dried with anhydrous sodium sulfate. The residue, which was obtained by distilling the solvent under reduced pressure, was purified by silica gel column chromatography [elution solvent: n-hexane/ethyl acetate=1/I to 0/1 (V/V)] to obtain 452 mg (yield: 95%) of the title compound as a white solid.

(9d)

(2S,5'R)-7-chloro-6-[5-[(1S)-1-hydroxyethyl]-1,3,4-oxadiazol-2-yl]-3',4-dimethoxy-5'-methyl-spiro [benzofuran-2,4'-cyclohex-2-ene]-1',3-dione (2S,5'R)-7-chloro-6-[5-[(1S)-1-hydroxyethyl]-1,3,4-oxadiazol-2-yl]-3',4-dimethoxy-5'-methyl-spiro [benzofuran-2,4'-cyclohex-2-ene]-1',3-dione (2S,5'R)-7-chloro-3',4-dimethoxy-5'-methyl-6-[5-[(1S)-1-tetrahydropyran-2-yloxyethyl]-1,3,4-oxadiazol-2-yl] spiro [benzofuran-2,4'-cyclohex-2-ene]-1',3-dione (0.452 g) of example 9 (9c) was dissolved in ethanol (4 mL), water (1 mL) and p-toluene sulfonic acid monohydrate (0.0828 g) were added, and the mixture was stirred at 50° C. for one hour.

The reaction mixture was poured into water, 1 mol/L hydrochloric acid was added, and the reaction mixture was extracted with ethyl acetate. The organic layer was washed with water and saturated saline and dried with anhydrous sodium sulfate. The residue, which was obtained by distilling the solvent under reduced pressure, was purified by silica gel column chromatography [elution solvent: methanol/ethyl acetate=0/1 to 1/19 (V/V)] to obtain 119 mg (yield: 31%) of the title compound as a white solid.

Example 10

(2S,5'R)-7-chloro-6-[5-[(1R)-1-hydroxyethyl]-1,3,4-oxadiazol-2-yl]-3',4-dimethoxy-5'-methyl-spiro [benzofuran-2,4'-cyclohex-2-ene]-1',3-dione (10a)

(2R)-2-tetrahydropyran-2-yloxypropanehydrazide (2R)-2-tetrahydropyran-2-yloxypropanehydrazide Methyl (2R)-2-tetrahydropyran-2-yloxypropanoate (CAS Registry Number: 124508-74-3, Tetrahedron, 2012, 68, 2068-2073.) (1.6 g) was dissolved in ethanol (8 mL), hydrazine monohydrate (1.2 mL) was added, and the mixture was stirred at 90° C. for four hours.

After standing at room temperature overnight, the mixture was stirred at 90° C. for 10 hours. The mixture was further allowed to stand at room temperature overnight and then stirred at 90° C. for 10 hours. The residue, which was obtained by distilling the solvent under reduced pressure, was purified by silica gel column chromatography [elution solvent: methanol/ethyl acetate=0/1 to 1/9 (V/V)] to obtain 1 g (yield: 62%) of the title compound as a white solid.

(10b)

(2S,5'R)-7-chloro-1',4-dimethoxy-5'-methyl-3,3'-dioxo-N'-[(2R)-2-tetrahydropyran-2-yloxypropanoyl] spiro [benzofuran-2,6'-cyclohexene]-6-carbohydrazide (2S,5'R)-7-chloro-1',4-dimethoxy-5'-methyl-3,3'-dioxo-N'-[(2R)-2-tetrahydropyran-2-yloxypropanoyl] spiro [benzofuran-2,6'-cyclohexene]-6-carbohydrazide (2,4,6-trichlorophenyl) (2S,5'R)-7-chloro-1',4-dimethoxy-5'-methyl-3,3'-dioxo-spiro [benzofuran-2,6'-cyclohexene]-6-carboxylate (0.5 g) of example 5 (5a) was dissolved in dichloromethane (10 mL); (2R)-2-tetrahydropyran-2-yloxypropanehydrazide (0.19 g) of example 10 (10a), 3H-1,2,3-triazolo [4,5-b] pyridine-3-ol (0.124 g), 4-dimethylaminopyridine (0.0112 g), and N,N-diisopropylethylamine (0.478 mL) were added; and the mixture was allowed to stand at room temperature overnight.

The reaction mixture was poured into water and neutralized with 1 mol/L hydrochloric acid, and the reaction mixture was extracted with ethyl acetate. The organic layer was washed with water and saturated saline and dried with anhydrous sodium sulfate. The residue, which was obtained by distilling the solvent under reduced pressure, was purified by silica gel column chromatography [elution solvent: methanol/ethyl acetate=0/10 to 1/9 (V/V)] to obtain 460 mg (yield: 94%) of the title compound as a white solid.

(10c)

(2S,5'R)-7-chloro-3',4-dimethoxy-5'-methyl-6-[5-[(1R)-1-tetrahydropyran-2-yloxyethyl]-1,3,4-oxadiazol-2- yl]spiro [benzofuran-2,4'-cyclohex-2-ene]-1', 3-dione (2S,5'R)-7-chloro-3',4-dimethoxy-5'-methyl-6-[5-[(1R)-1-tetrahydropyran-2-yloxyethyl]-1,3,4-oxadiazol-2- yl]spiro [benzofuran-2,4'-cyclohex-2-ene]-1', 3-dione (2S,5'R)-7-chloro-1',4-dimethoxy-5'-methyl-3,3'-dioxo-N'-[(2R)-2-tetrahydropyran-2-yloxypropanoyl] spiro [benzofuran-2,6'-cyclohexene]-6-carbohydrazide (0.46 g) of example 10 (10b) was dissolved in dichloromethane (5 mL), triethylamine (0.598 mL) and p-toluene sulfonyl chloride (0.196 g) were added, and the mixture was stirred at room temperature for two hours.

The reaction mixture was poured into water and neutralized with 1 mol/L hydrochloric acid, and the reaction mixture was extracted with ethyl acetate. The organic layer was washed with water and saturated saline and dried with anhydrous sodium sulfate. The residue, which was obtained by distilling the solvent under reduced pressure, was purified by silica gel column chromatography [elution solvent: n-hexane/ethyl acetate=1/1 to 0/1 (V/V)] to obtain 315 mg (yield: 71%) of the title compound as a white solid.

(10d)

(2S,5'R)-7-chloro-6-[5-[(1R)-1-hydroxyethyl]-1,3,4-oxadiazol-2-yl]-3',4-dimethoxy-5'-methyl-spiro [benzofuran-2,4'-cyclohex-2-ene]-1',3-dione (2S,5'R)-7-chloro-6-[5-[(1R)-1-hydroxyethyl]-1,3,4-oxadiazol-2-yl]-3',4-dimethoxy-5'-methyl-spiro [benzofuran-2,4'-cyclohex-2-ene]-1',3-dione (2S,5'R)-7-chloro-3',4-dimethoxy-5'-methyl-6-[5-[(1R)-1-tetrahydropyran-2-yloxyethyl]-1,3,4-oxadiazol-2-yl]

spiro [benzofuran-2,4'-cyclohex-2-ene]-1',3-dione (0.315 g) of example 10 (10c) was dissolved in ethanol (4 mL), water (1 mL) and p-toluene sulfonic acid monohydrate (0.0577 g) were added, and the mixture was stirred at 50° C. for one hour.

The reaction mixture was poured into water, 1 mol/L hydrochloric acid was added, and the reaction mixture was extracted with ethyl acetate. The organic layer was washed with water and saturated saline and dried with anhydrous sodium sulfate. The residue, which was obtained by distilling the solvent under reduced pressure, was purified by silica gel column chromatography [elution solvent: methanol/ethyl acetate=0/10 to 1/19 (V/V)] to obtain 112 mg (yield: 42%) of the title compound as a white solid.

Example 11

(2S,5'R)-7-chloro-4-ethoxy-6-[5-(1-hydroxy-1-methyl-ethyl)-1,3,4-oxadiazol-2-yl]-3'-methoxy-5'-methyl-spiro [benzofuran-2,4'-cyclohex-2-ene]-1',3-dione (11a)

(2S,5'R)-7-chloro-4-hydroxy-6-[5-(1-hydroxy-1-methyl-ethyl)-1,3,4-oxadiazol-2-yl]-3'-methoxy-5'-methyl- spiro [benzofuran-2,4'-cyclohex-2-ene]-1',3-dione (2S,5'R)-7-chloro-4-hydroxy-6-[5-(1-hydroxy-1-methyl-ethyl)-1,3,4-oxadiazol-2-yl]-3'-methoxy-5'-methyl- spiro [benzofuran-2,4'-cyclohex-2-ene]-1',3-dione Magnesium in a scraped form (0.41 g) was added to diethyl ether (60 mL), and iodine (3.9 g) was added in three portions every 20 min. After stirring at room temperature for one hour, (2S,5'R)-7-chloro-6-[5-(1-hydroxy-1-methyl-ethyl)-1,3,4-oxadiazol-2-yl]-3',4-dimethoxy-5'-methyl-spiro [benzofuran-2,4'-cyclohex-2-ene]-1',3-dione (6.3 g) of example 8 (8b) and toluene (150 mL) were added, and the mixture was stirred at 90° C. for seven hours.

Water was added to the reaction mixture, and after neutralization with 1 mol/L hydrochloric acid, the mixture was made weakly basic with saturated sodium bicarbonate aqueous solution, and the reaction mixture was extracted with ethyl acetate. The organic layer was washed with 1 mol/L hydrochloric acid and saturated saline and dried with anhydrous sodium sulfate. The residue, which was obtained by distilling the solvent under reduced pressure, was purified by silica gel column chromatography [elution solvent: n-hexane/ethyl acetate=1/1 to 0/1 (V/V)] to obtain 2.7 g (yield: 44%) of the title compound as a white solid.

(11b)

(2S,5'R)-7-chloro-4-ethoxy-6-[5-(1-hydroxy-1-methyl-ethyl)-1,3,4-oxadiazol-2-yl]-3'-methoxy-5'-methyl-spiro [benzofuran-2,4'-cyclohex-2-ene]-1',3-dione (2S,5'R)-7-chloro-4-ethoxy-6-[5-(1-hydroxy-1-methyl-ethyl)-1,3,4-oxadiazol-2-yl]-3'-methoxy-5'-methyl-spiro [benzofuran-2,4'-cyclohex-2-ene]-1',3-dione (2S,5'R)-7-chloro-4-hydroxy-6-[5-(1-hydroxy-1-methyl-ethyl)-1,3,4-oxadiazol-2-yl]-3'-methoxy-5'-methyl-spiro [benzofuran-2,4'-cyclohex-2-ene]-1',3-dione (0.3 g) of example 11 (11a) was dissolved in N,N-dimethylformamide (4 mL); potassium carbonate (0.191 g) and iodoethane (0.0827 mL) were added; and the mixture was stirred at 80° C. for two hours.

The reaction mixture was poured into water and neutralized with 1 mol/L hydrochloric acid, and the reaction mixture was extracted with ethyl acetate. The organic layer was washed with water and saturated saline and dried with anhydrous sodium sulfate. The residue, which was obtained by distilling the solvent under reduced pressure, was purified by silica gel column chromatography [elution solvent: n-hexane/ethyl acetate=6/4 to 1/9 (V/V)] to obtain 42 mg (yield: 13%) of the title compound as a white solid.

Example 12

(2S,5'R)-7-chloro-4-ethoxy-6-[5-[(1S)-1-hydroxyethyl]-1,3,4-oxadiazol-2-yl]-3'-methoxy-5'-methyl-spiro [benzofuran-2,4'-cyclohex-2-ene]-1',3-dione (2S,5'R)-7-chloro-4-ethoxy-6-[5-[(1S)-1-hydroxyethyl]-1,3,4-oxadiazol-2-yl]-3'-methoxy-5'-methyl-spiro [benzofuran-2,4'-cyclohex-2-ene]-1',3-dione Magnesium in a scraped form (0.073 g) was added to diethyl ether (20 mL), a small amount of iodine (0.70 g) was added, and the mixture was stirred at room temperature for 10 min. Furthermore, iodine (0.70 g) was added in three portions every 20 min. After stirring at room temperature for 30 min, toluene (50 mL), (2S,5'R)-7-chloro-3',4-dimethoxy-5'-methyl-6-[5-[(1S)-1-tetrahydropyran-2-yloxyethyl]-1,3,4-oxadiazol-2-yl]spiro [benzofuran-2,4'-cyclohex-2-ene]-1',3-dione (1.3 g) of example 9 (9c) was added and stirred at 80° C. for eight hours.

Water was added to the reaction mixture, the reaction mixture was neutralized with 1 mol/L hydrochloric acid, and the reaction mixture was extracted with ethyl acetate. The organic layer was washed with saturated saline and dried with anhydrous sodium sulfate. The residue, which was obtained by distilling the solvent under reduced pressure, was dissolved in N,N-dimethylformamide (10 mL), potassium carbonate (1.36 g) and iodoethane (0.485 mL) were added, and the mixture was stirred at 80° C. for one hour. The reaction mixture was poured into water and neutralized with 1 mol/L hydrochloric acid, and the reaction mixture was extracted with ethyl acetate. The organic layer was washed with water and saturated saline and dried with anhydrous sodium sulfate. The residue, which was obtained by distilling the solvent under reduced pressure, was purified by silica gel column chromatography [elution solvent: n-hexane/ethyl acetate=7/3 to 2/8 (V/V)], and the obtained solid was triturated with n-hexane and ethyl acetate to obtain 122 mg (yield: 13%) of the title compound as a white solid.

Example 13

(2S,5'R)-7-chloro-6-[3-(1-hydroxyethyl)-1,2,4-oxadiazol-5-yl]-3',4-dimethoxy-5'-methyl-spiro [benzofuran-2,4'-cyclohex-2-ene]-1',3-dione (13a)

2-tetrahydropyran-2-yloxypropanenitrile 2-tetrahydropyran-2-yloxypropanenitrile 2-hydroxypropanenitrile (5.0 g) was dissolved in dichloromethane (150 mL), 3,4-dihydro-2H-pyran (7.7 g) and p-toluene sulfonic acid monohydrate (1.3 g) were added, and the mixture was stirred at room temperature for 14 hours. After adding triethylamine to the reaction solution, the solvent was distilled under reduced pressure, the obtained residue was purified by silica gel column chromatography [elution solvent: n-hexane/ethyl acetate=97/3 to 7/3 (V/V)], and the title compound was obtained as two types of diastereomers that were 5.7 g (low polarity, yield: 52%) and 2.5 g (high polarity, yield: 23%), respectively. They were pale yellow solids.

(13b)

N'-hydroxy-2-tetrahydropyran-2-yloxy-propanamidine

N'-hydroxy-2-tetrahydropyran-2-yloxy-propanamidine

The low polar diastereomer, 2-tetrahydropyran-2-yloxy-propanenitrile (5.6 g) obtained in example 13 (13a) was dissolved in ethanol (36 mL), 50% hydroxylamine aqueous solution (4.3 mL) was added, and the mixture was heated to 80° C. and stirred for five hours. After returning to room temperature, the solvent was distilled under reduced pressure, and the obtained residue was purified by silica gel column chromatography [elution solvent: n-hexane/ethyl acetate=10/1 to 0/1 (V/V)] to obtain 5.0 g (yield: 74%) of the title compound as a pale yellow solid.

(13c)

[(Z)-(1-amino-2-tetrahydropyran-2-yloxy-propylidene) amino] (2S,5'R)-7-chloro-1',4-dimethoxy-5'-methyl-3,3'-dioxo-spiro [benzofuran-2,6'-cyclohexene]-6-carboxylate

[(Z)-(1-amino-2-tetrahydropyran-2-yloxy-propylidene) amino] (2S,5'R)-7-chloro-1',4-dimethoxy-5'-methyl-3,3'-dioxo-spiro [benzofuran-2,6'-cyclohexene]-6-carboxylate (2,4,6-trichlorophenyl) (2S,5'R)-7-chloro-1',4-dimethoxy-5'-methyl-3,3'-dioxo-spiro [benzofuran-2,6'-cyclohexene]-6-carboxylate (0.5 g) of example 5 (5a) was dissolved in dichloromethane (10 mL); N'-hydroxy-2-tetrahydropyran-2-yloxy-propanamidine (0.207 g) of example 13 (13b), 3H-1,2,3-triazolo [4,5-b]pyridine-3-ol (0.125 g), 4-dimethylaminopyridine (0.0112 g), and N,N-diisopropylethylamine (0.478 mL) were added; and the mixture was stirred at room temperature for five hours.

The reaction mixture was poured into water and neutralized with 1 mol/L hydrochloric acid, and the reaction mixture was extracted with ethyl acetate. The organic layer was washed with water and saturated saline and dried with anhydrous sodium sulfate. The residue, which was obtained by distilling the solvent under reduced pressure, was purified by silica gel column chromatography [elution solvent: n-hexane/ethyl acetate=1/1 to 0/1 (V/V)] to obtain 410 mg (yield: 83%) of the title compound as a white solid.

(13d)

(2S,5'R)-7-chloro-3',4-dimethoxy-5'-methyl-6-[3-(1-tetrahydropyran-2-yloxyethyl)-1,2,4-oxadiazol-5-yl] spiro [benzofuran-2,4'-cyclohex-2-ene]-1',3-dione (2S,5'R)-7-chloro-3',4-dimethoxy-5'-methyl-6-[3-(1-tetrahydropyran-2-yloxyethyl)-1,2,4-oxadiazol-5-yl] spiro [benzofuran-2,4'-cyclohex-2-ene]-1',3-dione

[(Z)-(1-amino-2-tetrahydropyran-2-yloxy-propylidene) amino] (2S,5'R)-7-chloro-1',4-dimethoxy-5'-methyl-3,3'-dioxo-spiro [benzofuran-2,6'-cyclohexene]-6-carboxylate (0.41 g) of example 13 (13c) was dissolved in toluene (5 mL) and stirred at 110° C. for seven hours.

The residue, which was obtained by distilling the solvent under reduced pressure, was purified by silica gel column chromatography [elution solvent: n-hexane/ethyl acetate=1/1 to 1/9 (V/V)] to obtain 375 mg (yield: 95%) of the title compound as a white solid.

(13e)

(2S,5'R)-7-chloro-6-[3-(1-hydroxyethyl)-1,2,4-oxadiazol-5-yl]-3',4-dimethoxy-5'-methyl-spiro [benzofuran-2,4'-cyclohex-2-ene]-1',3-dione (2S,5'R)-7-chloro-6-[3-(1-hydroxyethyl)-1,2,4-oxadiazol-5-yl]-3',4-dimethoxy-5'-methyl-spiro [benzofuran-2,4'-cyclohex-2-ene]-1',3-dione (2S,5'R)-7-chloro-3',4-dimethoxy-5'-methyl-6-[3-(1-tetrahydropyran-2-yloxyethyl)-1,2,4-oxadiazol-5-yl] spiro [benzofuran-2,4'-cyclohex-2-ene]-1',3-dione (0.375 g) of example 13 (13d) was dissolved in ethanol (4 mL), p-toluene sulfonic acid monohydrate (0.0687 g) and water (1 mL) were added, and the mixture was stirred at room temperature for eight hours.

The reaction mixture was poured into water, and the reaction mixture was extracted with ethyl acetate. The organic layer was washed with water and saturated saline and dried with anhydrous sodium sulfate. The residue, which was obtained by distilling the solvent under reduced pressure, was purified by silica gel column chromatography [elution solvent: n-hexane/ethyl acetate=1/1 to 0/1 (V/V)] to obtain 195 mg (yield: 62%) of the title compound as a white solid.

Example 14

(2S,5'R)-7-chloro-4-(2-hydroxyethoxy)-3'-methoxy-5'-methyl-6-(5-methyl-1,3,4-oxadiazol-2-yl) spiro [benzofuran-2,4'-cyclohex-2-ene]-1',3-dione (14a)

(2S,5'R)-7-chloro-4-hydroxy-3',6-dimethoxy-5'-methyl-spiro [benzofuran-2,4'-cyclohex-2-ene]-1',3-dione (2S,5'R)-7-chloro-4-hydroxy-3',6-dimethoxy-5'-methyl-spiro [benzofuran-2,4'-cyclohex-2-ene]-1',3-dione Magnesium in a scraped form (1.03 g) was added to diethyl ether (50 mL), iodine (8.63 g) was added in small portions over one hour. After stirring at room temperature for 30 min, toluene (100 mL) and (+)-griseofulvin (10 g) were added, and the mixture was stirred at 80° C. for three hours.

Water was added to the reaction mixture, the mixture was neutralized with 1 mol/L hydrochloric acid, and the reaction mixture was extracted with ethyl acetate. The organic layer was washed with saturated saline and dried with anhydrous sodium sulfate. The residue, which was obtained by distilling the solvent under reduced pressure, was purified by silica gel column chromatography [elution solvent: n-hexane/ethyl acetate=1/1 to 0/1 (V/V)] to obtain 7.8 g (yield: 81%) of the title compound as a white solid.

(14b)

(2S,5'R)-7-chloro-3',6-dimethoxy-5'-methyl-4-(2-tetrahydropyran-2-yloxyethoxy) spiro [benzofuran-2,4'-cyclohex-2-ene]-1',3-dione (2S,5'R)-7-chloro-3',6-dimethoxy-5'-methyl-4-(2-tetrahydropyran-2-yloxyethoxy) spiro [benzofuran-2,4'-cyclohex-2-ene]-1',3-dione (2S,5'R)-7-chloro-4-hydroxy-3',6-dimethoxy-5'-methyl-spiro [benzofuran-2,4'-cyclohex-2-ene]-1',3-dione (5.1 g) of example 14 (14a) was dissolved in N,N-dimethylformamide (60 mL), 2-(2-bromoethoxy) tetrahydro-2H-pyran (3.8 g) and potassium carbonate (6.2 g) were added, and the mixture was stirred at 80° C. for seven hours.

The reaction mixture was poured into water, and the reaction mixture was extracted with ethyl acetate. The organic layer was washed with water and saturated saline and dried with anhydrous sodium sulfate. The residue, which was obtained by distilling the solvent under reduced pressure, was purified by silica gel column chromatography [elution solvent: n-hexane/ethyl acetate=8/2 to 3/7 (V/V)] to obtain 6.9 g (yield: 98%) of the title compound as a white solid.

(14c)

(2S,5'R)-7-chloro-6-hydroxy-3'-methoxy-5'-methyl-4-(2-tetrahydropyran-2-yloxyethoxy) spiro [benzofuran-2,4'-cyclohex-2-ene]-1',3-dione (2S,5'R)-7-chloro-6-hydroxy-3'-methoxy-5'-methyl-4-(2-tetrahydropyran-2-yloxyethoxy) spiro [benzofuran-2,4'-cyclohex-2-ene]-1',3-dione (2S,5'R)-7-chloro-3',6-dimethoxy-5'-methyl-4-(2-tetrahydropyran-2-yloxyethoxy) spiro [benzofuran-2,4'-cyclohex-2-ene]-1',3-dione (6.9 g) of example 14 (14b) was dissolved in pyridine (70 mL), 18-crown 6-ether (4.3 g) and potassium iodide (2.5 g) were added, and the mixture was stirred at 120° C. for eight hours.

The reaction solution was concentrated, and the reaction mixture was poured into water and extracted with ethyl acetate. The organic layer was washed with water and saturated saline and dried with anhydrous sodium sulfate. The residue, which was obtained by distilling the solvent under reduced pressure, was purified by silica gel column chromatography [elution solvent: n-hexane/ethyl acetate=1/1 to 0/1 (V/V)] to obtain 3.8 g (yield: 57%) of the title compound as a white solid.

(14d)

[(2S,5'R)-7-chloro-1'-methoxy-5'-methyl-3,3'-dioxo-4-(2-tetrahydropyran-2-yloxyethoxy) spiro [benzofuran-2,6'-cyclohexene]-6-yl] trifluoromethanesulfonate

[(2S,5'R)-7-chloro-1'-methoxy-5'-methyl-3,3'-dioxo-4-(2-tetrahydropyran-2-yloxyethoxy) spiro [benzofuran-2,6'-cyclohexene]-6-yl] trifluoromethanesulfonate (2S,5'R)-7-chloro-6-hydroxy-3'-methoxy-5'-methyl-4-(2-tetrahydropyran-2-yloxyethoxy) spiro [benzofuran-2,4'-cyclohex-2-ene]-1',3-dione (3.8 g) of example 14 (14c) was dissolved in dichloromethane (40 mL), triethylamine (2.9 mL) and N-phenylbis (trifluoromethanesulfonimide) (3.6 g) were added, and the mixture was allowed to stand at room temperature overnight.

The reaction solution was diluted with dichloromethane, and the organic layer was washed with water and saturated saline and dried with anhydrous sodium sulfate. The residue, which was obtained by distilling the solvent under reduced pressure, was purified by silica gel column chromatography [elution solvent: n-hexane/ethyl acetate=8/2 to 4/6 (V/V)] to obtain 3.2 g (yield: 65%) of the title compound as a white solid.

(14e)

(2,4,6-trichlorophenyl) (2S,5'R)-7-chloro-1'-methoxy-5'-methyl-3,3'-dioxo-4-(2-tetrahydropyran-2-yloxyethoxy) spiro [benzofuran-2,6'-cyclohexene]-6-carboxylate (2,4,6-trichlorophenyl) (2S,5'R)-7-chloro-1'-methoxy-5'-methyl-3,3'-dioxo-4-(2-tetrahydropyran-2-yloxyethoxy) spiro [benzofuran-2,6'-cyclohexene]-6-carboxylate

[(2S,5'R)-7-chloro-1'-methoxy-5'-methyl-3,3'-dioxo-4-(2-tetrahydropyran-2-yloxyethoxy) spiro [benzofuran-2,6'-cyclohexene]-6-yl] trifluoromethanesulfonate (1 g) of example 14 (14d) was dissolved in toluene (200 mL); palladium (II) acetate (0.0192 g), 4,5-bis (diphenyl phosphino)-9,9-dimethylxanthene (0.0989 g), and N,N-diisopropylethylamine (0.596 mL) were added; and the mixture was heated to 80° C.

2,4,6-trichlorophenyl formate (0.501 g) was added in three portions every 10 min. After stirring at 80° C. for 30 min, the reaction mixture was returned to room temperature, poured into water, and extracted with ethyl acetate. The organic layer was washed with water and saturated saline and dried with anhydrous sodium sulfate. The residue, which was obtained by distilling the solvent under reduced pressure, was purified by silica gel column chromatography [elution solvent: n-hexane/ethyl acetate=8/2 to 4/6 (V/V)] to obtain 850 mg (yield: 75%) of the title compound as a white solid.

(14f)

(2S,5'R)—N'-acetyl-7-chloro-1'-methoxy-5'-methyl-3,3'-dioxo-4-(2-tetrahydropyran-2-yloxyethoxy) spiro [benzofuran-2,6'-cyclohexene]-6-carbohydrazide (2S,5'R)—N'-acetyl-7-chloro-1'-methoxy-5'-methyl-3,3'-dioxo-4-(2-tetrahydropyran-2-yloxyethoxy) spiro [benzofuran-2,6'-cyclohexene]-6-carbohydrazide (2,4,6-trichlorophenyl) (2S,5'R)-7-chloro-1'-methoxy-5'-methyl-3,3'-dioxo-4-(2-tetrahydropyran-2-yloxyethoxy) spiro [benzofuran-2,6'-cyclohexene]-6-carboxylate (0.4 g) of example 14 (14e) was dissolved in dichloromethane (20 mL); acetohydrazine (purity: 90%, 0.0673 g), 3H-1,2,3-triazolo [4,5-b] pyridine-3-ol (0.0824 g), 4-dimethylaminopyridine (0.0148 g), and triethylamine (0.254 mL) were added; and the mixture was allowed to stand at room temperature overnight.

The reaction mixture was poured into water and neutralized with 1 mol/L hydrochloric acid, and the reaction mixture was extracted with ethyl acetate. The organic layer was washed with water and saturated saline and dried with anhydrous sodium sulfate. The residue, which was obtained by distilling the solvent under reduced pressure, was purified by silica gel column chromatography [elution solvent: methanol/ethyl acetate=0/10 to 1/9 (V/V)] to obtain 280 mg (yield: 86%) of the title compound as a white solid.

(14g)

(2S,5'R)-7-chloro-3'-methoxy-5'-methyl-6-(5-methyl-1,3,4-oxadiazol-2-yl)-4-(2-tetrahydropyran-2-yloxyethoxy) spiro [benzofuran-2,4'-cyclohex-2-ene]-1',3-dione (2S,5'R)-7-chloro-3'-methoxy-5'-methyl-6-(5-methyl-1,3,4-oxadiazol-2-yl)-4-(2-tetrahydropyran-2-yloxyethoxy) spiro [benzofuran-2,4'-cyclohex-2-ene]-1',3-dione (2S,5'R)—N'-acetyl-7-chloro-1'-methoxy-5'-methyl-3,3'-dioxo-4-(2-tetrahydropyran-2-yloxyethoxy) spiro [benzofuran-2,6'-cyclohexene]-6-carbohydrazide (0.28 g) of example 14 (14f) was dissolved in dichloromethane (5 mL), p-toluene sulfonyl chloride (0.149 g) and triethylamine (0.364 mL) were added and stirred at room temperature for three hours.

The reaction mixture was poured into water and extracted with ethyl acetate. The organic layer was washed with water and saturated saline and dried with anhydrous sodium sulfate. The residue, which was obtained by distilling the solvent under reduced pressure, was purified by silica gel column chromatography [elution solvent: n-hexane/ethyl acetate=1/1 to 0/1 (V/V)] to obtain 202 mg (yield: 75%) of the title compound as a white solid.

(14h)

(2S,5'R)-7-chloro-4-(2-hydroxyethoxy)-3'-methoxy-5'-methyl-6-(5-methyl-1,3,4-oxadiazol-2-yl) spiro [benzofuran-2,4'-cyclohex-2-ene]-1',3-dione (2S,5'R)-7-chloro-4-(2-hydroxyethoxy)-3'-methoxy-5'-methyl-6-(5-methyl-1,3,4-oxadiazol-2-yl) spiro [benzofuran-2,4'-cyclohex-2-ene]-1',3-dione (2S,5'R)-7-chloro-3'-methoxy-5'-methyl-6-(5-methyl-1,3,4-oxadiazol-2-yl)-4-(2-tetrahydropyran-2-yloxyethoxy) spiro [benzofuran-2,4'-cyclohex-2-ene]-1',3-dione (0.202 g) of example 14 (14g) was dissolved in ethanol (2 mL), p-toluene sulfonic acid monohydrate (0.037 g) and water (5 mL) were added, and the mixture was stirred at 50° C. for two hours.

The reaction mixture was poured into water and extracted with ethyl acetate. The organic layer was washed with water and saturated saline and dried with anhydrous sodium sulfate. The residue, which was obtained by distilling the solvent under reduced pressure, was purified by silica gel column chromatography [elution solvent: methanol/ethyl acetate=0/10 to 1/9 (V/V)] to obtain 39 mg (yield: 23%) of the title compound as a white solid.

Example 15

(2S,5'R)-7-chloro-4-(2-hydroxyethoxy)-3'-methoxy-5'-methyl-6-(3-methyl-1,2,4-oxadiazol-5-yl) spiro [benzofuran-2,4'-cyclohex-2-ene]-1',3-dione (15a)

[(Z)-1-aminoethylideneamino] (2S,5'R)-7-chloro-1'-methoxy-5'-methyl-3,3'-dioxo-4-(2-tetrahydropyran-2-yloxyethoxy) spiro [benzofuran-2,6'-cyclohexene]-6-carboxylate

[(Z)-1-aminoethylideneamino] (2S,5'R)-7-chloro-1'-methoxy-5'-methyl-3,3'-dioxo-4-(2-tetrahydropyran-2-yloxyethoxy) spiro [benzofuran-2,6'-cyclohexene]-6-carboxylate (2,4,6-trichlorophenyl) (2S,5'R)-7-chloro-1'-methoxy-5'-methyl-3,3'-dioxo-4-(2-tetrahydropyran-2-yloxyethoxy) spiro [benzofuran-2,6'-cyclohexene]-6-carboxylate (0.45 g) of example 14 (14e) was dissolved in dichloromethane (10 mL); N'-hydroxyethaneimidamide (0.0758 g), 3H-1,2,3-triazolo [4,5-b] pyridine-3-ol (0.0928 g), 4-dimethylaminopyridine (0.00833 g), and triethylamine (0.285 mL) were added; and the mixture was allowed to stand at room temperature overnight.

The reaction mixture was poured into water, and the reaction mixture was extracted with ethyl acetate. The organic layer was washed with water and saturated saline and dried with anhydrous sodium sulfate. The residue, which was obtained by distilling the solvent under reduced pressure, was purified by silica gel column chromatography [elution solvent: methanol/ethyl acetate=0/10 to 1/9 (V/V)] to obtain 345 mg (yield: 94%) of the title compound as a white solid.

(15b)

(2S,5'R)-7-chloro-3'-methoxy-5'-methyl-6-(3-methyl-1,2,4-oxadiazol-5-yl)-4-(2-tetrahydropyran-2-yloxyethoxy) spiro [benzofuran-2,4'-cyclohex-2-ene]-1',3-dione (2S,5'R)-7-chloro-3'-methoxy-5'-methyl-6-(3-methyl-1,2,4-oxadiazol-5-yl)-4-(2-tetrahydropyran-2-yloxyethoxy) spiro [benzofuran-2,4'-cyclohex-2-ene]-1',3-dione

[(Z)-1-aminoethylideneamino] (2S,5'R)-7-chloro-1'-methoxy-5'-methyl-3,3'-dioxo-4-(2-tetrahydropyran-2-yloxyethoxy) spiro [benzofuran-2,6'-cyclohexene]-6-carboxylate (0.345 g) of example 15 (15a) was suspended in toluene (5 mL) and stirred at 100° C. for five hours. The residue, which was obtained by distilling the solvent under reduced pressure, was purified by silica gel column chromatography [elution solvent: n-hexane/ethyl acetate=1/1 to 0/1 (V/V)] to obtain 283 mg (yield: 85%) of the title compound as a white solid.

(15c)

(2S,5'R)-7-chloro-4-(2-hydroxyethoxy)-3'-methoxy-5'-methyl-6-(3-methyl-1,2,4-oxadiazol-5-yl) spiro [benzofuran-2,4'-cyclohex-2-ene]-1',3-dione (2S,5'R)-7-chloro-4-(2-hydroxyethoxy)-3'-methoxy-5'-methyl-6-(3-methyl-1,2,4-oxadiazol-5-yl) spiro [benzofuran-2,4'-cyclohex-2-ene]-1',3-dione (2S,5'R)-7-chloro-3'-methoxy-5'-methyl-6-(3-methyl-1,2,4-oxadiazol-5-yl)-4-(2-tetrahydropyran-2-yloxyethoxy)

spiro [benzofuran-2,4'-cyclohex-2-ene]-1',3-dione (0.283 g) of example 15 (15b) was dissolved in ethanol (2 mL), p-toluene sulfonic acid monohydrate (0.0518 g) and water (5 mL) were added and stirred at 50° C. for three hours.

The reaction mixture was poured into water, and the reaction mixture was extracted with ethyl acetate. The organic layer was washed with water and saturated saline and dried with anhydrous sodium sulfate. The residue, which was obtained by distilling the solvent under reduced pressure, was purified by silica gel column chromatography [elution solvent: methanol/ethyl acetate=0/10 to 1/9 (V/V)] to obtain 128 mg (yield: 54%) of the title compound as a white solid.

Example 16

(2S,5'R)-7-chloro-4-(2-hydroxyethoxy)-3'-methoxy-5'-methyl-6-(5-methyl-1,2,4-oxadiazol-3-yl) spiro [benzofuran-2,4'-cyclohex-2-ene]-1',3-dione (16a)

(2S,5'R)-7-chloro-4-hydroxy-3'-methoxy-5'-methyl-6-(5-methyl-1,2,4-oxadiazol-3-yl) spiro [benzofuran-2,4'-cyclohex-2-ene]-1',3-dione (2S,5'R)-7-chloro-4-hydroxy-3'-methoxy-5'-methyl-6-(5-methyl-1,2,4-oxadiazol-3-yl) spiro [benzofuran-2,4'-cyclohex-2-ene]-1',3-dione (2S,5'R)-7-chloro-3',4-dimethoxy-5'-methyl-6-(5-methyl-1,2,4-oxadiazol-3-yl) spiro [benzofuran-2,4'-cyclohex-2-ene)-1',3-dione (2.3 g) of example 7 (7b) was dissolved in a mixed solvent of toluene (20 mL) and ether (40 mL), magnesium iodide (1.52 g) was added, and the mixture was stirred at 80° C. for five hours. Water was added to the reaction mixture, and after neutralization with 4N hydrochloric acid, the reaction mixture was extracted with ethyl acetate. The organic layer was washed with water and saturated saline and dried with anhydrous sodium sulfate. The residue, which was obtained by distilling the solvent under reduced pressure, was purified by silica gel column chromatography [elution solvent: petroleum ether/ethyl acetate=1/1 (V/V)] to obtain 1.7 g (yield: 64%) of the title compound as a yellow solid.

(16b)

(2S,5'R)-7-chloro-4-(2-hydroxyethoxy)-3'-methoxy-5'-methyl-6-(5-methyl-1,2,4-oxadiazol-3-yl) spiro [benzofuran-2,4'-cyclohex-2-ene]-1',3-dione (2S,5'R)-7-chloro-4-(2-hydroxyethoxy)-3'-methoxy-5'-methyl-6-(5-methyl-1,2,4-oxadiazol-3-yl) spiro [benzofuran-2,4'-cyclohex-2-ene]-1',3-dione Palladium chloride (0.45 mg) was dissolved in water (2 mL), and tetrabutylammonium bromide (10.3 mg) and potassium carbonate (4.42 mg) were added. After stirring at 60° C. for 15 minutes, (2S,5'R)-7-chloro-4-hydroxy-3'-methoxy-5'-methyl-6-(5-methyl-1,2,4-oxadiazol-3-yl) spiro [benzofuran-2,4'-cyclohex-2-ene]-1',3-dione (50 mg) of example 16 (16a) and oxirane (28.1 mg) were added, and the mixture was stirred at 60° C. for 12 hours.

The reaction mixture was poured into water, and the reaction mixture was extracted with dichloromethane. The organic layer was washed with water and saturated saline and dried with anhydrous sodium sulfate. The residue, which was obtained by distilling the solvent under reduced pressure, was purified by thin layer chromatography [developing solvent: ethyl acetate] to obtain 16 mg (yield: 29%) of the title compound as a yellow solid.

Example 17

(2S,5'R)-7-chloro-6-(5-ethyl-1,3,4-oxadiazol-2-yl)-3',4-dimethoxy-5'-methyl-spiro [benzofuran-2,4'-cyclohex-2-ene]-1',3-dione (17a)

(2S,5'R)-7-chloro-1',4-dimethoxy-5'-methyl-3,3'-dioxo-N'-propanoyl-spiro [benzofuran-2,6'-cyclohexene]-6-carbohydrazide (2S,5'R)-7-chloro-1',4-dimethoxy-5'-methyl-3,3'-dioxo-N'-propanoyl-spiro [benzofuran-2,6'-cyclohexene]-6-carbohydrazide (2,4,6-trichlorophenyl) (2S,5'R)-7-chloro-1',4-dimethoxy-5'-methyl-3,3'-dioxo-spiro [benzofuran-2,6'-cyclohexene]-6-carboxylate (0.50 g) of example 5 (5a) was dissolved in dichloromethane (20 mL), 3H-1,2,3-triazolo [4,5-b] pyridine-3-ol (0.12 g), propionohydrazide (purity: 90%, 0.097 g), 4-dimethylaminopyridine (0.011 g), and triethylamine (0.39 mL) were added, and the mixture was allowed to stand at room temperature overnight.

The reaction solution was washed with water and saturated saline and dried with anhydrous sodium sulfate. The solvent was distilled under reduced pressure to obtain 0.75 g of the crude title compound as a pale yellow solid.

(17b)

(2S,5'R)-7-chloro-6-(5-ethyl-1,3,4-oxadiazol-2-yl)-3',4-dimethoxy-5'-methyl-spiro [benzofuran-2,4'-cyclohex-2-ene]-1',3-dione (2S,5'R)-7-chloro-6-(5-ethyl-1,3,4-oxadiazol-2-yl)-3',4-dimethoxy-5'-methyl-spiro [benzofuran-2,4'-cyclohex-2-ene]-1',3-dione (2S,5'R)-7-chloro-1',4-dimethoxy-5'-methyl-3,3'-dioxo-N'-propanoyl-spiro [benzofuran-2,6'-cyclohexene]-6-carbohydrazide (0.75 g) of example 17 (17a) was dissolved in tetrahydrofuran (10 mL), a (methoxycarbonyl sulfamoyl) triethylammonium hydroxide inner salt (0.614 g) was added, and the mixture was stirred at room temperature for three hours.

Water was added to the reaction mixture, and the reaction mixture was extracted with ethyl acetate. The organic layer was washed with saturated saline and dried with anhydrous sodium sulfate. The residue, which was obtained by distilling the solvent under reduced pressure, was purified by silica gel column chromatography [elution solvent: n-hexane/ethyl acetate=1/1 to 0/1 (V/V)] to obtain 201 mg (yield: 28%, two steps) of the title compound as a pale yellow solid.

Example 18

(2S,5'R)-7-chloro-3',4-dimethoxy-5'-methyl-6-(5-tetrahydropyran-4-yl-1,3,4-oxadiazol-2-yl) spiro [benzofuran-2,4'-cyclohex-2-ene]-1',3-dione (18a)

(2S,5'R)-7-chloro-1',4-dimethoxy-5'-methyl-3,3'-dioxo-N'-(tetrahydropyran-4-carbonyl) spiro [benzofuran-2,6'-cyclohexene]-6-carbohydrazide (2S,5'R)-7-chloro-1',4-dimethoxy-5'-methyl-3,3'-dioxo-N'-(tetrahydropyran-4-carbonyl) spiro [benzofuran-2,6'-cyclohexene]-6-carbohydrazide (2,4,6-trichlorophenyl) (2S,5'R)-7-chloro-1',4-dimethoxy-5'-methyl-3,3'-dioxo-spiro [benzofuran-2,6'-cyclohexene]-6-carboxylate (0.50 g) of example 5 (5a) was dissolved in dichloromethane (20 mL), tetrahydropyran-4-carbohydrazide (0.20 g), 3H-1,2,3-triazolo [4,5-b] pyridine-3-ol (0.125 g), 4-dimethylaminopyridine (0.011 g,), and triethylamine (0.38 mL) were added, and the mixture was allowed to stand at room temperature overnight.

The reaction solution was washed with water and saturated saline and dried with anhydrous sodium sulfate. The residue, which was obtained by distilling the solvent under reduced pressure, was purified by silica gel column chromatography [elution solvent: methanol/ethyl acetate=0/10 to 1/9 (V/V)] to obtain 405 mg (yield: 90%) of the title compound as a pale yellow solid.

(18b)

(2S,5'R)-7-chloro-3',4-dimethoxy-5'-methyl-6-(5-tetrahydropyran-4-yl-1,3,4-oxadiazol-2-yl) spiro [benzofuran-2,4'-cyclohex-2-ene]-1',3-dione (2S,5'R)-7-chloro-3',4-dimethoxy-5'-methyl-6-(5-tetrahydropyran-4-yl-1,3,4-oxadiazol-2-yl) spiro [benzofuran-2,4'-cyclohex-2-ene]-1',3-dione (2S,5'R)-7-chloro-1',4-dimethoxy-5'-methyl-3,3'-dioxo-N'-(tetrahydropyran-4-carbonyl) spiro [benzofuran-2,6'-cyclohexene]-6-carbohydrazide (0.405 g) of example 18 (18a) was dissolved in tetrahydrofuran (10 mL), a (methoxycarbonyl sulfamoyl) triethylammonium hydroxide inner salt (0.392 g) was added, and the mixture was stirred at 50° C. for five hours.

Water was added to the reaction mixture, and the reaction mixture was extracted with ethyl acetate. The organic layer was washed with saturated saline and dried with anhydrous sodium sulfate. The residue, which was obtained by distilling the solvent under reduced pressure, was purified by silica gel column chromatography [elution solvent: n-hexane/ethyl acetate=1/1 to 0/1 (V/V)] to obtain 51 mg (yield: 13%) of the title compound as a pale yellow solid.

Example 19

(2S,5'R)-7-chloro-3',4-dimethoxy-5'-methyl-6-[5-(1-methyl-4-piperidyl)-1,3,4-oxadiazol-2-yl] spiro [benzofuran-2,4'-cyclohex-2-ene]-1',3-dione (19a)

(2S,5'R)-7-chloro-1',4-dimethoxy-5'-methyl-3,3'-dioxo-spiro [benzofuran-2,6'-cyclohexene]-6-carbohydrazide (2S,5'R)-7-chloro-1',4-dimethoxy-5'-methyl-3,3'-dioxo-spiro [benzofuran-2,6'-cyclohexene]-6-carbohydrazide (2,4,6-trichlorophenyl) (2S,5'R)-7-chloro-1',4-dimethoxy-5'-methyl-3,3'-dioxo-spiro [benzofuran-2,6'-cyclohexene]-6-carboxylate (20.0 g) of example 5 (5a) was dissolved in dichloromethane (300 mL), and 3H-1,2,3-triazolo [4,5-b] pyridine-3-ol (5.98 g), N,N-diisopropylethylamine (31.9 mL), and 4-dimethylaminopyridine (0.447 g) were added. After the mixture was stirred at room temperature for four hours, hydrazine monohydrate (1.78 mL) was added, and the mixture was stirred at room temperature for one hour.

After the reaction solution was concentrated, the residue obtained by azeotroping twice with ethanol was triturated with ethanol to obtain 13.2 g (yield: 95%) of the title compound as a pale yellow solid.

(19b)

(2S,5'R)-7-chloro-3',4-dimethoxy-5'-methyl-6-[5-(1-methyl-4-piperidyl)-1,3,4-oxadiazol-2-yl] spiro [benzofuran-2,4'-cyclohex-2-ene]-1',3-dione (2S,5'R)-7-chloro-3',4-dimethoxy-5'-methyl-6-[5-(1-methyl-4-piperidyl)-1,3,4-oxadiazol-2-yl] spiro [benzofuran-2,4'-cyclohex-2-ene]-1',3-dione (2S,5'R)-7-chloro-1',4-dimethoxy-5'-methyl-3,3'-dioxo-spiro [benzofuran-2,6'-cyclohexene]-6-carbohydrazide (0.50 g) of example 19 (19a) was dissolved in tetrahydrofuran (10 mL) and ethanol (10 mL), 1-methylpiperidine-4-carboxylic acid (0.225 g), 4-(4,6-dimethoxy-1,3,5-triazin-2-yl)-4-methylmorpholine hydrochloride (0.436 g), and 4-methylmorpholine (0.361 mL) were added, and the mixture was allowed to stand at room temperature for two days.

Thereafter, 4-(4,6-dimethoxy-1,3,5-triazin-2-yl)-4-methylmorpholine hydrochloride (0.436 g) was added, and the mixture was allowed to stand at room temperature overnight.

The reaction mixture was poured into water, and the reaction mixture was extracted with dichloromethane. The organic layer was washed with saturated saline and dried with anhydrous sodium sulfate. The solvent was distilled under reduced pressure.

The obtained residue was dissolved in dichloromethane (10 mL), triethylamine (1.45 mL) and p-toluene sulfonyl chloride (0.475 g) were added, and the mixture was stirred at room temperature for three hours.

The reaction mixture was poured into water, the mixture was made weakly basic with saturated sodium bicarbonate aqueous solution, and the reaction mixture was extracted with dichloromethane. The organic layer was washed with saturated saline and dried with anhydrous sodium sulfate. The residue, which was obtained by distilling the solvent under reduced pressure, was purified by NH silica gel column chromatography [elution solvent: n-hexane/ethyl acetate=1/1 to 0/1 (V/V)], and the obtained solid was triturated with n-hexane and ethyl acetate to obtain 298 mg (yield: 29%, two steps) of the title compound as a white solid.

Example 20

(2S,5'R)-7-chloro-6-[5-(4-fluoro-1-methyl-4-piperidyl)-1,3,4-oxadiazol-2-yl]-3',4-dimethoxy-5'-methyl-spiro [benzofuran-2,4'-cyclohex-2-ene]-1',3-dione (2S,5'R)-7-chloro-6-[5-(4-fluoro-1-methyl-4-piperidyl)-1,3,4-oxadiazol-2-yl]-3',4-dimethoxy-5'-methyl-spiro [benzofuran-2,4'-cyclohex-2-ene]-1',3-dione (2S,5'R)-7-chloro-1',4-dimethoxy-5'-methyl-3,3'-dioxo-spiro [benzofuran-2,6'-cyclohexene]-6-carbohydrazide (0.50 g) of example 19 (19a) was dissolved in tetrahydrofuran (10 mL), 4-fluoro-1-methylpiperidine-4-carboxylic acid hydrochloride (0.254 g), 4-(4,6-dimethoxy-1,3,5-triazin-2-yl)-4-methylmorpholine hydrochloride (0.436 g), and 4-methylmorpholine (0.361 mL) were added, and the mixture was allowed to stand at room temperature overnight.

The reaction mixture was poured into water, and the reaction mixture was extracted with dichloromethane. The organic layer was washed with saturated saline and dried with anhydrous sodium sulfate. The solvent was distilled under reduced pressure.

The obtained residue was dissolved in dichloromethane (10 mL), triethylamine (1.33 mL) and p-toluene sulfonyl chloride (0.437 g) were added, and the mixture was stirred at room temperature for two hours.

The reaction mixture was poured into water, and the reaction mixture was extracted with dichloromethane. The organic layer was washed with saturated saline and dried with anhydrous sodium sulfate. The residue, which was obtained by distilling the solvent under reduced pressure, was purified by silica gel column chromatography [elution solvent: ethyl acetate/methanol=10/0 to 85/15 (V/V)], and the obtained solid was triturated with n-hexane and ethyl acetate to obtain 235 mg (yield: 24%, two steps) of the title compound as a white solid.

Example 21

(2S,5'R)-7-chloro-3',4-dimethoxy-6-[5-[(1S)-1-methoxyethyl]-1,3,4-oxadiazol-2-yl]-5'-methyl-spiro [benzofuran-2,4'-cyclohex-2-ene]-1',3-dione (21a)

(2S,5'R)-7-chloro-1',4-dimethoxy-N'-[(2S)-2-methoxypropanoyl]-5'-methyl-3,3'-dioxo-spiro [benzofuran-2,6'-cyclohexene]-6-carbohydrazide (2S,5'R)-7-chloro-1',4-dimethoxy-N'-[(2S)-2-methoxypropanoyl]-5'-methyl-3,3'-dioxo-spiro [benzofuran-2,6'-cyclohexene]-6-carbohydrazide (2S,5'R)-7-chloro-1',4-dimethoxy-5'-methyl-3,3'-dioxo-spiro [benzofuran-2,6'-cyclohexene]-6-carbohydrazide (0.50 g) of example 19 (19a) was dissolved in tetrahydrofuran (10 mL), (S)-(–)-2-methoxy propionic acid (0.164 g) and 4-(4,6-dimethoxy-1,3,5-triazin-2-yl)-4-methylmorpholine hydrochloride (0.545 g) were added, and the mixture was allowed to stand at room temperature overnight.

The reaction mixture was poured into water, and the reaction mixture was extracted with ethyl acetate. The organic layer was washed with water and saturated saline and dried with anhydrous sodium sulfate. The residue, which was obtained by distilling the solvent under reduced pressure, was purified by silica gel column chromatography [elution solvent: ethyl acetate/methanol=I/O to 19/1 (V/V)] to obtain 410 mg (yield: 67%) of the title compound as a white solid.

(21b)

(2S,5'R)-7-chloro-3',4-dimethoxy-6-[5-[(1S)-1-methoxyethyl]-1,3,4-oxadiazol-2-yl]-5'-methyl-spiro [benzofuran-2,4'-cyclohex-2-ene]-1',3-dione (2S,5'R)-7-chloro-3',4-dimethoxy-6-[5-[(1S)-1-methoxyethyl]-1,3,4-oxadiazol-2-yl]-5'-methyl-spiro [benzofuran-2,4'-cyclohex-2-ene]-1',3-dione (2S,5'R)-7-chloro-1',4-dimethoxy-N'-[(2S)-2-methoxypropanoyl]-5'-methyl-3,3'-dioxo-spiro [benzofuran-2,6'-cyclohexene]-6-carbohydrazide (0.410 g) of example 21 (21a) was dissolved in dichloromethane (5 mL), triethylamine (0.613 mL) and p-toluene sulfonyl chloride (0.200 g) were added, and the mixture was stirred at room temperature for two hours.

The reaction mixture was poured into water, and after neutralization with 1 mol/L hydrochloric acid, the reaction mixture was extracted with ethyl acetate. The organic layer was washed with water and saturated saline and dried with anhydrous sodium sulfate. The residue, which was obtained by distilling the solvent under reduced pressure, was purified by silica gel column chromatography [elution solvent: n-hexane/ethyl acetate=1/1 to 0/1 (V/V)], and the obtained solid was triturated with n-hexane and ethyl acetate to obtain 235 mg (yield: 60%) of the title compound as a white solid.

Example 22

(2S,5'R)-7-chloro-4-ethoxy-3'-methoxy-5'-methyl-6-(5-methyl-1,3,4-oxadiazol-2-yl) spiro [benzofuran-2,4'-cyclohex-2-ene]-1',3-dione (22a)

(2S,5'R)-7-chloro-4-hydroxy-3'-methoxy-5'-methyl-6-(5-methyl-1,3,4-oxadiazol-2-yl) spiro [benzofuran-2,4'-cyclohex-2-ene]-1',3-dione (2S,5'R)-7-chloro-4-hydroxy-3'-methoxy-5'-methyl-6-(5-methyl-1,3,4-oxadiazol-2-yl) spiro [benzofuran-2,4'-cyclohex-2-ene]-1',3-dione Magnesium in a scraped form (0.36 g) was added to diethyl ether (50 mL), and iodine (3.5 g) was added in three portions every 15 min. After stirring at room temperature for 30 min, (2S,5'R)-7-chloro-3',4-dimethoxy-5'-methyl-6-(5-methyl-1,3,4-oxadiazol-2-yl) spiro [benzofuran-2,4'-cyclohex-2-ene]-1',3-dione (5.0 g) of example 5 (5c) and toluene (100 mL) were added, and the mixture was stirred at 100° C. for six hours.

Water was added to the reaction mixture, and after neutralization with 1 mol/L hydrochloric acid, it was extracted with ethyl acetate. The organic layer was washed with saturated saline and dried with anhydrous sodium sulfate, and the solvent was distilled under reduced pressure to obtain 2.5 g (yield: 52%) of the title compound as a pale yellow solid.

(22b)

(2S,5'R)-7-chloro-4-ethoxy-3'-methoxy-5'-methyl-6-(5-methyl-1,3,4-oxadiazol-2-yl) spiro [benzofuran-2,4'-cyclohex-2-ene]-1',3-dione (2S,5'R)-7-chloro-4-ethoxy-3'-methoxy-5'-methyl-6-(5-methyl-1,3,4-oxadiazol-2-yl) spiro [benzofuran-2,4'-cyclohex-2-ene]-1',3-dione (2S,5'R)-7-chloro-4-hydroxy-3'-methoxy-5'-methyl-6-(5-methyl-1,3,4-oxadiazol-2-yl) spiro [benzofuran-2,4'-cyclohex-2-ene]-1',3-dione (200 mg) of example 22 (22a) was dissolved in N,N-dimethylformamide (3.0 mL), potassium carbonate (283 mg) and iodoethane (0.082 mL) were added, and the mixture was stirred at 90° C. for five hours.

The reaction mixture was poured into water, and the reaction mixture was extracted with ethyl acetate. The organic layer was washed with water and saturated saline and dried with anhydrous sodium sulfate. The residue, which was obtained by distilling the solvent under reduced pressure, was purified by silica gel column chromatography [elution solvent: n-hexane/ethyl acetate=7/3 to 0/10 (V/V)] to obtain 146 mg (yield: 68%) of the title compound as a white solid.

Example 23

(2S,5'R)-7-chloro-4-(difluoromethoxy)-3'-methoxy-5'-methyl-6-(5-methyl-1,3,4-oxadiazol-2-yl) spiro [benzofuran-2,4'-cyclohex-2-ene]-1',3-dione (23a)

(2S,5'R)-7-chloro-4-(difluoromethoxy)-3',6-dimethoxy-5'-methyl-spiro [benzofuran-2,4'-cyclohex-2-ene]-1',3-dione (2S,5'R)-7-chloro-4-(difluoromethoxy)-3',6-dimethoxy-5'-methyl-spiro [benzofuran-2,4'-cyclohex-2-ene]-1',3-dione (2S,5'R)-7-chloro-6-hydroxy-3',4-dimethoxy-5'-methyl-spiro [benzofuran-2,4'-cyclohex-2-ene]-1',3-dione (3.5 g) of example 1 (1a) was dissolved in acetonitrile (70 mL), water (30 mL) and potassium hydroxide (12 g) were added at −20° C., and the mixture was stirred at −20° C. for 10 min. Diethyl (bromodifluoromethyl) phosphonate (5.5 mL) was slowly added at −20° C., and the temperature was slowly raised to 0° C. over one hour.

Water was added to the reaction mixture, and the reaction mixture was extracted with ethyl acetate. The organic layer was washed with water and saturated saline and dried with anhydrous sodium sulfate. The residue, which was obtained by distilling the solvent under reduced pressure, was purified by silica gel column chromatography [elution solvent: n-hexane/ethyl acetate=8/2 to 2/8 (V/V)] to obtain 2.5 g (yield: 62%) of the title compound as a white solid.

(23b)

(2S,5'R)-7-chloro-4-(difluoromethoxy)-6-hydroxy-3'-methoxy-5'-methyl-spiro [benzofuran-2,4'-cyclohex-2-ene]-1',3-dione (2S,5'R)-7-chloro-4-(difluoromethoxy)-6-hydroxy-3'-methoxy-5'-methyl-spiro [benzofuran-2,4'-cyclohex-2-ene]-1',3-dione (2S,5'R)-7-chloro-4-(difluoromethoxy)-3',6-dimethoxy-5'-methyl-spiro [benzofuran-2,4'-cyclohex-2-ene]-1',3-dione (2.5 g) of example 23 (23a) was dissolved in pyridine (500 mL), 18-crown-6 (1.9 g) and potassium iodide (1.1 g) were added, and the mixture was stirred at 120° C. for eight hours. The reaction solution was concentrated, water was added to the reaction mixture, and after neutralization with 1 mol/L hydrochloric acid, the reaction mixture was extracted with ethyl acetate.

The organic layer was washed with saturated saline and dried with anhydrous sodium sulfate. The residue, which was obtained by distilling the solvent under reduced pressure, was purified by silica gel column chromatography [elution solvent: n-hexane/ethyl acetate=1/1 to 0/1 (V/V)] to obtain 1.7 g (yield: 71%) of the title compound as a pale-yellow solid.

(23c)

[(2S,5'R)-7-chloro-4-(difluoromethoxy)-1'-methoxy-5'-methyl-3,3'-dioxo-spiro [benzofuran-2,6'-cyclohexene]-6-yl] trifluoromethanesulfonate

[(2S,5'R)-7-chloro-4-(difluoromethoxy)-1'-methoxy-5'-methyl-3,3'-dioxo-spiro [benzofuran-2,6'-cyclohexene]-6-yl] trifluoromethanesulfonate (2S,5'R)-7-chloro-4-(difluoromethoxy)-6-hydroxy-3'-methoxy-5'-methyl-spiro [benzofuran-2,4'-cyclohex-2-ene]-1',3-dione (1.7 g) of example 23 (23b) was dissolved in dichloromethane (200 mL), N-phenylbis (trifluoromethanesulfonimide) (1.9 g) and triethylamine (1.6 mL) were added, and the mixture was allowed to stand at room temperature overnight.

The reaction solution was diluted with dichloromethane, and the organic layer was washed with water and saturated saline and dried with anhydrous sodium sulfate. The residue, which was obtained by distilling the solvent under reduced pressure, was purified by silica gel column chromatography [elution solvent: n-hexane/ethyl acetate=10/0 to 6/4 (V/V)] to obtain 950 mg (yield: 41%) of the title compound as a white solid.

(23d)

(2,4,6-trichlorophenyl) (2S,5'R)-7-chloro-4-(difluoromethoxy)-1'-methoxy-5'-methyl-3,3'-dioxo-spiro [benzofuran-2,6'-cyclohexene]-6-carboxylate 2,4,6-trichlorophenyl (2S,5'R)-7-chloro-4-(difluoromethoxy)-1'-methoxy-5'-methyl-3,3'-dioxo-spiro [benzofuran-2,6'-cyclohexene]-6-carboxylate

[(2S,5'R)-7-chloro-4-(difluoromethoxy)-1'-methoxy-5'-methyl-3,3'-dioxo-spiro [benzofuran-2,6'-cyclohexene]-6-yl] trifluoromethanesulfonate (0.40 g) of example 23 (23c) was dissolved in toluene (5 mL); palladium (II) acetate (0.018 g), 4,5-bis (diphenyl phosphino)-9,9-dimethylxanthene (0.091 g), and N,N-diisopropylethylamine (0.275 mL) were added; and the mixture was heated to 80° C. 2,4,6-trichlorophenyl formate (0.231 g) was added in three portions every 30 min.

After stirring at 80° C. for 30 min, the reaction mixture was poured into water, and the reaction mixture was extracted with ethyl acetate. The organic layer was washed with water and saturated saline and dried with anhydrous sodium sulfate. The residue, which was obtained by distilling the solvent under reduced pressure, was purified by silica gel column chromatography [elution solvent: n-hexane/ethyl acetate=10/0 to 6/4 (V/V)] to obtain 182 mg (yield: 40%) of the title compound as a white solid.

(23e)

(2S,5'R)—N'-acetyl-7-chloro-4-(difluoromethoxy)-1'-methoxy-5'-methyl-3,3'-dioxo-spiro [benzofuran-2,6'-cyclohexene]-6-carbohydrazide (2S,5'R)—N'-acetyl-7-chloro-4-(difluoromethoxy)-1'-methoxy-5'-methyl-3,3'-dioxo-spiro [benzofuran-2,6'-cyclohexene]-6-carbohydrazide (2,4,6-trichlorophenyl) (2S,5'R)-7-chloro-4-(difluoromethoxy)-1'-methoxy-5'-methyl-3,3'-dioxo-spiro [benzofuran-2,6'-cyclohexene]-6-carboxylate (0.182 g) of example 23 (23d) was dissolved in dichloromethane (20 mL); acetohydrazide (purity: 90%, 0.035 g), 3H-1,2,3-triazolo [4,5-b] pyridine-3-ol (0.043 g), 4-dimethylaminopyridine (0.0038 g), and triethylamine (0.131 mL) were added; and the mixture was allowed to stand at room temperature overnight.

The reaction mixture was added to water, and the reaction mixture was extracted with ethyl acetate. The organic layer was washed with water and saturated saline and dried with anhydrous sodium sulfate. The residue, which was obtained by distilling the solvent under reduced pressure, was purified by silica gel column chromatography [elution solvent: n-hexane/ethyl acetate=10/0 to 7/3 (V/V)] to obtain 141 mg (yield: 98%) of the title compound as a white solid.

(23f)

(2S,5'R)-7-chloro-4-(difluoromethoxy)-3'-methoxy-5'-methyl-6-(5-methyl-1,3,4-oxadiazol-2-yl) spiro [benzofuran-2,4'-cyclohex-2-ene]-1',3-dione (2S,5'R)-7-chloro-4-(difluoromethoxy)-3'-methoxy-5'-methyl-6-(5-methyl-1,3,4-oxadiazol-2-yl) spiro [benzofuran-2,4'-cyclohex-2-ene]-1',3-dione (2S,5'R)—N'-acetyl-7-chloro-4-(difluoromethoxy)-1'-methoxy-5'-methyl-3,3'-dioxo-spiro [benzofuran-2,6'-cyclohexene]-6-carbohydrazide (0.141 g) of example 23 (23e) was dissolved in 1,4-dioxane (5.0 mL), a (methoxycarbonyl sulfamoyl) triethylammonium hydroxide inner salt (0.146 g) was added, and the mixture was stirred at room temperature for two hours.

The reaction mixture was poured into water, and the reaction mixture was extracted with ethyl acetate. The organic layer was washed with water and saturated saline and dried with anhydrous sodium sulfate. The residue, which was obtained by distilling the solvent under reduced pressure, was purified by silica gel column chromatography [elution solvent: n-hexane/ethyl acetate=10/0 to 4/6 (V/V)] to obtain 70 mg (yield: 52%) of the title compound as a white solid.

Example 24

(2S,5'R)-7-chloro-3',4-dimethoxy-6-[3-(1-methoxy-ethyl)-1,2,4-oxadiazol-5-yl]-5'-methyl-spiro [benzofuran-2,4'-cyclohex-2-ene]-1',3-dione (24a)

[(Z)-(1-amino-2-methoxy-propylidene) amino] (2S,5'R)-7-chloro-1',4-dimethoxy-5'-methyl-3,3'-dioxo-spiro [benzofuran-2,6'-cyclohexene]-6-carboxylate (Z)-(1-amino-2-methoxy-propylidene) amino (2S,5'R)-7-chloro-1',4-dimethoxy-5'-methyl-3,3'-dioxo-spiro [benzofuran-2,6'-cyclohexene]-6-carboxylate (2,4,6-trichlorophenyl) (2S,5'R)-7-chloro-1',4-dimethoxy-5'-methyl-3,3'-dioxo-spiro [benzofuran-2,6'-cyclohexene]-6-carboxylate (0.5 g) of example 5 (5a) was dissolved in dichloromethane (10 mL); N'-hydroxy-2-methoxypropanimidamide (0.130 g), 3H-1,2,3-triazolo [4,5-b] pyridine-3-ol (0.125 g), 4-dimethylaminopyridine (0.011 g), and N,N-diisopropylethylamine (0.478 mL) were added; and the mixture was stirred at room temperature for three hours.

The reaction mixture was poured into water, and after neutralization with 1 mol/L hydrochloric acid, the reaction mixture was extracted with ethyl acetate. The organic layer was washed with water and saturated saline and dried with anhydrous sodium sulfate. The residue, which was obtained by distilling the solvent under reduced pressure, was purified by silica gel column chromatography [elution solvent: n-hexane/ethyl acetate=1/1 to 0/1 (V/V)] to obtain 375 mg (yield: 88%) of the title compound as a white solid.

(24b)

(2S,5'R)-7-chloro-3',4-dimethoxy-6-[3-(1-methoxy-ethyl)-1,2,4-oxadiazol-5-yl]-5'-methyl-spiro [benzofuran-2,4'-cyclohex-2-ene]-1',3-dione (2S,5'R)-7-chloro-3',4-dimethoxy-6-[3-(1-methoxy-ethyl)-1,2,4-oxadiazol-5-yl]-5'-methyl-spiro [benzofuran-2,4'-cyclohex-2-ene]-1',3-dione

[(Z)-(1-amino-2-methoxy-propylidene) amino] (2S,5'R)-7-chloro-1',4-dimethoxy-5'-methyl-3,3'-dioxo-spiro [benzofuran-2,6'-cyclohexene]-6-carboxylate (0.375 g) of example 24 (24a) was dissolved in toluene (10 mL), and the mixture was stirred at 120° C. for 12 hours.

The residue, which was obtained by distilling the solvent under reduced pressure, was purified by silica gel column chromatography [elution solvent: n-hexane/ethyl acetate=10/0 to 7/3 (V/V)], and trituration was carried out with n-hexane and ethyl acetate to obtain 265 mg (yield: 74%) of the title compound as a white solid.

Example 25

(2S,5'R)-7-chloro-6-[3-(1-hydroxy-1-methyl-ethyl)-1,2,4-oxadiazol-5-yl]-3',4-dimethoxy-5'-methyl-spiro[benzofuran-2,4'-cyclohex-2-ene]-1',3-dione (25a)

[(Z)-(1-amino-2-hydroxy-2-methyl-propylidene)amino] (2S,5'R)-7-chloro-1',4-dimethoxy-5'-methyl-3,3'-dioxo-spiro [benzofuran-2,6'-cyclohexene]-6-carboxylate (Z)-(1-amino-2-hydroxy-2-methyl-propylidene)amino (2S,5'R)-7-chloro-1',4-dimethoxy-5'-methyl-3,3'-dioxo-spiro [benzofuran-2,6'-cyclohexene]-6-carboxylate (2,4,6-trichlorophenyl) (2S,5'R)-7-chloro-1',4-dimethoxy-5'-methyl-3,3'-dioxo-spiro [benzofuran-2,6'-cyclohexene]-6-carboxylate (1.0 g) of example 5 (5a) was dissolved in dichloromethane (20 mL); 2,N-dihydroxy-2-methyl-propionamizine (0.238 g), 3H-1,2,3-triazolo [4,5-b]pyridine-3-ol (0.249 g), 4-dimethylaminopyridine (0.022 g), and N,N-diisopropylethylamine (0.957 mL) were added; and the mixture was allowed to stand at room temperature overnight.

The reaction mixture was poured into water and the reaction mixture was extracted with ethyl acetate. The organic layer was washed with water and saturated saline and dried with anhydrous sodium sulfate. The residue, which was obtained by distilling the solvent under reduced pressure, was purified by silica gel column chromatography [elution solvent: ethyl acetate/methanol=10/0 to 9/1 (V/V)] to obtain 765 mg (yield: 89%) of the title compound as a white solid.

(25b)

(2S,5'R)-7-chloro-6-[3-(1-hydroxy-1-methyl-ethyl)-1,2,4-oxadiazol-5-yl]-3',4-dimethoxy-5'-methyl-spiro[benzofuran-2,4'-cyclohex-2-ene]-1',3-dione (2S,5'R)-7-chloro-6-[3-(1-hydroxy-1-methyl-ethyl)-1,2,4-oxadiazol-5-yl]-3',4-dimethoxy-5'-methyl-spiro[benzofuran-2,4'-cyclohex-2-ene]-1',3-dione

[(Z)-(1-amino-2-hydroxy-2-methyl-propylidene) amino] (2S,5'R)-7-chloro-1',4-dimethoxy-5'-methyl-3,3'-dioxo-spiro [benzofuran-2,6'-cyclohexene]-6-carboxylate (0.765 g) of example 25 (25a) was dissolved in toluene (10 mL), and the mixture was stirred at 110° C. for seven hours.

The residue, which was obtained by distilling the solvent under reduced pressure, was purified by silica gel column chromatography [elution solvent: n-hexane/ethyl acetate=1/1 to 0/1 (V/V)], and trituration was carried out with n-hexane and ethyl acetate to obtain 512 mg (yield: 70%) of the title compound as a white solid.

Example 26

(2S,5'R)-7-chloro-3',4-dimethoxy-5'-methyl-6-(1H-pyrazol-5-yl) spiro [benzofuran-2,4'-cyclohex-2-ene]-1',3-dione (26a)

(2S,5'R)-7-chloro-3',4-dimethoxy-5'-methyl-6-(2-tetrahydropyran-2-ylpyrazol-3-yl) spiro [benzofuran-2,4'-cyclohex-2-ene]-1',3-dione (2S,5'R)-7-chloro-3',4-dimethoxy-5'-methyl-6-(2-tetrahydropyran-2-ylpyrazol-3-yl) spiro [benzofuran-2,4'-cyclohex-2-ene]-1',3-dione

[(2S,5'R)-7-chloro-1',4-dimethoxy-5'-methyl-3,3'-dioxo-spiro [benzofuran-2,6'-cyclohexene]-6-yl]trifluoromethanesulfonate (2.0 g) of example 3 (3a) was dissolved in 1,4-dioxane (30 mL) and water (2 mL); 1-tetrahydropyran-2-yl-5-(4,4,5,5-tetramethyl-1,3,2-dioxaborolan-2-yl) pyrazole (1.54 g), potassium carbonate (1.76 g), and [1,1'-bis (diphenyl phosphino) ferrocene] palladium (II) dichloride (0.155 g) were added at room temperature; and the mixture was stirred at 90° C. for three hours.

After the reaction temperature was returned to room temperature, the insoluble substances were filtered. The filtrate was poured into water and extracted with dichloromethane. The organic layer was washed with saturated saline and dried with anhydrous sodium sulfate. The residue, which was obtained by distilling the solvent under reduced pressure, was purified by silica gel column chromatography [elution solvent: petroleum ether/ethyl acetate=10/1 to 2/1 (V/V)] to obtain 1.8 g (yield: 90%) of the title compound as a pale yellow solid.

(26b)

(2S,5'R)-7-chloro-3',4-dimethoxy-5'-methyl-6-(1H-pyrazol-5-yl) spiro [benzofuran-2,4'-cyclohex-2-ene]-1',3-dione (2S,5'R)-7-chloro-3',4-dimethoxy-5'-methyl-6-(1H-pyrazol-5-yl) spiro [benzofuran-2,4'-cyclohex-2-ene]-1',3-dione (2S,5'R)-7-chloro-3',4-dimethoxy-5'-methyl-6-(2-tetrahydropyran-2-ylpyrazol-3-yl) spiro [benzofuran-2,4'-cyclohex-2-ene]-1',3-dione (1.8 g) of example 26 (26a) was dissolved in dichloromethane (5 mL), trifluoroacetic acid (5 mL) was added, and the mixture was stirred at room temperature for 20 minutes.

The reaction mixture was poured into water, and the reaction mixture was extracted with dichloromethane. The organic layer was washed with saturated saline and dried with anhydrous sodium sulfate. The residue, which was obtained by distilling the solvent under reduced pressure, was purified by high performance liquid chromatography [elution solvent: 0.05% hydrochloric acid/acetonitrile=70/30 to 45/55 (V/V)] to obtain 1.1 g (yield: 74%) of the title compound as a yellow solid.

Example 27

(2S,5'R)-7-chloro-3',4-dimethoxy-6-[1-(2-methoxyethyl) pyrazol-3-yl]-5'-methyl-spiro [benzofuran-2,4'-cyclohex-2-ene]-1',3-dione (2S,5'R)-7-chloro-3',4-dimethoxy-6-[1-(2-methoxyethyl) pyrazol-3-yl]-5'-methyl-spiro [benzofuran-2,4'-cyclohex-2-ene]-1',3-dione (2S,5'R)-7-chloro-3',4-dimethoxy-5'-methyl-6-(1H-pyrazol-5-yl) spiro [benzofuran-2,4'-cyclohex-2-ene]-1',3-dione (250 mg) of example 26 (26b) was dissolved in N,N-dimethylformamide (5 mL), 2-bromoethyl methyl ether (179 mg) and potassium carbonate (267 mg) were added, and the mixture was stirred at 80° C. for three hours.

The reaction mixture was poured into water, and the reaction mixture was extracted with dichloromethane. The organic layer was washed with saturated saline and dried with anhydrous sodium sulfate. The residue, which was obtained by distilling the solvent under reduced pressure, was purified by high performance liquid chromatography [elution solvent: 10 mM ammonium hydrogen carbonate aqueous solution/acetonitrile=67/33 to 37/63 (V/V)] to obtain 81 mg (yield: 28%) of the title compound as a white solid.

Example 28

(2S,5'R)-7-chloro-6-(1,8-dioxa-2-azaspiro [4.5] dec-2-en-3-yl)-3',4-dimethoxy-5'-methyl-spiro [benzofuran-2,4'-cyclohex-2-ene]-1',3-dione (28a)

(2S,5'R)-7-chloro-1',4-dimethoxy-5'-methyl-3,3'-dioxo-spiro [benzofuran-2,6'-cyclohexene]-6-carbaldehyde (2S,5'R)-7-chloro-1',4-dimethoxy-5'-methyl-3,3'-dioxo-spiro [benzofuran-2,6'-cyclohexene]-6-carbaldehyde

[(2S,5'R)-7-chloro-1',4-dimethoxy-5'-methyl-3,3'-dioxo-spiro [benzofuran-2,6'-cyclohexene]-6-yl]trifluoromethanesulfonate (4.5 g) of example 3 (3a) was dissolved in 1,4-dioxane (120 mL), tributylstannyl methanol (CAS Registry Number: 27490-33-1) (8.29 g) and tetrakis triphenyl phosphine palladium (1.66 g) were added at room temperature, and the mixture was stirred at 60° C. for 15 hours.

The residue, which was obtained by distilling the solvent under reduced pressure, was roughly purified by silica gel column chromatography [elution solvent: petroleum ether/ethyl acetate=25/i to 1/1 (V/V)].

The obtained crude product was dissolved in dichloromethane (20 mL), Dess-Martin Periodinane (3.61 g) was added, and the mixture was stirred at room temperature for two hours.

The reaction mixture was poured into water, and the reaction mixture was extracted with dichloromethane. The organic layer was washed with saturated saline and dried with anhydrous sodium sulfate. The residue, which was obtained by distilling the solvent under reduced pressure, was purified by silica gel column chromatography [elution solvent: petroleum ether/ethyl acetate=1/1 (V/V)] to obtain 1.25 g (yield: 37%, two steps) of the title compound as a yellow solid.

(28b)

(2S,5'R)-7-chloro-6-(1,8-dioxa-2-azaspiro [4.5] dec-2-en-3-yl)-3',4-dimethoxy-5'-methyl-spiro [benzofuran-2,4'-cyclohex-2-ene]-1',3-dione (2S,5'R)-7-chloro-6-(1,8-dioxa-2-azaspiro [4.5] dec-2-en-3-yl)-3',4-dimethoxy-5'-methyl-spiro [benzofuran-2,4'-cyclohex-2-ene]-1',3-dione (2S,5'R)-7-chloro-1',4-dimethoxy-5'-methyl-3,3'-dioxo-spiro [benzofuran-2,6'-cyclohexene]-6-carbaldehyde (1.0 g) of example 28 (28a) was dissolved in methanol (10 mL), hydroxylamine hydrochloride (158 mg) and sodium acetate (585 mg) were added, and the mixture was stirred at room temperature for one hour.

The reaction mixture was poured into water, and the reaction mixture was extracted with ethyl acetate. The organic layer was washed with saturated saline and dried with anhydrous sodium sulfate. The residue, which was obtained by distilling the solvent under reduced pressure, was roughly purified by silica gel column chromatography [elution solvent: petroleum ether/ethyl acetate=50/1 to 10/1 (V/V)], and a crude product (730 mg) containing (2S,5'R,6E)-7-chloro-1',4-dimethoxy-5'-methyl-3,3'-dioxo-spiro [benzofuran-2,6'-cyclohexene]-6-carbaldehyde oxime as a main component was obtained as a yellow solid.

The obtained crude product (300 mg) was dissolved in dichloromethane (6 mL); 4-methylenete trahydropyran (CAS Registry Number: 36838-71-8) (322 mg), pyridine (0.041 mL), and sodium hypochlorite (20 mL) were added at −10° C., and the mixture was stirred at room temperature for three hours.

The reaction mixture was poured into water and the reaction mixture was extracted with dichloromethane. The organic layer was washed with saturated saline and dried with anhydrous sodium sulfate. The residue, which was obtained by distilling the solvent under reduced pressure, was purified by high performance liquid chromatography [elution solvent: 0.225% formic acid aqueous solution/acetonitrile=55/45 to 45/55 (V/V)] to obtain 92 mg (yield: 17%, two steps) of the title compound as a white solid.

Example 29

(2S,5'R)-7-chloro-3',4-dimethoxy-5'-methyl-6-(8-methyl-1-oxa-2,8-diazaspiro [4.5] dec-2-en-3-yl) spiro [benzofuran-2,4'-cyclohex-2-ene]-1',3-dione (2S,5'R)-7-chloro-3',4-dimethoxy-5'-methyl-6-(8-methyl-1-oxa-2,8-diazaspiro [4.5] dec-2-en-3-yl) spiro [benzofuran-2,4'-cyclohex-2-ene]-1',3-dione The crude product (92 mg) containing (2S,5'R,6E)-7-chloro-1',4-dimethoxy-5'-methyl-3,3'-dioxo-spiro [benzofuran-2,6'-cyclohexene]-6-carbaldehyde oxime, which was obtained as an intermediate in example 28 (28b), as the main component was dissolved in dichloromethane (3.0 mL); tert-butyl 4-methylene piperidine-1-carboxylate (CAS Registry Number: 159635-49-1) (162 mg), pyridine (0.013 mL), and sodium hypochlorite (7.0 mL) were added at −10° C.; and the mixture was stirred at −10° C. for three hours.

The reaction mixture was poured into water, and the reaction mixture was extracted with dichloromethane. The organic layer was washed with saturated saline and dried with anhydrous sodium sulfate. The residue, which was obtained by distilling the solvent under reduced pressure, was roughly purified by silica gel column chromatography [elution solvent: petroleum ether/ethyl acetate=1/1 (V/V)].

The obtained crude product was dissolved in dichloromethane (4.0 mL), and a 1,4-dioxane solution of hydrogen chloride (4 M, 50 mL) was added. After stirring at room temperature for two hours, the solvent was distilled under reduced pressure.

The obtained residue was dissolved in methanol (1.0 mL); formaldehyde (70 mg), triethylamine (0.078 mL), acetic acid (0.065 mL), and sodium cyanoborohydride (55 mg) were added; and the mixture was stirred at room temperature for three hours.

The residue, which was obtained by distilling the solvent under reduced pressure, was purified by high performance liquid chromatography [elution solvent: 0.05% ammonia aqueous solution/acetonitrile=67/33 to 37/63 (V/V)] to obtain 41 mg (yield: 32%, three steps) of the title compound as a white solid.

Example 30

(2S,5'R)-7-chloro-3',4-dimethoxy-6-(2-methoxypyrimidin-5-yl)-5'-methyl-spiro [benzofuran-2,4'-cyclohex-2-ene]-1',3-dione (2S,5'R)-7-chloro-3',4-dimethoxy-6-(2-methoxypyrimidin-5-yl)-5'-methyl-spiro [benzofuran-2,4'-cyclohex-2-ene]-1',3-dione

[(2S,5'R)-7-chloro-1',4-dimethoxy-5'-methyl-3,3'-dioxo-spiro [benzofuran-2,6'-cyclohexene]-6-yl]trifluoromethanesulfonate (0.50 g) of example 3 (3a) was dissolved in toluene (10 mL); 2-methoxy-5-pyrimidylboronic acid (0.245 g), saturated sodium bicarbonate aqueous solution (5.0 mL), and chloro (2-dicyclohexyl phosphino-2',4',6'-triisopropyl-1,1'-biphenyl) [2-(2'-amino-1,1'-biphenyl)] palladium (II) (0.167 g) were added at room temperature; and the mixture was stirred at 90° C. for two hours.

The reaction mixture was poured into water, and the reaction mixture was extracted with ethyl acetate. The organic layer was washed with water and saturated saline and dried with anhydrous sodium sulfate. The residue, which was obtained by distilling the solvent under reduced pressure, was purified by silica gel column chromatography [elution solvent: n-hexane/ethyl acetate=7/3 to 1/9 (V/V)] to obtain 58 mg (yield: 12%) of the title compound as a pale yellow solid.

Example 31

(2S,5'R)-7-chloro-3',4-dimethoxy-6-(6-methoxy-3-pyridyl)-5'-methyl-spiro [benzofuran-2,4'-cyclohex-2-ene]-1',3-dione (2S,5'R)-7-chloro-3',4-dimethoxy-6-(6-methoxy-3-pyridyl)-5'-methyl-spiro [benzofuran-2,4'-cyclohex-2-ene]-1',3-dione

[(2S,5'R)-7-chloro-1',4-dimethoxy-5'-methyl-3,3'-dioxo-spiro [benzofuran-2,6'-cyclohexene]-6-yl]trifluoromethanesulfonate (0.50 g) of example 3 (3a) was dissolved in toluene (10 mL); 2-methoxypyridine-5-boronic acid (0.244 g), saturated sodium bicarbonate aqueous solution (5.0 mL), and chloro (2-dicyclohexyl phosphino-2',4',6'-triisopropyl-1,1'-biphenyl) [2-(2'-amino-1,1'-biphenyl)] palladium (II) (0.167 g) were added at room temperature; and the mixture was stirred at 90° C. for two hours.

The reaction mixture was poured into water, and the reaction mixture was extracted with ethyl acetate. The organic layer was washed with water and saturated saline and dried with anhydrous sodium sulfate. The residue, which was obtained by distilling the solvent under reduced pressure, was purified by silica gel column chromatography [elution solvent: n-hexane/ethyl acetate=1/1 to 0/1 (V/V)] to obtain 128 mg (yield: 28%) of the title compound as a pale yellow solid.

Example 32

(2S,5'R)-7-chloro-3',4-dimethoxy-5'-methyl-6-(3-pyridyl) spiro [benzofuran-2,4'-cyclohex-2-ene]-1',3-dione (2S,5'R)-7-chloro-3',4-dimethoxy-5'-methyl-6-(3-pyridyl) spiro [benzofuran-2,4'-cyclohex-2-ene]-1',3-dione

[(2S,5'R)-7-chloro-1',4-dimethoxy-5'-methyl-3,3'-dioxo-spiro [benzofuran-2,6'-cyclohexene]-6-yl]trifluoromethanesulfonate (0.50 g) of example 3 (3a) was dissolved in N,N-dimethylformamide (5.0 mL); 3-pyridyl boronic acid (0.196 g), [1,1'-bis (diphenyl phosphino) ferrocene] palladium (II) dichloride (0.347 g), and sodium bicarbonate (0.268 g) were added; and the mixture was stirred at 70° C. for three hours. The reaction mixture was poured into water, the reaction mixture was extracted with ethyl acetate, and the insoluble substances were removed by celite filtration. The organic layer was washed with water and saturated saline and dried with anhydrous sodium sulfate. The residue, which was obtained by distilling the solvent under reduced pressure, was purified by silica gel column chromatography [elution solvent: n-hexane/ethyl acetate=1/1 to 0/1 (V/V)] to obtain 65 mg (yield: 15%) of the title compound as a pale yellow solid.

The results of analyzing the compounds of the examples by powder X-ray diffraction are shown below.

Analysis Conditions:
Model: Rigaku Rint TTR-III
Sample holder: Non-reflective sample holder
Sample: Appropriate amount
X-ray generation conditions: 50 kV, 300 mA
Wavelength: 1.54 Å (copper Kα radiation)
Scanning speed: 20°/min
Scanning range: 2 to 40°
Sampling width: 0.02°
Analysis operation: Several mg of the test substance was collected with a spatula, placed on a non-reflective sample holder, and flattened with a piece of weighing paper. Thereafter, peak patterns were analyzed under the conditions described above.

Example 4

When the maximum peak intensity is set to 100 in FIG. 1 of the diffraction pattern of powder X-ray diffraction (CuKα, λ=1.54 Å, scanning speed=20°/min), peaks with relative intensities of 4 or more are shown in Table 2.

TABLE 2

| Peak No. | 2θ | d value | Relative Intensity |
|---|---|---|---|
| 1 | 9.50 | 9.30 | 100 |
| 2 | 10.74 | 8.23 | 35 |

TABLE 2-continued

| Peak No. | 2θ | d value | Relative Intensity |
|---|---|---|---|
| 3 | 14.08 | 6.28 | 56 |
| 4 | 16.36 | 5.41 | 32 |
| 5 | 17.88 | 4.96 | 32 |
| 6 | 23.30 | 3.81 | 32 |
| 7 | 23.62 | 3.76 | 34 |
| 8 | 23.94 | 3.71 | 44 |
| 9 | 24.42 | 3.64 | 35 |
| 10 | 27.16 | 3.28 | 33 |

Example 5

When the maximum peak intensity is set to 100 in FIG. 2 of the diffraction pattern of powder X-ray diffraction (CuKα, λ=1.54 Å, scanning speed=20°/min), peaks with relative intensities of 4 or more are shown in Table 3.

TABLE 3

| Peak No. | 2θ | d value | Relative Intensity |
|---|---|---|---|
| 1 | 9.98 | 8.86 | 24 |
| 2 | 12.28 | 7.20 | 100 |
| 3 | 15.62 | 5.67 | 29 |
| 4 | 18.28 | 4.85 | 64 |
| 5 | 19.12 | 4.64 | 21 |
| 6 | 20.68 | 4.29 | 22 |
| 7 | 22.30 | 3.98 | 38 |
| 8 | 22.90 | 3.88 | 23 |
| 9 | 24.16 | 3.68 | 24 |
| 10 | 29.28 | 3.05 | 18 |

Example 17

When the maximum peak intensity is set to 100 in FIG. 3 of the diffraction pattern of powder X-ray diffraction (CuKα, λ=1.54 Å, scanning speed=20°/min), peaks with relative intensities of 4 or more are shown in Table 4.

TABLE 4

| Peak No. | 2θ | d value | Relative Intensity |
|---|---|---|---|
| 1 | 6.42 | 13.76 | 72 |
| 2 | 11.16 | 7.92 | 100 |
| 3 | 11.58 | 7.64 | 87 |
| 4 | 12.72 | 6.95 | 68 |
| 5 | 14.68 | 6.03 | 83 |
| 6 | 16.96 | 5.22 | 61 |
| 7 | 19.62 | 4.52 | 60 |
| 8 | 22.40 | 3.97 | 43 |
| 9 | 24.14 | 3.68 | 48 |
| 10 | 25.96 | 3.43 | 45 |

Example 25

When the maximum peak intensity is set to 100 in FIG. 4 of the diffraction pattern of powder X-ray diffraction (CuKα, λ=1.54 Å, scanning speed=20°/min), peaks with relative intensities of 4 or more are shown in Table 5.

TABLE 5

| Peak No. | 2θ | d value | Relative Intensity |
|---|---|---|---|
| 1 | 8.08 | 10.93 | 57 |
| 2 | 11.48 | 7.70 | 28 |
| 3 | 13.20 | 6.70 | 32 |
| 4 | 13.54 | 6.53 | 100 |
| 5 | 14.04 | 6.30 | 22 |
| 6 | 14.44 | 6.13 | 35 |
| 7 | 20.76 | 4.28 | 21 |
| 8 | 21.42 | 4.14 | 20 |
| 9 | 22.34 | 3.98 | 28 |
| 10 | 25.28 | 3.52 | 49 |

The structural formulas of the compounds described in examples and their physicochemical data are summarized below.

TABLE 6

| Example No. | Structural formula | Physicochemical data |
|---|---|---|
| 1(1a) | 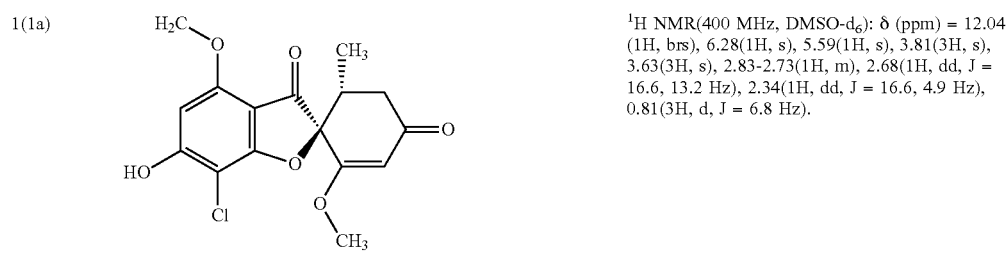 | $^1$H NMR(400 MHz, DMSO-$d_6$): δ (ppm) = 12.04 (1H, brs), 6.28(1H, s), 5.59(1H, s), 3.81(3H, s), 3.63(3H, s), 2.83-2.73(1H, m), 2.68(1H, dd, J = 16.6, 13.2 Hz), 2.34(1H, dd, J = 16.6, 4.9 Hz), 0.81(3H, d, J = 6.8 Hz). |
| 1(1b) | 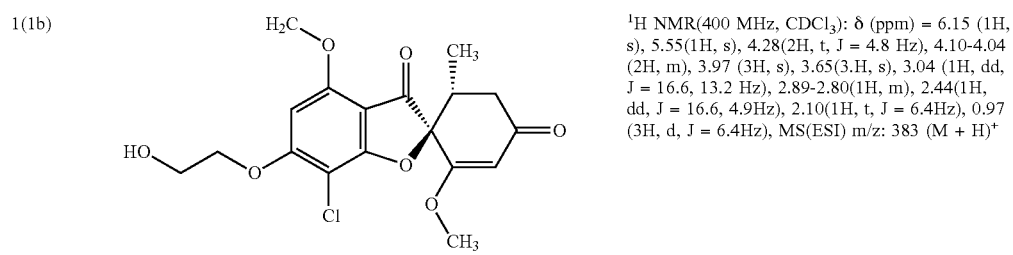 | $^1$H NMR(400 MHz, CDCl$_3$): δ (ppm) = 6.15 (1H, s), 5.55(1H, s), 4.28(2H, t, J = 4.8 Hz), 4.10-4.04 (2H, m), 3.97 (3H, s), 3.65(3.H, s), 3.04 (1H, dd, J = 16.6, 13.2 Hz), 2.89-2.80(1H, m), 2.44(1H, dd, J = 16.6, 4.9Hz), 2.10(1H, t, J = 6.4Hz), 0.97 (3H, d, J = 6.4Hz), MS(ESI) m/z: 383 (M + H)$^+$ |

TABLE 6-continued

| Example No. | Structural formula | Physicochemical data |
|---|---|---|
| 2 | | $^1$H NMR(400 MHz, CDCl$_3$): δ (ppm) = 6.19(1H, s), 5.54(1H, s), 4.31(2H, t, J = 4.4Hz), 3.95(3H, s), 3.85(2H, t, J = 4.4 Hz), 3.61(3H, s), 3.50(3H, s), 3.04(1H, dd, J = 16.6, 13.7 Hz), 2.89-2.79(1H, m), 2.43(1H, dd, J = 16.6, 4.4Hz), 0.95(3H, d, J = 6.8Hz). MS(ESI) m/z: 397 (M + H)$^+$ |
| 3(3a) | | $^1$H NMR(400 MHz, CDCl$_3$): δ (ppm) = 6.54(1H, s), 5.58(1H, s), 3.99(3H, s), 3.65(3H, s), 2.97(1H, dd, J = 16.6, 13.2 Hz), 2.93-2.81(1H, m), 2.48 (1H, dd, J = 16.1, 4.4 Hz), 0.98(3H, d, J = 6.8 Hz). |
| 3(3b) | | $^1$H NMR(400 MHz, CDCl$_3$): δ (ppm) = 7.49(1H, d, J = 2.4 Hz), 7.12(1H, s), 7.01(1H, d, J = 2.4 Hz), 5.57)1H, s), 4.02(3H, s), 4.02(3H, s), 3.63 (3H, s), 3.05(1H, dd, J = 16.6, 13.3 Hz), 2.95-2.82(1H, m), 2.46(1H, dd, J = 16.6, 4.3 Hz), 0.99 (3H, d, J = 6.7 Hz). MS(ESI) m/z: 403 (M + H)$^+$ |
| 4 | | $^1$H NMR(400 MHz, CDCl$_3$): δ (ppm) = 7.53(1H, d, J = 2.4 Hz), 7.14(1H, s), 7.01(1H, d, J = 2.4 Hz), 5.57(1H, s), 4.29(2H, q, J = 7.3 Hz), 4.03 (3H, s), 3.64(3H, s), 3.05(1H, dd, J = 16.6, 13.3 Hz), 2.94-2.83(1H, m), 2.47(1H, dd, J = 16.6, 4.9 Hz), 1.58(3H, t, J = 7.3 Hz), 1.00(3H, d, J = 6.4 Hz). MS(ESI) m/z: 417 (M + + H) |
| 5(5a) | | $^1$H NMR(400 MHz, CDCl$_3$): δ (ppm) = 7.48(2H, s), 7.23(1H, s), 5.59(1H, s), 4.05(3H, s), 3.65(3H, s), 3.00 (1H, dd, J = 16.1, 13.2 Hz), 2.95-2.82(1H, m), 2.50(1H, dd, J = 16.1, 4.4 Hz), 1.00 (3H, d, J = 6.8 Hz). |

TABLE 7

| Example No. | Structural formula | Physicochemical data |
| --- | --- | --- |
| 5(5b) | | $^1$H NMR(400 MHz, CDCl$_3$): δ (ppm) = 9.00 (1H, brd, J = 5.4 Hz), 8.59(1H, brd, J = 5.4 Hz), 6.88 (1H, s), 5.58(1H, s), 4.00(3H, s), 3.64(3H, s), 2.99 (1H, dd, J = 16.6, 13.2 Hz), 2.92-2.83(1H, m), 2.48(1H, dd, J = 16.6, 4.4 Hz), 2.17(3H, s,), 0.96(3H, d, J = 6.4Hz). |
| 5(5c) | | $^1$H NMR(400 MHz, CDCl$_3$): δ (ppm) = 7.23 (1H, s), 5.59(1H, s), 4.04(3H, s), 3.65(3H, s), 3.05-2.97(1H, m), 2.98-2.86(1H, m), 2.71(3H, s), 2.53-2.45(1H, m), 1.00(3H, d, J = 6.9 Hz). MS(ESI) m/z: 405 (M + H)$^+$ |
| 6(6a) | | $^1$H NMR(400 MHz, CDCl$_3$): δ (ppm) = 6.96 (1H, s), 5.57(1H, s), 5.03 (2H, brs), 4.00(3H, s), 3.64 (3H, s), 3.00(1H, dd, J = 16.6, 13.2 Hz), 2.93-2.83(1H, m), 2.48(1H, dd, J = 16.6, 4.4 Hz), 2.08(3H, s), 0.98(3H, d, J = 6.4 Hz). |
| 6(6b) | | $^1$H NMR(400 MHz, CDCl$_3$): δ (ppm) = 7.24 (1H, s), 5.59(1H, s), 4.05(3H, s), 3.65(3H, s), 3.00(1H, dd, J = 16.6, 13.2 Hz), 2.96-2.86(1H, m), 2.56(3H, s), 2.50(1H, dd, J = 16.6, 4.4 Hz), 1.00 (3H, d, J = 6.6 Hz). MS(ESI) m/z: 405 (M + H)$^+$ |
| 7(7a) | | $^1$H NMR(400 MHz, CDCl$_3$): δ (ppm) = 6.82 1H, s), 5.58(1H, s), 4.00(3H, s), 3.63(3H, s), 2.96 (1H, dd, J = 16.1, 13.2 Hz), 2.92-2.83 (1H, m), 2.49(1H, dd, J = 16.1, 3.9 Hz), 0.97 (3H, d, J = 6.4 Hz). |
| 7(7b) | | $^1$H NMR(400 MHz, CDCl$_3$): δ (ppm) = 7.12 (1H, s), 5.57(1H, s), 4.02(3H, s), 3.64(3H, s), 3.02(1H, dd, J = 16.6, 13.2 Hz), 2.95-2.85(1H, m), 2.73 (3H, s), 2.48(1H, dd, J = 16.6, 4.4 Hz), 1.00(3H, d, J =6.6 Hz). MS(ESI) m/z: 405 (M + H)$^+$ |

TABLE 8

| Example No. | Structural formula | Physicochemical data |
|---|---|---|
| 8(8a) | 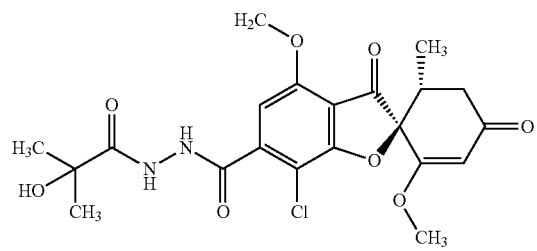 [SMILES: COC1=CC(=O)C[C@@H](C)[C@]12Oc1c(Cl)c(C(=O)NNC(=O)C(C)(C)O)cc(OC)c1C2=O] | ¹H NMR(400 MHz, CDCl₃): δ (ppm) = 9.39 (1H, brs), 8.83 (1H, brs), 6.91 (1H, s), 5.57 (1H, s), 4.00(3H, s), 3.64(3H, s), 3.00(1H, dd, J = 16.6, 13.2 Hz), 2.93-2.82(1H, m), 2.47(1H, dd, J = 16.6, 4.4 Hz), 2.43(1H, brs), 1.57 (6H, s), 0.97(3H, d, J = 6.4 Hz). |
| 8(8b) | 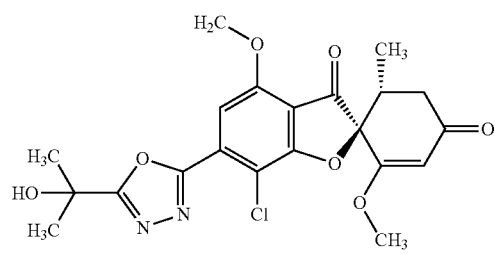 [SMILES: COC1=CC(=O)C[C@@H](C)[C@]12Oc1c(Cl)c(-c3nnc(C(C)(C)O)o3)cc(OC)c1C2=O] | ¹H NMR(400 MHz, CDCl₃): δ (ppm) = 7.25 (1H, s), 5.59(1H, s), 4.05(3H, s), 3.64 (3H, s), 3.01(1H, dd, J = 16.1, 13.2 Hz), 2.97-2.83(1H, m), 2.52(1H, m), 2.49(1H, dd, J = 16.1, 4.4 Hz), 1.81(6H, s), 1.00(3H, d, J = 6.4 Hz). MS(ESI) m/z: 449 (M + H)⁺ |
| 9(9a) | 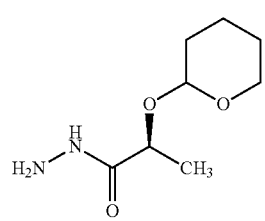 | ¹H NMR(400 MHz, CDCl₃): δ (ppm) = 7.89(0.3H, brs), 7.60 (0.7H, brs), 4.65-4.60(1H, m), 4.35-4.28(1H, m), 3.92-3.81 (3H, m), 3.55-3.46(1H, m), 1.90-1.72 (2H, m), 1.65-1.52 (4H, m), 1.48(2.1H, d, J = 6.8 Hz), 1.41(0.9H, J = 6.8 Hz). |
| 9(9b) | 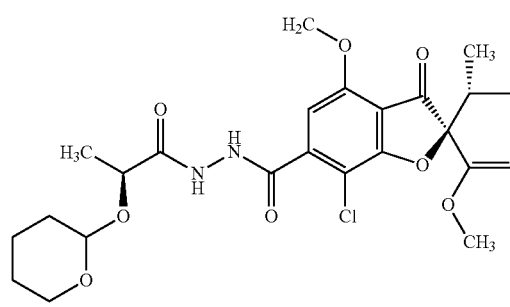 | ¹H NMR(400 MHz, CDCl₃): δ (ppm) = 9.71(0.2H, d, J = 6.8 Hz), 9.18 (0.8H, d, J = 5.9 Hz), 8.94(0.2H, d, J = 6.4 Hz), 8.90 (0.8H, d, J = 5.9Hz), 6.93(0.2H, s), 6.92(0.8H, s), 6.58(0.2H, s), 4.81-4.76(0.8H, m), 4.72-4.68 (0.2H, m), 4.50-4.41(1H, m), 3.99(3H, s), 3.97-3.90(1H, m), 3.58-4.54(4H, m), 3.00(1H, dd, J = 16.2, 13.2 Hz), 2.93-2.84(1H, m), 2.48(1H, dd, J = 16.2, 4.4 Hz), 1.96-1.46 (9H, m), 0.98(3H, d, J = 6.8 Hz). |
| 9(9c) | 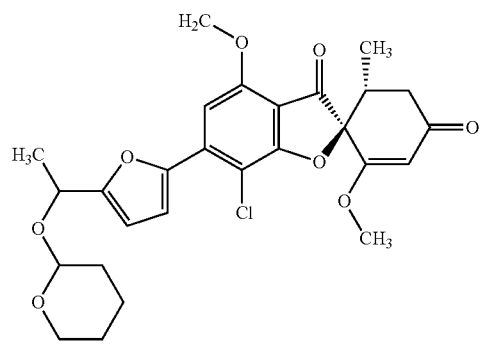 [SMILES: COC1=CC(=O)C[C@@H](C)[C@]12Oc1c(Cl)c(-c3ccc(C(C)OC4CCCCO4)o3)cc(OC)c1C2=O] | ¹H NMR(400 MHz, CDCl₃): δ (ppm) = 7.26(1H, s), 5.58(1H, s), 5.26(0.8H, q, J = 6.4 Hz), 5.17(0.2H, q, J = 6.4 Hz), 4.93-4.89(0.2H, m), 4.85-4.80(0.8H, m), 4.04(3H, s), 3.97-3.90(0.8H, m), 3.88-3.81(0.2H, m), 3.64 (3H, s), 3.63-3.57 (0.8H, m), 3.50-3.42(0.2H, m), 3.01(1H, dd, J = 16.2, 13.2 Hz), 2.95-2.85(1H, m), 2.49(1H, dd, J = 16.2, 4.4 Hz), 1.92-1.80 (1H, m), 1.78-1.69(5H, m), 1.68-1.50(3H, m), 1.00(3H, d, J = 6.4 Hz). |

TABLE 8-continued

| Example No. | Structural formula | Physicochemical data |
| --- | --- | --- |
| 9(9d) | | $^1$H NMR(400 MHz, CDCl$_3$): δ (ppm) = 7.24(1H, s), 5.58(1H, s), 5.26(1H, quintet J = 6.4 Hz), 4.04(3H, s), 3.64(3H, s), 3.01 (1H, dd, J = 16.6, 13.7 Hz), 2.95-2.85(1H, m), 2.55(1H, brs), 2.49(1H, dd, J = 16.6, 4.4 Hz), 1.78(3H, d, J = 6.4 Hz, 1.00(3H, d, J = 6.8 Hz). MS(ESI) m/z: 435 (M + H)$^+$ |

TABLE 9

| Example No. 1 | Structural formula | Physicochemical data |
| --- | --- | --- |
| 10(10a) | | $^1$H NMR(400 MHz, CDCl$_3$): δ (ppm) = 7.89(0.3H, brs), 7.60(0.7H, brs), 4.67-4.60(1H, m), 4.36-4.27 (1H, m), 3.96-3.78(3H, m), 3.57-3.46(1H, m), 1.91-1.72 (2H, m), 1.65-1.52(4H, m), 1.48(2.1H, d, J = 6.8 Hz), 1.42(0.9H, d, J = 6.8 Hz). |
| 10(10b) | | $^1$H NMR(400 MHz, CDCl$_3$): δ (ppm) = 9.72(0.3H, d, J = 6.4 Hz), 9.19(0.7H, d, J = 6.4 Hz), 9.00(0.3H, d, J = 6.4 Hz), 8.96(0.7H, d, J = 6.4 Hz), 6.93(0.3H, s), 6.92(0.7H, s), 5.57(1H, s), 4.83-4.76(0.7H, m), 4.74-4.67(0.3H, m), 4.52-4.40(1H, m), 4.07-3.88(4H, m), 3.71-3.53(4H, m), 3.06-2.82(2H, m), 2.48(1H, dd, J = 16.6, 4.4 Hz), 1.98-1.45 (9H, m), 0.97(3H, d, J = 6.4 Hz). |
| 10(10c) | | $^1$H NMR(400 MHz, CDCl$_3$): δ (ppm) = 7.27(1H, s), 5.58(1H, s), 5.30(0.7H, q, J = 6.8 Hz), 5.16(0.3H, q, J = 6.8 Hz), 4.93-4.89(0.3H, m), 4.85-4.80 (0.7H, m), 4.04(3H, s), 3.97-3.90(0.7H, m), 3.89-3.81 (0.3H, m), 3.64(3H, s), 3.63-3.56(0.7H, m), 3.50-3.41(0.3H, m), 3.05-2.85(2H, m), 2.53-2.45(1H, m), 1.93-1.46(9H, m), 0.99(3H, d, J = 6.8 Hz). |
| 10(10d) | | $^1$H NMR(400 MHz, CDCl$_3$): δ (ppm) = 7.24(1H, s), 5.58(1H, s), 5.26(1H, quintet J = 6.8 Hz), 4.04 (3H, s), 3.64(3H, s), 3.01(1H, dd, J = 16.2, 13.2 Hz), 2.95-2.85(1H, m), 2.56(1H, brs), 2.49(1H, dd, J = 16.6 4.4 Hz), 1.78 (3H, d, J = 6.8 Hz), 1.00 (3H, d, J = 6.8 Hz). \MS(ESI) m/z: 435 (M + H)$^+$ |

TABLE 9-continued

| Example No. 1 | Structural formula | Physicochemical data |
|---|---|---|
| 11(11a) | | $^1$H NMR(400 MHz, CDCl$_3$): δ (ppm) = 7.28 (1H, s), 5.61(1H, s), 4.04(1H, s), 3.68(3H, s), 3.05-2.87 (2H, m), 2.59-2.52 (1H, m), 1.80(6H, s), 1.02(3H, d, J = 6.4 Hz). |
| 11(11b) | | $^1$H NMR(400 MHz, CDCl$_3$): δ (ppm) = 7.22(1H, s), 5.57(1H, s), 4.31-4.23(2H, m), 3.64(3H, s), 3.02 (1H, dd, J = 16.6, 13.7 Hz), 2.95-2.85(1H, m), 2.56-2.42(2H, m), 1.81 (6H, s), 1.54(3H, t, J = 6.8 Hz), 1.00(3H, d, J = 6.4 Hz). MS(ESI) m/z: 463 (M+ H)$^+$ |

TABLE 10

| Example No. | Structural formula | Physicochemical data |
|---|---|---|
| 12 | | $^1$H NMR(400 MHz, CDCl$_3$): δ (ppm) = 7.22(1H, s), 5.57(1H, s), 5.31-5.25(1H, m), 4.32-4.22(2H, m), 3.54(3H, s), 3.03(1H, dd, J = 16.6, 13.2 Hz), 2.96-2.85(1H, m), 2.52-2.44(2H, m), 1.78(3H, d, J = 6.4 Hz), 1.54(3H, t, J = 6.8 Hz), 1.00(3H, d, J = 6.4 Hz). MS(ESI) m/z: 449 (M + H)$^+$ |
| 13(13a) | | $^1$H NMR(400 MHz, CDCl$_3$): δ (ppm) = 4.93-4.86(1H, m), 4.65(1H, q, J = 6.8 Hz), 3.82-3.72(1H, m), 3.60- $^1$H NMR(400 MHz, CDCl$_3$): δ (ppm) = 4.81-4.77(1H m), 4.39(1H, q, J = 6.8 Hz), 3.97(1H, td, J = 11.7, 2.9 Hz), 3.67-3.60(1H, m), 1.90-1.52(9H, m). |
| 13(13b) | | $^1$H NMR(400 MHz, CDCl$_3$): δ (ppm) = 7.70(1H, brs), 4.70 (2H, brs), 4.63-4.58(1H, m), 4.36(1H, q, J = 6.8 Hz), 3.93-3.83(1H, m), 3.56-3.48(1H, m), 1.90-1.78(1H, m), 1.75-1.66(1H, m), 1.63-1.49(4H m), 1.44(3H, d, J = 6.8 Hz). |

TABLE 10-continued

| Example No. | Structural formula | Physicochemical data |
| --- | --- | --- |
| 13(13c) | | $^1$H NMR(400 MHz, CDCl$_3$): δ (ppm) = 6.97 (1H, brs), 5.57(1H, s), 5.21(2H, brs), 4.78-4.61(2H, m), 4.00(3H, s), 3.94-3.85(1H, m), 3.63(3H, s), 3.59-3.51(1H, m), 3.00(1H, dd, J = 16.6, 13.7 Hz), 2.93-2.82(1H, m), 2.48(1H, dd, J = 16.6, 4.4 Hz), 1.90-1.79(1H, m), 1.78-1.69(1H, m), 1.63-1.49(7H, m), 0.98(3H, d, J = 6.8 Hz). |
| 13(13d) | | $^1$H NMR(400 MHz, CDCl$_3$): δ (ppm) = 7.247(1H, s), 5.58(1H, s), 5.23(1H, q, J = 6.8 Hz), 4.79-4.70(1H, m), 4.05(3H, s), 3.99-3.92(1H, m), 3.63(3H, s), 3.62-3.56(1H, m), 3.00(1H, dd, J = 16.6, 13.7 Hz), 2.95-2.85(1H, m), 2.49(1H, dd, J = 16.6, 4.4 Hz), 1.94-1.83(1H, m), 1.78-1.50(8H, m), 0.99(3h, d, J = 6.8 Hz). |
| 13(13e) | | $^1$H NMR(400 MHz, CDCl$_3$): δ (ppm) = 7.25(1H, s), 5.58(1H, s), 5.17(1H, quintet, J = 6.8 Hz), 4.06(3H, s), 3.64(3H, s), 3.00(1H, dd, J = 16.6, 13.2 Hz), 2.96-2.85(1H, m), 2.50(1H, dd, J = 16.6, 4.4 Hz), 2.48-2.43(1H, m), 1.73(3H, d, J = 6.8 Hz), 1.00(3H, d, J = 6.4 Hz). MS(ESI) m/z: 435 (M + H)$^+$. |

TABLE 11

| Example No. | Structural formula | Physicochemical data |
| --- | --- | --- |
| 14(14a) | | $^1$H NMR(400 MHz, CDCl$_3$): δ (ppm) = 7.76(1H, brs), 6.19(1H, s), 5.57(1H, s), 3.98(3H, s), 3.66 (3H, s), 3.00-2.82(2H, m), 2.49(1H, dd, J = 16.6, 4.4 Hz), 0.99 (3H, d, J = 6.4 hz). |

TABLE 11-continued

| Example No. | Structural formula | Physicochemical data |
|---|---|---|
| 14(14b) | | $^1$H NMR(400 MHz, CDCl$_3$): δ (ppm) = 6.26(1H, s), 5.54(1H, s), 4.75-4.69(1H, m), 4.40-4.29(2H, m), 4.15-4.08(1H, m), 4.00(3H, s), 3.96-3.85(2H, m), 3.62 (3H, s), 3.57-3.50(1H, m), 3.03(1H, dd, J = 16.6, 13.2 Hz), 2.89-2.79(1H, m), 2.46-2.39 (1H, m), 1.88-1.68(2H, m), 1.62-1.45(4H, m), 0.96(3H, d, J = 6.8 Hz). |
| 14(14c) | | $^1$H NMR(400 MHz, CDCl$_3$): δ (ppm) = 6.30 (1H, s), 5.54(1H, s), 4.78-4.71(1H, m), 4.30-4.21(2H, m), 4.12-4.04(1H, m), 3.95-3.84(2H, m), 3.63(3H, s), 3.57-3.50(1H, m), 3.04(1H, dd, J = 16.6, 13.2 Hz), 2.88-2.77(1H, m), 2.46-2.39 (1H, m), 1.85-1.47(6H, m), 0.97 (3H, d, J = 6.8 Hz). |
| 14(14d) | | $^1$H NMR(400 MHz, CDCl$_3$): δ (ppm) = 6.67(1H, s), 5.57(1H, s), 4.75-4.70(1H, m), 4.37-4.28(2H, m), 4.15-4.07(1H, m), 3.93-3.84(2H, m), 3.65(3H, s), 3.57-3.51(1H, m), 3.01-2.93(1H, m), 2.92-2.81(1H, m), 2.52-2.44(1H, m), 1.84-1.68(2H, m), 1.65-1.46(4H, m), 0.98(3H, d, J = 6.8 Hz). |

TABLE 11-continued
| Example No. | Structural formula | Physicochemical data |
|---|---|---|
| 14(14e) | 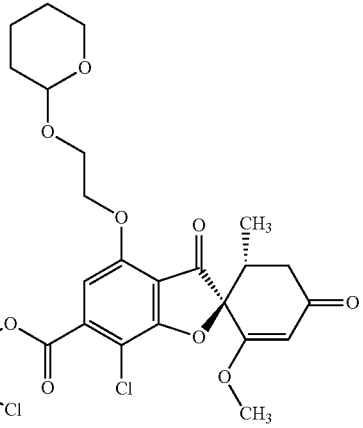 | $^1$H NMR(400 MHz, CDCl$_3$): δ (ppm) = 7.47 (2H, s), 7.32(1H, s), 5.58(1H, s), 4.76-4.72 (1H, m), 4.44-4.36(2H, m), 4.17-4.07(1H, m), 3.96-3.84(2H, m), 3.65(3H, s), 3.57-3.49(1H, m), 3.04-2.96(1H, m), 2.95-2.86(1H, m), 2.52-2.44(1H, m), 1.83-1.67(2H, m), 1.64-1.44(4H, m), 0.99(3H, d, J = 6.8 Hz). |
TABLE 12
| Example No. | Structural formula | Physicochemical data |
|---|---|---|
| 14(14f) | 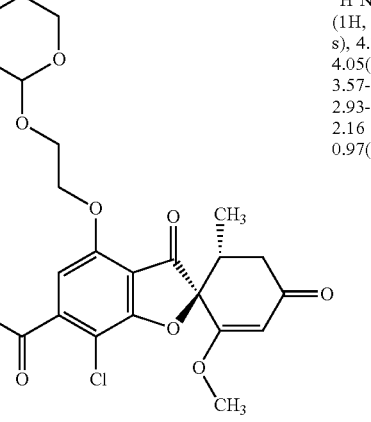 | $^1$H NMR(400 MHz, CDCl$_3$): δ (ppm) = 8.97-8.86 (1H, m), 8.45-8.32(1H, m), 6.96(1H, s), 5.56(1H, s), 4.77-4.70(1H, m), 4.40-4.29(2H, m), 4.14-4.05(1H, m), 3.94-3.84(2H, m), 3.64(3H, s), 3.57-3.50(1H, m), 3.00(1H, dd, J = 16.1, 13.6 Hz), 2.93-2.82(1H, m), 2.47(1H, dd, J = 16.6, 3.9 Hz), 2.16 (3H, s), 1.87-1.67(2H, m), 1.64-1.46(4H, m), 0.97(3H, d, J = 6.8 Hz). |
| 14(14g) | 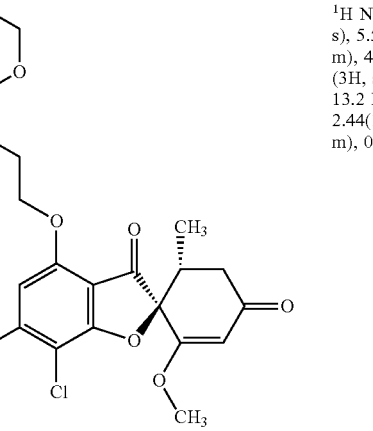 | $^1$H NMR(400 MHz, CDCl$_3$): δ (ppm) = 7.29(1H, s), 5.57(1H, s), 4.78-4.72(1H, m), 4.43-4.33(2H, m), 4.16-4.08(1H, m), 3.96-3.85(2H, m), 3.64 (3H, s), 3.58-3.51(1H, m), 3.01(1H, dd, J = 16.1, 13.2 Hz), 2.95-2.85(1H, m), 2.70(3H, s), 2.52-2.44(1H, m), 1.85-1.68(2H, m), 1.64-1.47(4H, m), 0.99(3H, d, J = 6.4 Hz). |

TABLE 12-continued
| Example No. | Structural formula | Physicochemical data |
|---|---|---|
| 14(14h) | 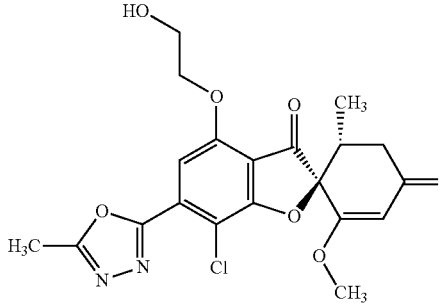 | $^1$H NMR(400 MHz, CDCl$_3$): δ (ppm) = 7.25(1H, s), 5.58(1H, s), 4.33-4.23(2H, m), 4.10-3.96(2H, m), 3.65(3H, s), 3.04-2.85(2H, m), 2.71(2H, s), 2.60-2.46(2H, m), 1.00(3H, d, J = 6.8 Hz). MS(ESI) m/z: 435(M + H)$^+$ |
| 15(15a) | 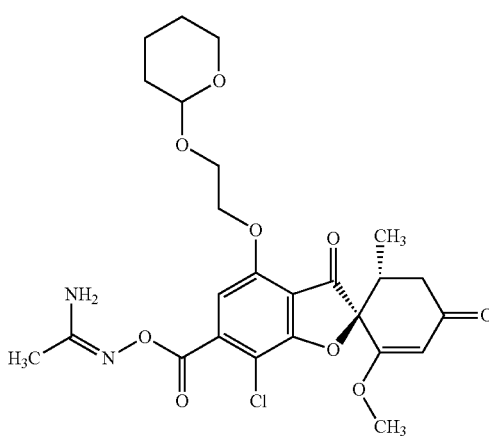 [SMILES: COC1=CC(=O)C[C@@H](C)[C@]12Oc1c(Cl)c(C(=O)O/N=C(/C)N)cc(OCCOC3CCCCO3)c1C2=O] | $^1$H NMR(400 MHz, CDCl$_3$): δ (ppm) = 7.04(1H, s), 5.56(1H, s), 4.78-4.72(1H, m), 4.40-4.29(2H, m), 4.14-4.06(1H, m), 3.93-3.84(2H, m), 3.64 (3H, s), 3.57-3.50(1H, m), 3.00(1H, dd, J = 16.6, 13.2 Hz), 2.93-2.82(1H, m), 2.47(1H, dd, J = 16.6, 3.2 Hz), 2.08(3H, s), 1.85-1.67(2H, m), 1.64-1.47(4H, m), 0.97(3H, d, J = 6.4Hz). |
| 15(15b) | 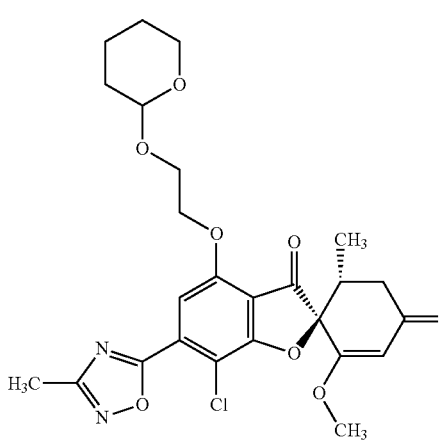 | $^1$H NMR(400 MHz, CDCl$_3$): δ (ppm) = 7.33 (1H, s), 5.57(1H, s), 4.78-4.72(1H, m), 4.45-4.34(2H, m), 4.16-4.08(1H, m), 3.96-3.83 (2H, m), 3.54(3H, s), 3.58-3.51(1H, m), 3.00 (1H, dd, J = 16.1, 13.2Hz), 2.95-2.86(1H, m), 2.54(3H, s), 2.48(1H, dd, J = 16.1 3.2 Hz), 1.85-1.68(2H, m), 1.64-1.47(4H, m), 0.99(3H, d, J = 6.4 Hz). |

TABLE 13

| Example No. | Structural formula | Physicochemical data |
|---|---|---|
| 15(15c) | | $^1$H NMR(400 MHz, CDCl$_3$): δ (ppm) = 7.25(1H, s), 5.58(1H, s), 4.33-4.25(2H, m), 4.09-3.98(2H, m), 3.65 (3H, s), 2.99(1H, dd, J = 16.1, 13.2 Hz), 2.96-2.87(1H, m), 2.55(3H, s), 2.54 (1H, d, J = 6.4 Hz) 2.50(1H, dd, J = 16.1, 3.9 Hz), 1.00 (3H, d, J = 6.4 Hz). MS(ESI) m/z: 435 (M + H)$^+$ |
| 16(16a) | | $^1$H NMR(400 MHz, CDCl$_3$): δ (ppm) = 7.72(1H, brs), 7.16 (1H, s), 5.60(1H, s), 3.68(3H, s), 3.10-2.85(2H, m), 2.72(3H, s), 2.59-2.43(1H, m), 1.01(3H, d, J = 6.4Hz). |
| 16(16b) | | $^1$H NMR(400 MHz, CDCl$_3$): δ (ppm) = 7.15(1H, s), 5.58(1H, s), 4.38-4.32(2H, m), 4.15-3.95(2H, m), 3.66(3H, s), 3.08-2.85(2H, m), 2.74(3H, s), 2.49(1H, dd, J = 16.1, 3.9 Hz), 1.00(3H, d, J = 6.4 Hz). MS(ESI) m/z: 435 (M + H)$^+$ |
| 17(17a) | | $^1$H NMR(500 MHz, CDCl$_3$): δ (ppm) = 9.13 (1H, brd, J = 5.4 Hz), 8.59 (1H, brd, J = 5.4 Hz), 6.89 (1H, s), 5.58 (1H, s), 3.99 (3H, s), 3.63 (3H, s), 2.99 (1H, J = 16.6 13.2 Hz), 2.92-2.84 (1H, m), 2.47 (1H, dd, J = 16.6, 4.4 Hz), 2.41 (2H, q, J = 7.6 Hz), 1.27 (3H, t, J = 7.6 Hz), 0.96 (3H, d, J = 6.8 Hz). |
| 17(17b) | | $^1$H NMR(500 MHz, CDCl$_3$): δ (ppm) = 7.24 (1H, s), 5.58 (1H, s), 4.02 (3H, s), 3.64 (3H, s), 3.06-2.97 (3H, m), 2.91-2.89 (1H, m), 2.48 (1H, d, J = 16.6 Hz), 1.48 (3H, t, J = 7.6 Hz), 0.99 (3H, d, J = 6.8 Hz). MS(APCI) m/z: 419 (M + H)$^+$ |

TABLE 13-continued

| Example No. | Structural formula | Physicochemical data |
| --- | --- | --- |
| 18(18a) | | $^1$H NMR(500 MHz, CDCl$_3$): δ (ppm) = 9.01 (1H, brd, J = 5.4 Hz), 8.51 (1H, brd, J = 5.4 Hz), 6.90 (1H, s), 5.57 (1H, s), 4.10-4.03 (2H, m), 4.00 (3H, s), 3.63 (3H, s), 3.47 (2H, rd, J = 11.7, 2.4 Hz), 2.99 (1H, dd, J = 16.6, 13.2 Hz), 2.91-2.84 (1H, m), 2.64-2.52 (1H, m), 2.47 (1H, dd, J = 16.6, 4.4 Hz), 1.97-1.89 (2H, m), 1.88-1.79 (2H, m), 0.97 (3H, d, J = 6.8 Hz). |
| 18(18b) | | $^1$H NMR(500 MHz, CDCl$_3$): δ (ppm) = 7.23(1H, s), 5.58 (1H, s), 4.10 (2H, td, J = 11.2, 3.9 Hz), 4.40 (3H, s), 3.64 (3H, s), 3.61 (2H, td, J = 11.2, 2.6 Hz), 3.37-3.31 (1H, m), 3.01 (1H, dd, J = 16.6, 13.2 Hz), 2.95-2.85 (1H, m), 2.49 (1H, dd, J = 16.6, 4.4 Hz), 2.19-2.00 (4H, m), 0.99 (3H, d, J = 6.3 Hz). MS(APCl) m/z: 475 . (M + H)$^+$ |

TABLE 14

| Example No. | Structural formula | Physicochemical data |
| --- | --- | --- |
| 19(19a) | | $^1$H NMR(500 MHz, CDCl$_3$): δ (ppm) = 7.42 (1H, brs), 6.79 (1H, s), 5.56 (1H, s), 4.18 (2H, brs), 3.98 (3H, s), 3.63 (3H, s), 2.99 (1H, dd, J = 16.6, 13.2 Hz) 2.90-2.83 (1H, m), 2.47 (1H, dd, J = 16.6, 4.4 Hz), 0.96 (3H, d, J = 6.8 Hz). |
| 19(19b) | | $^1$H NMR(500 MHz, CDCl$_3$): δ (ppm) = 7.26 (1H, s), 5.58 (1H, s), 4.03 (3H, s), 3.64 (3H, s), 3.06-2.88 (5H, m), 2.48 (1H, dd, J = 16.6, 4.4 Hz), 2.34 (3H, s), 2.18-2.16 (4H, m), 2.07-2.04 (2H, m), 0.99 (3H, d, J = 6.3 Hz). MS(APCl) m/z: 488 (M + H)$^+$ |
| 20 | | $^1$H NMR(500 MHz, CDCl$_3$): δ (ppm) = 7.26 (1H, s), 5.58(1H, s), 4.05 (3H, s), 3.64 (3H, s), 3.00 (1H, dd, J = 16.6, 13.2 Hz), 2.94-2.87 (1H, m), 2.75-2.73 (2H, m), 2.55-2.53 (2H, m), 2.49 (1H, dd, J = 16.6, 4.4 Hz), 2.46-2.39 (4H, m), 2.37 (3H, s), 0.99 (3H, d, J = 6.3 Hz). MS(APCl) m/z: 506 (M + H)$^+$ |

TABLE 14-continued

| Example No. | Structural formula | Physicochemical data |
|---|---|---|
| 21(21a) | 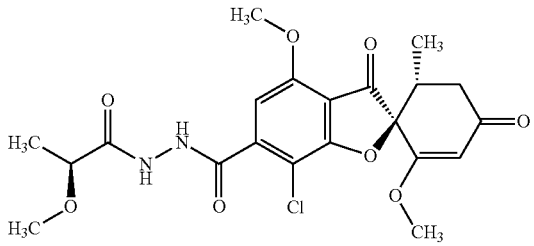 [SMILES: COC1=CC(=O)C[C@@H](C)[C@]12Oc1c(Cl)c(C(=O)NNC(=O)[C@H](C)OC)cc(OC)c1C2=O] | $^1$H NMR(500 MHz, CDCl$_3$): δ (ppm) = 9.12 (1H, d, J = 5.9 Hz), 8.74 (1H, d, J = 5.9 Hz), 6.91 (1H, s), 5.57 (1H, s), 4.01-3.96 (4H, m), 3.63 (3H, s), 3.51 (3H, s), 2.99 (1H, dd, J = 16.6, 13.2 Hz), 2.91 2.84 (1H, m), 2.47 (1H, dd, J = 16.6, 4.4 Hz), 1.49 (3H, d, J = 6.8 Hz), 0.97 (3H, d, J = 6.8 Hz). |
| 21(21b) | 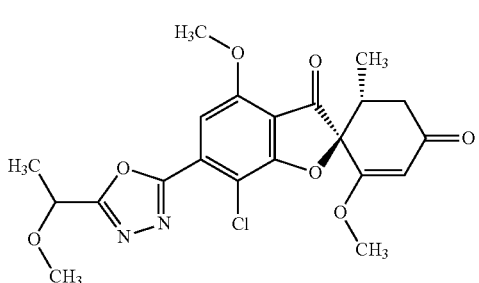 | $^1$H NMR(500 MHz, CDCl$_3$): δ (ppm) = 7.25 (1H, s), 5.58 (1H, s), 4.78 (1H, q, J = 6.8 Hz), 4.05 (3H, s), 3.64 (3H, s), 3.46 (3H, s), 3.01 (1H, dd, J = 16.4, 13.4 Hz), 2.94-2.87 (1H, m), 2.49 (1H, dd, J = 16.6, 4.4 Hz), 1.71 (3H, d, J = 6.8 Hz), 0.99 (3H, d, J = 6.8 Hz). MS(APCI) m/z: 449 (M + H)$^+$ |
| 22(22a) | 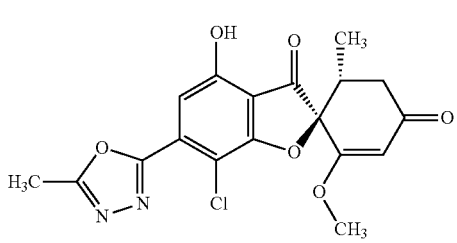 [SMILES: COC1=CC(=O)C[C@@H](C)[C@]12Oc1c(Cl)c(-c3nnc(C)o3)cc(O)c1C2=O] | $^1$H NMR(500 MHz, CDCl$_3$): δ (ppm) = 7.77 (1H, brs), 7.28 (1H, s), 5.60 (1H, s), 3.68 (3H, s), 3.01-2.85 (2H, m), 2.71 (3H, s), 2.61-2.47 (1H, m), 1.02 (3H, d, J = 6.3 Hz). |
| 22(22b) | 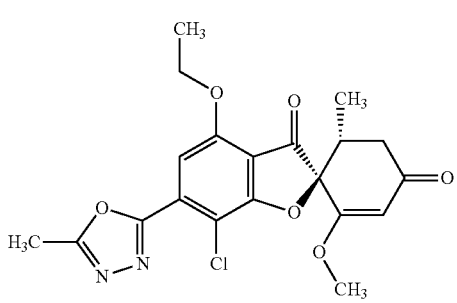 [SMILES: CCOc1cc(-c2nnc(C)o2)c(Cl)c2c1C(=O)[C@@]1(O2)C(OC)=CC(=O)C[C@H]1C] | $^1$H NMR(500 MHz, CDCl$_3$): δ (ppm) = 7.20 (1H, s), 5.58 (1H, s), 4.32-4.21 (2H, m), 3.64 (3H, s), 3.02 (1H, dd, J = 16.6, 13.2 Hz), 2.94-2.86 (1H, m), 2.71 (3H, s), 2.48 (1H, dd, J = 16.6, 4.4 Hz), 1.54 (3H, t, J = 7.1 Hz), 1.00 (3H, d, J = 6.8 Hz). MS(APCI) m/z: 419 (M + H)$^+$ |

TABLE 15

| Example No. | Structural formula | Physicochemical data |
|---|---|---|
| 23(23a) | 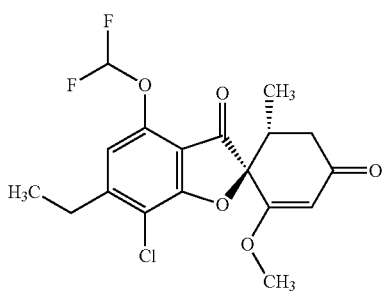 [SMILES: CCc1cc(OC(F)F)c2c(c1Cl)O[C@]1(C2=O)C(OC)=CC(=O)C[C@H]1C] | $^1$H NMR(500 MHz, CDCl$_3$): δ (ppm) = 6.91 (1H, t, J = 73.5 Hz), 6.50 (1H, s), 5.57 (1H, s), 4.03 (3H, s), 3.64 (3H, s), 2.97 (1H, dd, J = 16.6, 13.2 Hz), 2.88-2.86 (1H, m), 2.46 (1H, dd, J = 16.6, 4.4 Hz), 0.96 (3H, d, J = 6.8 Hz). MS(APCI) m/z: 389 (M + H)$^+$ |

TABLE 15-continued

| Example No. | Structural formula | Physicochemical data |
|---|---|---|
| 23(23b) | | $^1$H NMR(500 MHz, CDCl$_3$): δ (ppm) = 6.80 (1H, t, J = 72.7 Hz), 6.57 (1H, s), 5.58 (1H, s), 3.66 (3H, s), 3.00 (1H, dd, J = 16.6, 13.7 Hz), 2.90-2.82 (1H, m), 2.47 (1H, dd, J = 16.6, 4.9 Hz), 0.97 (3H, d, J = 6.8 Hz). |
| 23(23c) | | $^1$H NMR(500 MHz, CDCl$_3$): δ (ppm) = 6.91 (1H, s), 6.82 (1H, t, J = 72.0 Hz), 5.60 (1H, s), 3.67 (3H, s), 2.98-2.84 (2H, m), 2.52 (1H, brd, J = 12.2 Hz), 0.98 (3H, d, J = 6.3 Hz). |
| 23(23d) | | $^1$H NMR(500 MHz, CDCl$_3$): δ (ppm) = 7.57 (1H, s), 7.48 (2H, s), 5.85 (1H, t, J = 72.0 Hz), 5.61 (1H, s), 3.67 (3H, s), 3.04-2.87 (2H, m), 2.52 (1H, brd, J = 12.2 Hz), 1.00 (3H, d, J = 6.3 Hz). |
| 23(23e) | | $^1$H NMR(500 MHz, CDCl$_3$): δ (ppm) = 9.11 (1H, s), 8.62 (1H, s), 7.18 (1H, s), 6.80 (1H, t, J = 72.2 Hz), 5.60 (1H, s), 3.66 (3H, s), 2.98-2.86 (2H, m), 2.50 (1H, dd, J = 16.6, 4.4 Hz), 2.17 (3H, s), 0.97 (3H, d, J = 6.3 Hz). |
| 23(23f) | | $^1$H NMR(500 MHz, CDCl$_3$): δ (ppm) = 7.53 (1H, s), 6.84 (1H, t, J = 72.0 Hz), 5.60 (1H, s), 3.66 (3H, s), 3.03-2.88 (2H, m), 2.71 (3H, s), 2.52 (1H, d, J = 12.7 Hz), 1.00 (3H, d, J = 6.3 Hz). MS(ESI) m/z: 441 (M + H)$^+$ |

TABLE 15-continued

| Example No. | Structural formula | Physicochemical data |
| --- | --- | --- |
| 24(24a) | 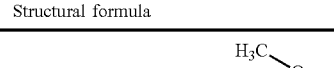 | $^1$H NMR(500 MHz, CDCl$_3$): δ (ppm) = 6.97 (1H, s), 5.57 (1H, s), 5.21 (2H, brs), 4.08 (1H, q, J = 13.2 Hz), 4.00 (3H, s), 3.63 (3H, s), 3.39 (3H, s), 3.00 (1H, dd, J = 16.6, 13.2 Hz), 2.92-2.84 (1H, m), 2.48 (1H, dd, J = 16.6, 4.4 Hz), 1.49 (3H, d, J = 6.8 Hz), 0.98 (3H, d, J = 6.3 Hz). |

TABLE 16

| Example No. | Structural formula | Physicochemical data |
| --- | --- | --- |
| 24(24b) |  | $^1$H NMR(500 MHz, CDCl$_3$): δ (ppm) = 7.29 (1H, s), 5.58 (1H, s), 4.70 (1H, q, J = 6.7 Hz), 4.05 (3H, s), 3.64 (3H, s), 3.44 (3H, s), 3.00 (1H, dd, J = 16.1, 13.2 Hz), 2.94-2.87 (1H, m), 2.49 (1H, dd, J = 16.4, 4.1 Hz), 1.66 (3H, d, J = 6.7 Hz), 0.99 (3H, d, J = 6.3 Hz). MS(APCl) m/z: 449 (M + H)$^+$ |
| 25(25a) |  | $^1$H NMR(500 MHz, CDCl$_3$): δ (ppm) = 6.93 (1H, s), 5.57 (1H, s), 5.40 (2H, brs), 3.99 (3H, s), 3.64 (3H, s), 3.00 (1H, dd, J = 16.6, 13.7 Hz), 2.92-2.84 (1H, m), 2.47 (1H, dd, J = 16.4, 4.6 Hz), 2.03 (1H, s), 1.63 (6H, s), 0.98 (3H, d, J = 6.3 Hz). |
| 25(25b) |  | $^1$H NMR(500 MHz, CDCl$_3$): δ (ppm) = 7.23 (1H, s), 5.58 (1H, s), 4.06 (3H, s), 3.64 (3H, s), 3.00 (1H, dd, J = 16.1, 13.2 Hz), 2.95-2.87 (1H, m), 2.58 (1H, s), 2.49 (1H, dd, J = 16.4, 4.1 Hz), 1.75 (6H, s), 0.99 (3H, d, J = 6.3 Hz), MS(APCl), m/z: 449 (M + H) |
| 26(26a) |  | $^1$H NMR(400 MHz, CDCl$_3$): δ (ppm) = 7.72 (1H, d, J = 2.0 Hz), 6.83 (1H, d, J = 3.2 Hz), 6.56-6.55 (1H, m), 5.61 (1H, d, J = 4.0 Hz), 5.17-5.13 (1H, m), 4.11-4.06 (1H, m), 3.97 (3H, s), 3.69 (3H, d, J = 4.8 Hz), 3.59-3.52 (1H, m), 3.09-2.99 (1H, m), 2.96-2.88 (1H, m), 2.65-2.56 (1H, m), 2.54-2.48 (1H, m), 2.17-2.09 (1H, m), 2.02-1.94 (1H, m), 1.82-1.71 (1H, m), 1.58-1.56 (1H, m), 1.06-1.02 (3H, m) 0.90-0.87 (1H, m). |

TABLE 16-continued

| Example No. | Structural formula | Physicochemical data |
|---|---|---|
| 26(26b) | | $^1$H NMR(400 MHz, DMSO-d$_6$): d(ppm) = 13.42 (1H, s), 7.94 (1H, s), 7.18 (1H, s), 7.00 (1H, d, J = 2.0 Hz), 5.65 (1H, s), 3.95 (3H, s), 3.65 (3H, s), 2.90-2.83 (1H, m), 2.73-2.65 (1H, m), 2.43-2.37 (1H, m), 0.85 (3H, d, J = 6.4 Hz). MS(ESI) m/z: 389 (M + H) $^+$ |
| 27 | | $^1$H NMR(400 MHz, DMSO-d$_6$): d(ppm) = 7.92 (1H, d, J = 2.4 Hz), 7.13 (1H, s), 6.98 (1H, d, J = 2.4 Hz), 5.65 (1H, s), 4.39 (2H, t, J = 5.2 Hz), 3.94 (3H, s), 3.75 (2H, t, J = 5.2 Hz), 3.65 (3H, s), 3.26 (3H, s), 2.90-2.83 (1H, m), 2.72-2.65 (1H, m), 2.42-2.37 (1H, m), 0.85 (3H, d, J = 6.4 Hz). MS(ESI) m/z: 447 (M + H)$^+$ |

TABLE 17

| Example No. | Structural formula | Physicochemical data |
|---|---|---|
| 28(28a) | | $^1$H NMR(300 MHz, CDCl$_3$): δ (ppm) = 10.48 (1H, s), 7.01 (1H, s), 5.51 (1H, s), 3.95 (3H, s), 3.57 (3H, s), 3.57 (3H, s), 2.86-2.73 (1H, m), 2.44-2.38 (1H, m), 2.03-1.92 (1H, m), 0.91 (3H, d, J = 6.4 Hz). |
| 28(28b) | | $^1$H NMR(400 MHz, CDCl$_3$): δ (ppm) = 6.97 (1H, s), 5.66 (1H, s), 3.94 (3H, s), 3.83-3.74 (2H, m), 3.65 (3H, s), 3.63-3.57 (2H, s), 3.42 (2H, s), 2.94-2.82 (1H, m), 2.73-2.61 (1H, m), 2.45-2.35 (1H, m), 1.88-1.80 (4H, m), 0.83 (3H, d, J = 6.8 Hz). MS(ESI) m/z: 462 (M + H) $^+$ |
| 29 | | $^1$H NMR(400 MHz, CDCl$_3$): δ (ppm) = 6.94 (1H, s), 5.57 (1H, s), 3.98 (3H, s), 3.63 (3H, s), 3.35 (2H, s), 3.07-2.98 (1H, m), 2.94-2.82 (1H, m), 2.65-2.55 (4H, m), 2.47 (1H, dd, J = 16.4, 4.2 Hz), 2.36 (3H, s), 2.09-2.03 (2H, m), 1.95-1.90 (2H, m), 0.97 (3H, d, J = 6.8 Hz). MS(ESI) m/z: 475 (M + H)$^+$ |

TABLE 17-continued

| Example No. | Structural formula | Physicochemical data |
|---|---|---|
| 30 | | $^1$H NMR(500 MHz, CDCl$_3$): δ (ppm) = 8.72 (2H, s), 6.48 (1H, s), 5.59 (1H, s), 4.11 (3H, s), 3.99 (3H, s), 3.66 (3H, s), 3.03 (1H, dd, J = 16.4, 13.4 Hz), 2.93-2.86 (1H, m), 2.48 (1H, dd, J = 16.6, 4.4 Hz), 1.01 (3H, d, J = 6.8 Hz). MS(APCl) m/z: 431 (M + H)$^+$ |
| 31 | | $^1$H NMR(400 MHz, CDCl$_3$): δ (ppm) = 8.34 (1H, d, J = 2.4 Hz), 7.80 (1H, dd, J = 8.3, 2.4 Hz), 6.87 (1H, d, J = 8.3 Hz), 6.50 (1H, s), 5.58 (1H, s), 4.02 (3H, s), 3.97 (3H, s), 3.66 (3H, s), 3.04 (1H, dd, J = 16.6, 13.2 Hz), 2.91-2.89 (1H, m), 2.48 (1H, m), 2.48 (1H, dd, J = 16.6, 4.4 Hz), 1.02 (3H, d, J = 6.8 Hz). MS(APCl) m/z: 430 (M + H)$^+$ |
| 32 | | $^1$H NMR(500 MHz, CDCl$_3$): δ (ppm) = 8.77 (1H, brs), 8.72 (1H, brs), 7.90-7.88 (1H, m), 7.46-7.44 (1H, m), 6.52 (1H, s), 5.59 (1H, s), 3.99 (3H, s), 3.66 (3H, s), 3.05-3.02 (1H, m), 2.93-2.89 (1H, m), 2.48 (1H, dd, J = 16.4, 4.1 Hz), 1.02 (3H, d, J = 6.3 Hz). MS(APCl) m/z; 400 (M + H)+ |

The invention claimed is:

1. A method for treating a central inflammatory disease in a subject in need thereof, the method comprising delivering to the subject a compound of general formula (1') or a pharmacologically acceptable salt thereof:

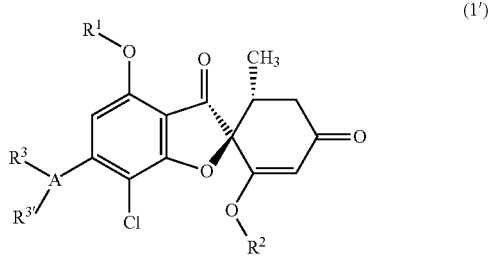

(1')

wherein:

$R^1$ is a C1-C6 alkyl group optionally substituted with the same or different one to two substituents selected from the substituent group X, a C3-C6 cycloalkyl group optionally substituted with the same or different one to two substituents selected from the substituent group X, or a 4-7 membered saturated heterocyclic group optionally substituted with the same or different one to two substituents selected from the substituent group X, $R^2$ is a C1-C6 alkyl group optionally substituted with the same or different one to two substituents selected from the substituent group X, a C3-C6 cycloalkyl group optionally substituted with the same or different one to two substituents selected from the substituent group X, or a 4-7 membered saturated heterocyclic group optionally substituted with the same or different one to two substituents selected from the substituent group X;

A is a 5-membered aromatic heterocyclic ring, a 6-membered aromatic heterocyclic ring, an 8-10 membered condensed aromatic heterocyclic ring, a 5-7 membered unsaturated heterocyclic ring, a 4-7 membered saturated heterocyclic ring, a benzene ring, or a single bond, wherein when it is a single bond, one or the other of $R^3$ and $R^{3'}$ is not present;

$R^3$ and $R^{3'}$ are each independently a hydrogen atom, a halogen atom, a cyano group, a hydroxy group, a C1-C6 alkyl group optionally substituted with the same or different one to two substituents selected from the substituent group X, a C1-C6 alkoxy group optionally substituted with the same or different one to two substituents selected from the substituent group X, a C2-C6 alkenyl group optionally substituted with the same or different one to two substituents selected from the substituent group X, a C2-C6 alkynyl group optionally substituted with the same or different one to two substituents selected from the substituent group X, a C3-C6 cycloalkyl group optionally substituted with the same or different one to two substituents selected from the substituent group X, an amino group optionally substituted with the same or different one to two substituents selected from the substituent group X, a C1-C6 alkoxycarbonyl group optionally substituted with the same or different one to two substituents selected from the substituent group X, a carbamoyl group optionally substituted with the same or different one to two substituents selected from the substituent group X, a phenyl group optionally substituted with the same or different one to two substituents selected from the substituent group X, a 5-membered aromatic heterocyclic group optionally substituted with the same or different one to two substituents selected from the substituent group X, a 6-membered aromatic heterocyclic group optionally substituted with the same or different one to two substituents selected from the substituent group X, a 5-7 membered unsaturated heterocyclic group optionally substituted with the same or different one to two substituents selected from the substituent group X, a 4-7 membered saturated heterocyclic group optionally substituted with the same or different one to two substituents selected from the substituent group X, an 8-10 membered condensed aromatic heterocyclic group optionally substituted with the same or different one to two substituents selected from the substituent group X, or $R^3$ and $R^{3'}$ may form a 5-7 membered unsaturated heterocyclic ring, a 4-7 membered saturated heterocyclic ring, or a C3-C6 cycloalkyl ring as a ring that binds to each other and condenses with A, and the ring is optionally substituted with the same or different one to two substituents selected from the substituent group X;

substituent group X is a halogen atom, a cyano group, a hydroxy group, an oxo group, a C1-C6 alkyl group, a hydroxy C1-C6 alkyl group, a C1-C6 alkoxy C1-C6 alkyl group, a C1-C6 haloalkyl group, a C3-C6 cycloalkyl group, a C3-C6 halocycloalkyl group, a phenyl group optionally substituted with the same or different one to two substituents selected from the substituent group Y, a 5-membered aromatic heterocyclic group optionally substituted with the same or different one to two substituents selected from the substituent group Y, a 6-membered aromatic heterocyclic group optionally substituted with the same or different one to two substituents selected from the substituent group Y, a 4-7 membered saturated heterocyclic group optionally substituted with the same or different one to two substituents selected from the substituent group Y, a C1-C6 alkoxy group, a C1-C6 haloalkoxy group, a C3-C6 cycloalkoxy group, a C3-C6 halocycloalkoxy group, a phenoxy group optionally substituted with the same or different one to two substituents selected from the substituent group Y, a 5-membered aromatic heterocyclic oxy group optionally substituted with the same or different one to two substituents selected from the substituent group Y, a 6-membered aromatic heterocyclic oxy group optionally substituted with the same or different one to two substituents selected from the substituent group Y, a 4-7 membered saturated heterocyclic oxy group optionally substituted with the same or different one to two substituents selected from the substituent group Y, a C1-C6 alkoxycarbonyl group, a C3-C6 cycloalkoxycarbonyl group, a carboxy group, a C1-C6 alkylcarbonyl group, a C3-C6 cycloalkylcarbonyl group, a phenylcarbonyl group optionally substituted with the same or different one to two substituents selected from the substituent group Y, a carbamoyl group, a mono (C1-C6 alkyl) aminocarbonyl group, a di (C1-C6 alkyl) aminocarbonyl group, a mono (C1-C6 alkyl) aminosulfonyl group, a di (C1-C6 alkyl) aminosulfonyl group, an amino group, a mono (C1-C6 alkyl) amino group, a di (C1-C6 alkyl) amino group, a C1-C6 alkoxycarbonylamino group, a mono (C1-C6 alkyl) aminocarbonylamino group, a di (C1-C6 alkyl) aminocarbonylamino group, a C1-C6 alkylcarbonylamino group, a phenylcarbonylamino group optionally substituted with the same or different one to two substituents selected from the substituent group Y, a 5-membered aromatic heterocyclic carbonylamino group optionally substituted with the same or different one to two substituents selected from the substituent group Y, a 6-membered aromatic heterocyclic carbonylamino group optionally substituted with the same or different one to two substituents selected from the substituent group Y, or a C1-C6 alkylsulfonylamino group; and substituent group Y is a C1-C6 alkyl group, a C1-C6 alkoxy group, a halogen atom, or a hydroxy group.

2. The method according to claim 1, wherein $R^1$ is a methyl group, an ethyl group, or a hydroxyethyl group.

3. The method according to claim 1, wherein $R^2$ is a methyl group.

4. The method according to claim 1, wherein the 5-membered aromatic heterocyclic ring or the 5-membered aromatic heterocyclic group in A, $R^3$, or $R^{3'}$ is any one selected from the group:

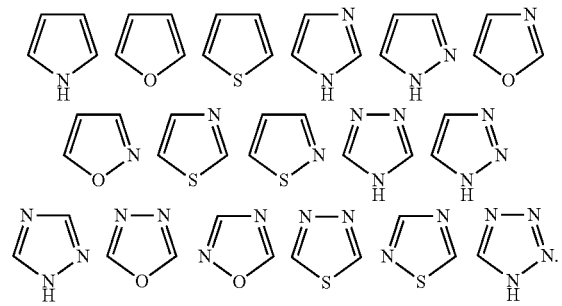

5. The method according to claim 1, wherein the 6-membered aromatic heterocyclic ring or the 6-membered aromatic heterocyclic group in A, $R^3$, or $R^{3'}$ is any one selected from the group:

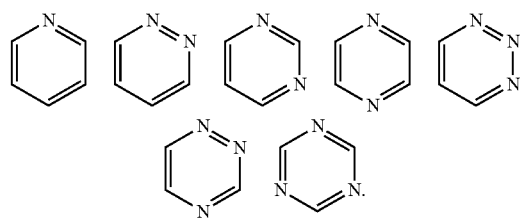

6. The method according to claim 1, wherein the 5-7 membered unsaturated heterocyclic ring or the 5-7 membered unsaturated heterocyclic group in A, $R^3$, or $R^{3'}$ is any one selected from the group:

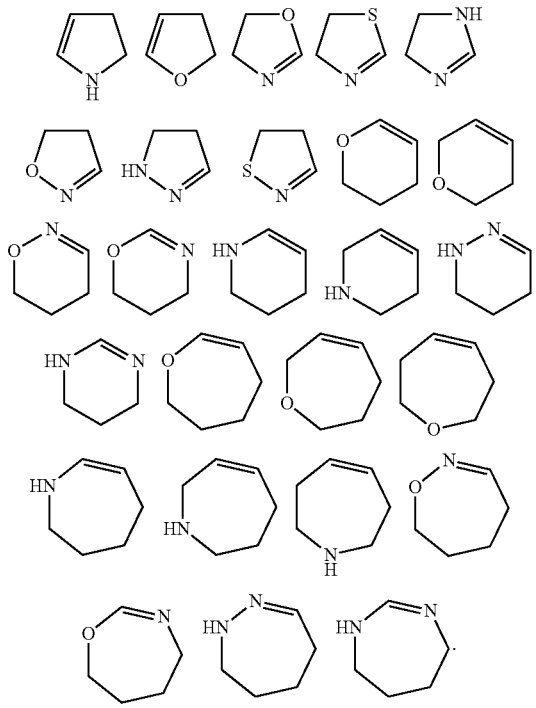

7. The method according to claim 1, wherein the 4-7 membered saturated heterocyclic ring or the 4-7 membered saturated heterocyclic group in A, $R^1$, $R^2$, or $R^3$ is any one selected from the group:

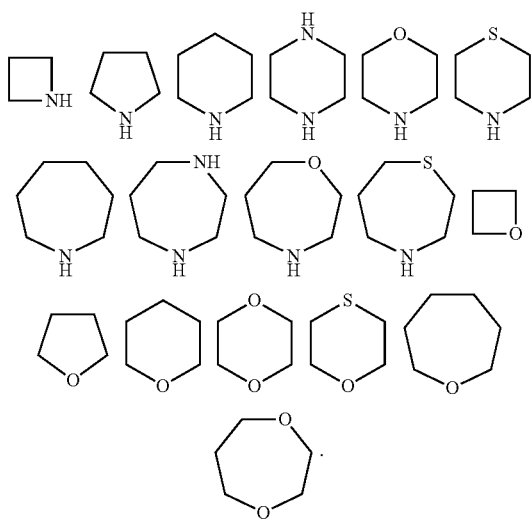

8. The method according to claim 1, wherein A is a 5-membered aromatic heterocyclic ring, $R^3$ is a methyl group, an ethyl group, a hydroxy C1-C3 alkyl group, or a methoxy C1-C3 alkyl group, and $R^{3'}$ is a hydrogen atom.

9. The method according to claim 1, wherein A is any ring selected from the following group, and in the case of two binding groups, $R^{3'}$ is not present:

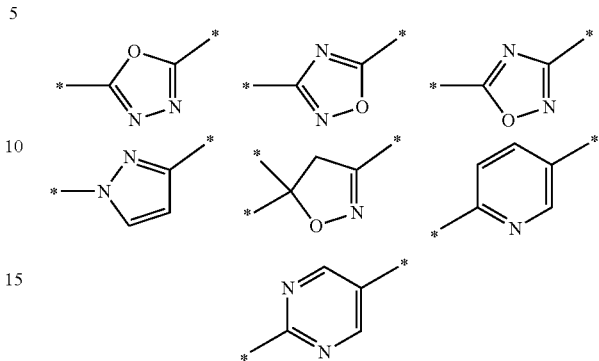

wherein * indicates a binding group.

10. The method of claim 1, wherein the compound of general formula (1') is a compound of general formula (1") or a pharmacologically acceptable salt thereof:

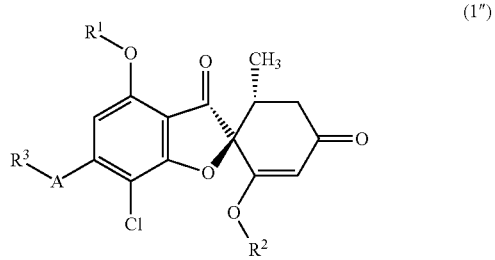

(1")

wherein $R^1$ is a methyl group or an ethyl group;
$R^2$ is a methyl group;
A is any ring selected from the following group

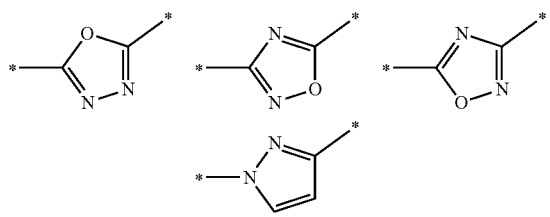

* indicates a binding group; and
$R^3$ is a methyl group or an ethyl group.

11. The method according to claim 1, wherein the compound of the general formula (1') is any compound selected from the following group:
(2S,5'R)-7-chloro-6-(2-hydroxyethoxy)-3,4-dimethoxy-5'-methyl-spiro [benzofuran-2,4'-cyclohex-2-ene]-1',3-dione;
(2S,5'R)-7-chloro-3',4-dimethoxy-6-(2-methoxyethoxy)-5'-methyl-spiro [benzofuran-2,4'-cyclohex-2-ene]-1',3-dione;
2S,5'R)-7-chloro-3',4-dimethoxy-5'-methyl-6-(1-methylpyrazol-3-yl) spiro [benzofuran-2,4'-cyclohex-2-ene]-1',3-dione;

(2S,5'R)-7-chloro-6-(1-ethylpyrazol-3-yl)-3',4-dimethoxy-5'-methyl-spiro [benzofuran-2,4'-cyclohex-2-ene]-1',3-dione;

(2S,5'R)-7-chloro-3',4-dimethoxy-5'-methyl-6-(5-methyl-1,3,4-oxadiazol-2-yl) spiro [benzofuran-2,4'-cyclohex-2-ene]-1',3-dione;

(2S,5'R)-7-chloro-3',4-dimethoxy-5'-methyl-6-(3-methyl-1,2,4-oxadiazol-5-yl) spiro [benzofuran-2,4'-cyclohex-2-ene]-1',3-dione;

(2S,5'R)-7-chloro-3',4-dimethoxy-5'-methyl-6-(5-methyl)-1,2,4-oxadiazol-3-yl) spiro [benzofuran-2,4'-cyclohex-2-ene]-1' 3-dione (2S,5'R)-7-chloro-6-[5-(1-hydroxy-1-methyl-ethyl)-1,3,4-oxadiazol-2-yl]-3',4-dimethoxy-5'-methyl-spiro [benzofuran-2,4'-cyclohex-2-ene]-1',3-dione;

(2S,5'R)-7-chloro-6-[5-[(1S)-1-hydroxyethyl]-1,3,4-oxadiazol-2-yl]-3',4-dimethoxy-5'-methyl-spiro [benzofuran-2,4'-cyclohex-2-ene]-1',3-dione;

(2S,5'R)-7-chloro-6-[5-[(1R)-1-hydroxyethyl]-1,3,4-oxadiazol-2-yl]-3' 4-dimethoxy-5'-methyl-spiro [benzofuran-2,4'-cyclohex-2-ene]-1',3-dione;

(2S,5'R)-7-chloro-4-ethoxy-6-[5-(1-hydroxy-1-methyl-ethyl)-1,3,4-oxadiazol-2-yl]-3'-methoxy-5'-methyl-spiro [benzofuran-2,4'-cyclohex-2-ene]-1',3-dione;

(2S,5'R)-7-chloro-4-ethoxy-6-[5-[(1S)-1-hydroxyethyl]-1,3,4-oxadiazol-2-yl]-3'-methoxy-5'-methyl-spiro [benzofuran-2,4'-cyclohex-2-ene]-1',3-dione;

(2S,5'R)-7-chloro-6-[3-(1-hydroxyethyl)-1,2,4-oxadiazol-5-yl]-3',4-dimethoxy-5'-methyl-spiro [benzofuran-2,4'-cyclohex-2-ene]-1',3-dione;

(2S,5'R)-7-chloro-4-(2-hydroxyethoxy)-3'-methoxy-5'-methyl-6-(5-methyl-1,3,4-oxadiazol-2-yl) spiro [benzofuran-2,4'-cyclohex-2-ene]-1',3-dione;

(2S,5'R)-7-chloro-4-(2-hydroxyethoxy)-3'-methoxy-5'-methyl-6-(3-methyl-1,2,4-oxadiazol-5-yl) spiro [benzofuran-2,4'-cyclohex-2-ene]-1',3-dione;

(2S,5'R)-7-chloro-4-(2-hydroxyethoxy)-3'-methoxy-5'-methyl-6-(5-methyl-1,2,4-oxadiazol-3-yl) spiro [benzofuran-2,4'-cyclohex-2-ene]-1',3-dione;

(2S,5'R)-7-chloro-6-(5-ethyl-1,3,4-oxadiazol-2-yl)-3',4-dimethoxy-5'-methyl-spiro [benzofuran-2,4'-cyclohex-2-ene]-1',3-dione;

(2S,5'R)-7-chloro-3',4-dimethoxy-5'-methyl-6-(5-tetrahydropyran-4-yl-1,3,4-oxadiazol-2-yl) spiro [benzofuran-2,4'-cyclohex-2-ene]-1',3-dione;

(2S,5'R)-7-chloro-3',4-dimethoxy-5'-methyl-6-[5-(1-methyl-4-piperidyl)-1,3,4-oxadiazol-2-yl] spiro [benzofuran-2,4'-cyclohex-2-ene]-1',3-dione;

(2S,5'R)-7-chloro-6-[5-(4-fluoro-1-methyl-4-piperidyl)-1,3,4-oxadiazol-2-yl]-3',4-dimethoxy-5'-methyl-spiro [benzofuran-2,4'-cyclohex-2-ene]-1',3-dione;

(2S,5'R)-7-chloro-3',4-dimethoxy-6-[5-[(1S)-1-methoxyethyl]-1,3,4-oxadiazol-2-yl]-5'-methyl-spiro [benzofuran-2,4'-cyclohex-2-ene]-1',3-dione;

(2S,5'R)-7-chloro-4-ethoxy-3'-methoxy-5'-methyl-6-(5-methyl-1,3,4-oxadiazol-2-yl) spiro [benzofuran-2,4'-cyclohex-2-ene]-1'3-dione;

(2S,5'R)-7-chloro-4-(difluoromethoxy)-3'-methoxy-5'-methyl-6-(5-methyl-1,3,4-oxadiazol-2-yl) spiro [benzofuran-2,4'-cyclohex-2-ene]-1',3-dione;

(2S,5'R)-7-chloro-3',4-dimethoxy-6-[3-(1-methoxyethyl)-1,2,4-oxadiazol-5-yl]-5'-methyl-spiro [benzofuran-2,4'-cyclohex-2-ene]-1',3-dione;

(2S,5'R)-7-chloro-6-[3-(1-hydroxy-1-methyl-ethyl)-1,2,4-oxadiazol-5-yl]-3',4-dimethoxy-5'-methyl-spiro [benzofuran-2,4'-cyclohex-2-ene]-1',3-dione;

(2S,5'R)-7-chloro-3',4-dimethoxy-5'-methyl-6-(1H-pyrazol-5-yl) spiro [benzofuran-2,4'-cyclohex-2-ene]-1',3-dione;

(2S,5'R)-7-chloro-3',4-dimethoxy-6-[1-(2-methoxyethyl)pyrazol-3-yl]-5'-methyl-spiro [benzofuran-2,4'-cyclohex-2-ene]-1',3-dione;

(2S,5'R)-7-chloro-6-(1,8-dioxa-2-azaspiro [4.5] dec-2-en-3-yl)-3,4-dimethoxy-5'-methyl-spiro [benzofuran-2,4'-cyclohex-2-ene]-1',3-dione;

(2S,5'R)-7-chloro-3',4-dimethoxy-5'-methyl-6-(8-methyl-1-oxa-2,8-diazaspiro [4.5]dec-2-en-3-yl) spiro [benzofuran-2,4'-cyclohex-2-ene]-1',3-dione;

(2S,5'R)-7-chloro-3',4-dimethoxy-6-(2-methoxypyrimidin-5-yl)-5'-methyl-spiro [benzofuran-2,4'-cyclohex-2-ene]-1',3-dione;

(2S,5'R)-7-chloro-3' 4-dimethoxy-6-(6-methoxy-3-pyridyl)-5'-methyl-spiro [benzofuran-2,4'-cyclohex-2-ene]-1',3-dione;

(2S,5'R)-7-chloro-3'4-dimethoxy-5'-methyl-6-(3-pyridyl) spiro [benzofuran-2,4'-cyclohex-2-ene]-1',3-dione; or (2S,5'R)-7-chloro-3',4,6-trimethoxy-5'-methyl-spiro [benzofuran-,4'-cyclohex-2-ene]-1',3-dione.

12. The method according to claim 11, the pharmaceutical composition containing a compound (2S,5'R)-7-chloro-6-(1-ethylpyrazol-3-yl)-3',4-dimethoxy-5'-methyl-spiro [benzofuran-2,4'-cyclohex-2-ene]-1',3-dione or a pharmacologically acceptable salt thereof.

13. The method according to claim 11, the pharmaceutical composition containing a compound (2S,5'R)-7-chloro-3,4-dimethoxy-5'-methyl-6-(5-methyl-1,3,4-oxadiazol-2-yl) spiro [benzofuran-2,4'-cyclohex-2-ene]-1',3-dione or a pharmacologically acceptable salt thereof.

14. The method according to claim 11, the pharmaceutical composition containing a compound (2S,5'R)-7-chloro-6-(5-ethyl-1,3,4-oxadiazol-2-yl)-3',4-diethoxy-5'-methyl-spiro [benzofuran-2,4'-cyclohex-2-ene]-1%3-dione or a pharmacologically acceptable salt thereof.

15. The method according to claim 11, the pharmaceutical composition containing a compound (2S,5'R)-7-chloro-6-[3-(1-hydroxy-1-methyl-ethyl)-1,2,4-oxadiazol-5-yl]-3',4-dimethoxy-5'-methyl-spiro [benzofuran-2,4'-cyclohex-2-ene]-1',3-dione or a pharmacologically acceptable salt thereof.

16. The method according to claim 11, the pharmaceutical composition containing a compound (2S,5'R)-7-chloro-4-ethoxy-3'-methoxy-5'-methyl-6-(5-methyl-1,3,4-oxadiazol-2-yl) spiro [benzofuran-2,4'-cyclohex-2-ene]-1',3-dione or a pharmaceutically acceptable salt thereof.

17. The method according to claim 1, wherein the central inflammatory disease is any one selected from a group consisting of Alzheimer's disease, Parkinson's disease, Lewy body dementia, multiple system atrophy, Pick's disease, progressive supranuclear palsy, cerebral cortex basement degeneration, frontotemporal lobe degeneration, Huntington's disease, amyotrophic lateral sclerosis, spinal and bulbar muscular atrophy, spinal muscular atrophy, spinocerebellar degeneration, multiple sclerosis, Creutzfeldt-Jakob disease, fatal familial insomnia, Gerstmann-Straussler-Scheinker syndrome, Down syndrome, Niemann-Pick disease, cerebral amyloid angiopathy, HIV encephalopathy, influenza encephalopathy, hepatic encephalopathy, progressive multifocal leukoencephalopathy, anti-NMDA receptor antibody encephalitis, cerebrovascular disorders, traumatic brain injuries, spinal cord injuries, hypoxic encephalopathy, epilepsy, optic neuritis, congenital metabolic brain diseases, Wernicke's encephalopathy, autism spectrum disorders, attention deficit/hyperactivity disorders, tic disorders, schizophrenia, bipolar disorders, major depressive disorders, persistent depressive disorders, premenstrual dysthymic disorders, anxiety disorders, focal phobia, panic disorders, obsessive compulsive disorders, emotional trauma and stress related disorders, eating disorders, circadian rhythm sleep/wake disorders, narcolepsy, substance related disorders, impulse control disorders, delirium, personality disorders, and Rett's syndrome.

18. The method according to claim 1, wherein the central inflammatory disease is any one selected from a group consisting of Alzheimer's disease, Parkinson's disease, Lewy body dementia, multiple system atrophy, Pick's disease, progressive supranuclear palsy, cerebral cortex basement degeneration, frontotemporal lobe degeneration, Huntington's disease, amyotrophic lateral sclerosis, spinal and bulbar muscular atrophy, spinal muscular atrophy, spinocerebellar degeneration, multiple sclerosis, Creutzfeldt-Jakob disease, schizophrenia, bipolar disorders, major depressive disorders, persistent depressive disorders, premenstrual dysthymic disorders, anxiety disorders, focal phobia, panic disorders, obsessive compulsive disorders, emotional trauma and stress related disorders, eating disorders, circadian rhythm sleep/wake disorders, narcolepsy, substance related disorders, impulse control disorders, delirium, personality disorders, and Rett's syndrome.

19. The method according to claim 1, wherein the central inflammatory disease is any one selected from a group consisting of schizophrenia, bipolar disorders, major depressive disorders, persistent depressive disorders, premenstrual dysthymic disorders, anxiety disorders, focal phobia, panic disorders, and obsessive compulsive disorders.

20. The method of claim 17, wherein the central inflammatory disease is any one selected from a group consisting of treatment resistant depression, postpartum depression, dysthymic disorder, alcohol addiction and drug addiction.

\* \* \* \* \*

UNITED STATES PATENT AND TRADEMARK OFFICE
CERTIFICATE OF CORRECTION

PATENT NO. : 11,407,746 B2
APPLICATION NO. : 16/648570
DATED : August 9, 2022
INVENTOR(S) : Saito et al.

It is certified that error appears in the above-identified patent and that said Letters Patent is hereby corrected as shown below:

On the Title Page

Item (72) Inventors: Please correct "Keiji Saito, Atsugi" to read --Keiji Saito, Atsugi-shi--

Item (72) Inventors: Please correct "Yasuyuki Ogawa, Yokosuka" to read --Yasuyuki Ogawa, Yokosuka-shi--

Item (72) Inventors: Please correct "Mitsuhiro Makino, Shinagawa-Ku" to read --Mitsuhiro Makino, Shinagawa-ku--

Item (56) References Cited, OTHER PUBLICATIONS, Column 2, D'arcy, P.F., et al. cite:
Please correct "1659-665" to read --659-665--

Item (56) References Cited, OTHER PUBLICATIONS, Page 2, Column 2, Line 28: Please correct "Indian Application No. 202017018710" to read --Indian Application No. 202017016710--

In the Specification

Column 7, Lines 20-29, Chemical Formula 4: Please delete Chemical Formula 4 and replace with the following:

Column 19, Line 12: Please correct "4-dimethoxy-'-" to read --4-dimethoxy-5'- --

Column 25, Line 18: Please correct "R$_3$'" to read --R$^{3'}$--

Column 35, Line 48, Chemical Formula 28, C-I: Please correct "Tf reaction" to read --Triflation--

Signed and Sealed this
Tenth Day of January, 2023

Katherine Kelly Vidal
*Director of the United States Patent and Trademark Office*

CERTIFICATE OF CORRECTION (continued)
U.S. Pat. No. 11,407,746 B2

Column 37, Line 13, Chemical Formula 29: Please delete "D-I"

Column 37, Line 22, Chemical Formula 29: Please delete "D-II"

Column 40, Lines 1-53, Chemical Formula 31: Please delete Chemical Formula 31 and replace with the following:

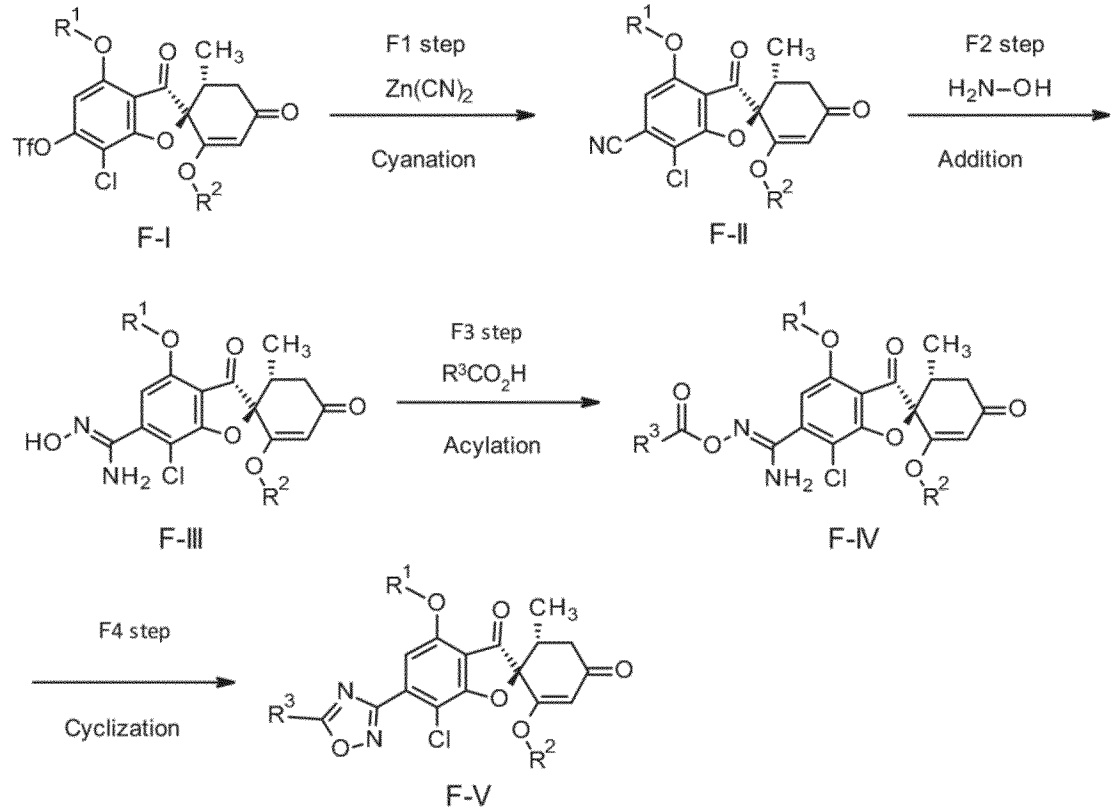

Column 42, Lines 47-67 and Column 43, Lines 1-10, Chemical Formula 33: Please delete Chemical Formula 33 and replace with the following:

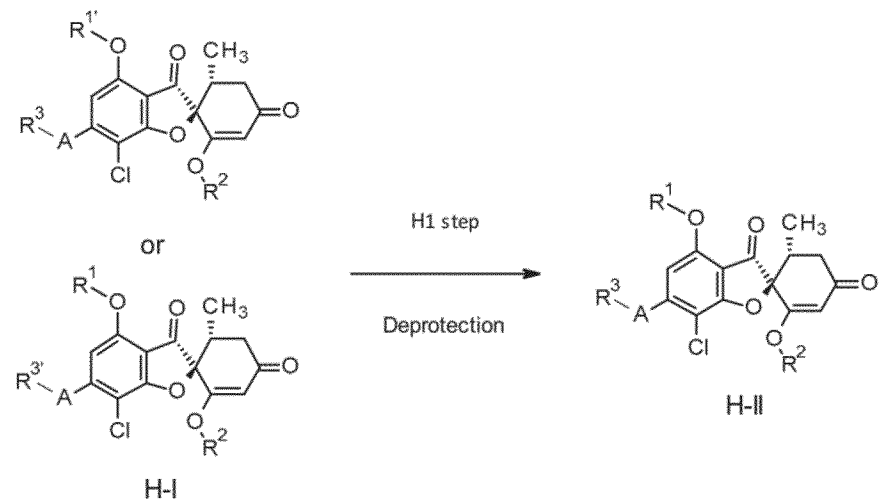

Column 44, Lines 1-10, Chemical Formula 34, Step I-II: Please delete step I-II and replace with the following:

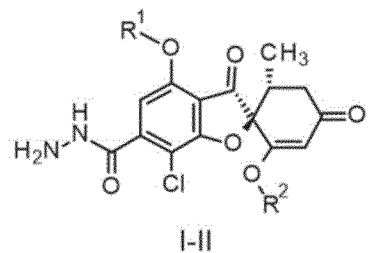

I-II

Column 54, Line 2: Please correct "(VAV)" to read --(V/V)--

Column 54, Line 66: Please correct "(VAV)" to read --(V/V)--

Column 59, Line 14: Please correct "1/I" to read --1/1--

Column 74, Line 11: Please correct "I/O" to read --1/0--

Column 81, Line 54: Please correct "25/i" to read --25/1--

Column 85, Table 6, Example 1(1a), Structural Formula: Please delete Structural Formula 1(1a) and replace with the following:

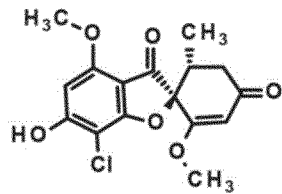

Column 85, Table 6, Example 1(1b), Structural Formula: Please delete Structural Formula 1(1b) and replace with the following:

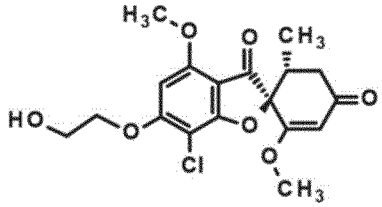

Column 86, Table 6, Example 1(1b), Physicochemical data: Please correct "3.65(3.H, s)" to read --3.62(3H, s)--

Column 87, Table 6, Example 2, Structural Formula: Please delete Structural Formula 2 and replace with the following:

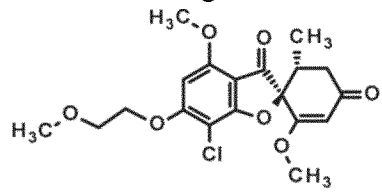

Column 87, Table 6, Example 3(3a), Structural Formula: Please delete Structural Formula 3(3a) and replace with the following:

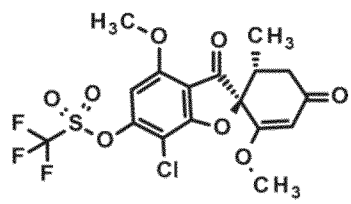

Column 87, Table 6, Example 3(3b), Structural Formula: Please delete Structural Formula 3(3b) and replace with the following:

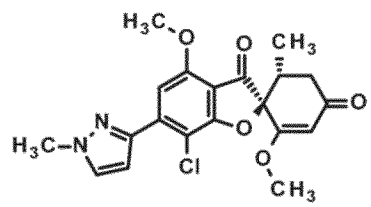

Column 87, Table 6, Example 4, Structural Formula: Please delete Structural Formula 4 and replace with the following:

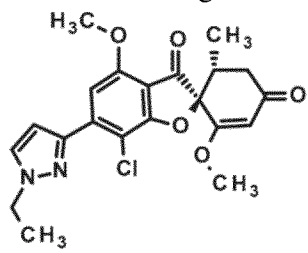

Column 87, Table 6, Example 5(5a), Structural Formula: Please delete Structural Formula 5(5a) and replace with the following:

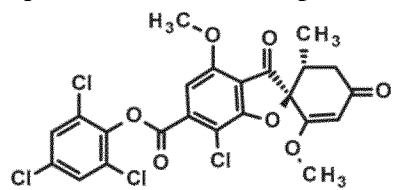

Column 88, Table 6, Example 3(3b), Physicochemical data: Please correct "5.57)1H, s)" to read --5.57(1H, s)--

Column 88, Table 6, Example 4, Physicochemical data: Please correct "(M + + H)" to read
--(M + H)$^+$--

Column 89, Table 7, Example 5(5b), Structural Formula: Please delete Structural Formula 5(5b) and replace with the following:

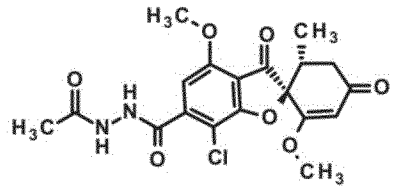

Column 89, Table 7, Example 5(5c), Structural Formula: Please delete Structural Formula 5(5c) and replace with the following:

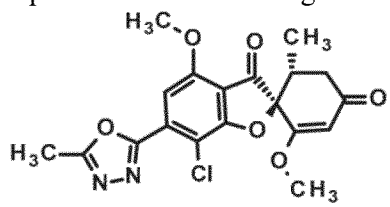

Column 89, Table 7, Example 6(6a), Structural Formula: Please delete Structural Formula 6(6a) and replace with the following:

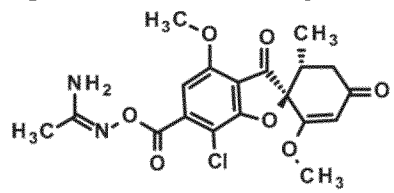

Column 89, Table 7, Example 6(6b), Structural Formula: Please delete Structural Formula 6(6b) and replace with the following:

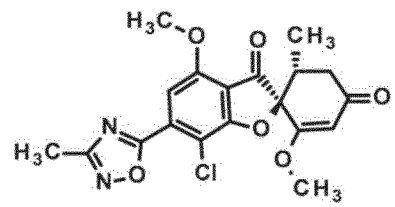

Column 89, Table 7, Example 7(7a), Structural Formula: Please delete Structural Formula 7(7a) and replace with the following:

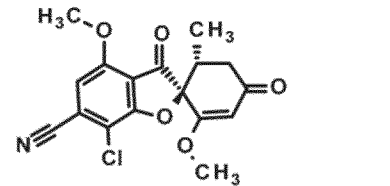

Column 89, Table 7, Example 7(7b), Structural Formula: Please delete Structural Formula 7(7b) and replace with the following:

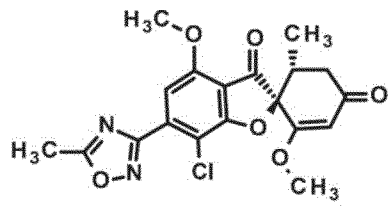

Column 91, Table 8, Example 8(8a), Structural Formula: Please delete Structural Formula 8(8a) and replace with the following:

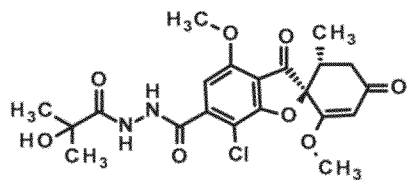

Column 91, Table 8, Example 8(8b), Structural Formula: Please delete Structural Formula 8(8b) and replace with the following:

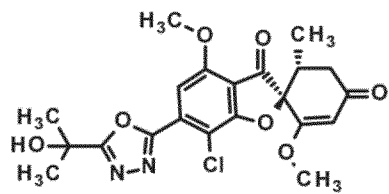

Column 91, Table 8, Example 9(9b), Structural Formula: Please delete Structural Formula 9(9b) and replace with the following:

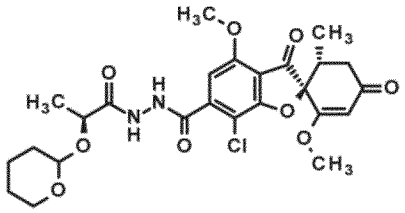

Column 91, Table 8, Example 9(9c), Structural Formula: Please delete Structural Formula 9(9c) and replace with the following:

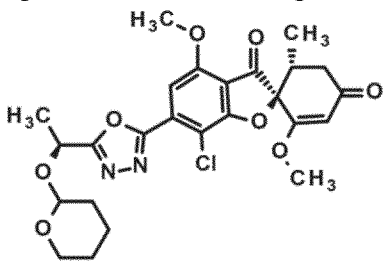

Column 92, Table 8, Example 9(9b), Physicochemical data: Please correct "6.58(0.2H, s)" to read --5.58(0.2H, s)--

Column 92, Table 8, Example 9(9b), Physicochemical data: Please correct "3.58-4.54(4H, m)" to read --3.68-4.54(4H, m)--

Column 93, Table 8, Example 9(9d), Structural Formula: Please delete Structural Formula 9(9d) and replace with the following:

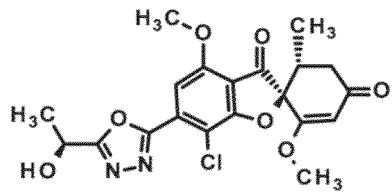

Column 93, Table 9, Example 10(10b), Structural Formula: Please delete Structural Formula 10(10b) and replace with the following:

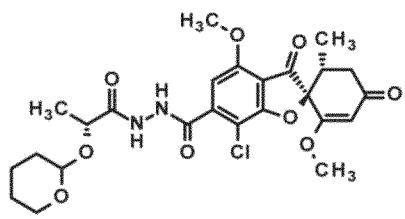

Column 93, Table 9, Example 10(10c), Structural Formula: Please delete Structural Formula 10(10c) and replace with the following:

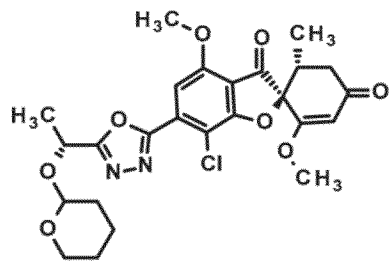

Column 93, Table 9, Example 10(10d), Structural Formula: Please delete Structural Formula 10(10d) and replace with the following:

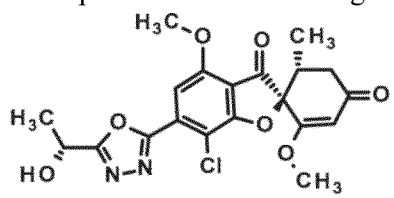

Column 94, Table 9, Example 10(10d), Physicochemical data: Please correct "\MS(ESI)" to read --MS(ESI)--

Column 96, Table 10, Example 12, Physicochemical data: Please correct "5.31-5.25(1H, m)" to read --5.31-5.21(1H, m)--

Column 96, Table 10, Example 13(13a), Physicochemical data: Please correct "3.60-$^1$H NMR" to read --3.60-3.52(1H, m)--

Column 98, Table 10, Example 13(13d), Physicochemical data: Please correct "7.247(1H, s)" to read --7.27(1H, s)--

Column 99, Table 11, Example 14(14b), Structural Formula: Please delete Structural Formula 14(14b) and replace with the following:

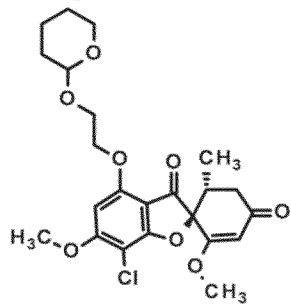

Column 108, Table 13, Example 18(18a), Physicochemical data: Please correct "(2H, rd, J = 11.7, 2.4 Hz)" to read --(2H, td, J = 11.7, 2.4 Hz)--

Column 111, Table 15, Example 23(23e), Structural Formula: Please delete Structural Formula 23(23e) and replace with the following:

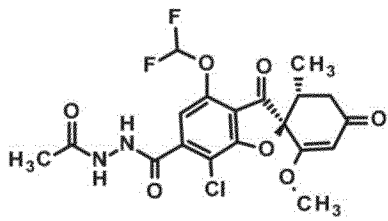

Column 112, Table 15, Example 23(23d), Physicochemical data: Please correct "5.85 (1H, t, J = 72.0 Hz)" to read --6.85 (1H, t, J = 72.0 Hz)--

Column 113, Table 16, Example 25(25a), Structural Formula: Please delete Structural Formula 25(25a) and replace with the following:

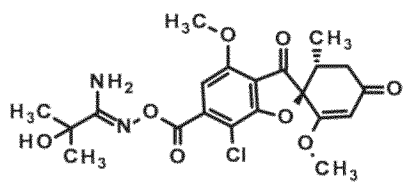

Column 117, Table 17, Example 30, Structural Formula: Please delete Structural Formula 30 and replace with the following:

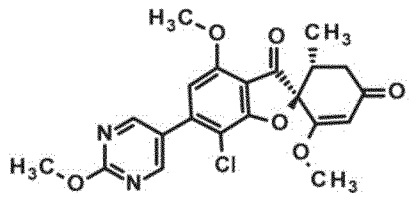

In the Claims

Column 122, Line 59, Claim 11: Please correct "(2S,5R)-7-chloro-6-(2-hydroxyethoxy)-3," to read --(2S,5'R)-7-chloro-6-(2-hydroxyethoxy)-3',--

Column 122, Line 65, Claim 11: Please correct "2S,5'R)" to read --(2S,5'R)--

Column 123, Line 12, Claim 11: Please correct "cyclohex-2-ene]-1' 3-dione" to read --cyclohex-2-ene]-1',3-dione--

Column 123, Lines 20-21, Claim 11: Please correct "4-oxadiazol-2-yl]-3' 4-" to read --4-oxadiazol-2-yl]-3',4- --

Column 123, Line 58, Claim 11: Please correct "1'3-dione;" to read --1',3-dione;--

Column 123, Line 63, Claim 11: Please correct "-5-methyl-spiro" to read -- -5'-methyl-spiro--

Column 124, Line 8, Claim 11: Please correct "-3,4-dimethoxy-" to read -- -3',4-dimethoxy- --

Column 124, Line 16, Claim 11: Please correct "-7-chloro-3' 4-dimethoxy-" to read -- -7-chloro-3',4-dimethoxy- --

Column 124, Line 19, Claim 11: Please correct "-7-chloro-3'4-dimethoxy-" to read -- -7-chloro-3',4-dimethoxy- --

Column 124, Line 22, Claim 11: Please correct "benzofuran-,4'" to read --benzofuran-2,4'--

Column 124, Line 36, Claim 14: Please correct "-1%3-dione" to read -- -1',3-dione--